(12) United States Patent
Kassab et al.

(10) Patent No.: US 11,000,285 B2
(45) Date of Patent: May 11, 2021

(54) LUMINAL GRAFTS AND METHODS OF MAKING AND USING THE SAME

(71) Applicant: 3DT Holdings, LLC, San Diego, CA (US)

(72) Inventors: Ghassan S. Kassab, La Jolla, CA (US); Xiao Lu, San Diego, CA (US)

(73) Assignee: 3DT Holdings, LLC, San Diego, CA (US)

( * ) Notice: Subject to any disclaimer, the term of this patent is extended or adjusted under 35 U.S.C. 154(b) by 311 days.

(21) Appl. No.: 15/957,699

(22) Filed: Apr. 19, 2018

(65) Prior Publication Data

US 2018/0235634 A1   Aug. 23, 2018

Related U.S. Application Data

(63) Continuation-in-part of application No. 15/105,508, filed as application No. PCT/US2014/070931 on Dec. 17, 2014, now Pat. No. 10,314,686.

(Continued)

(51) Int. Cl.
    *A61L 27/24*    (2006.01)
    *A61B 17/11*    (2006.01)
    (Continued)

(52) U.S. Cl.
    CPC ........ *A61B 17/1128* (2013.01); *A61F 2/0077* (2013.01); *A61F 2/06* (2013.01);
    (Continued)

(58) Field of Classification Search
    CPC ..... A61B 17/1128; A61K 38/39; A61L 27/24; A61L 27/507; A61L 2430/32; A61L 24/102; A61L 27/3878; A61F 2310/00371
See application file for complete search history.

(56) References Cited

U.S. PATENT DOCUMENTS 5,024,841 A * 6/1991 Chu ................. A61K 38/39
                                                  128/DIG. 8
5,607,590 A * 3/1997 Shimizu ............ A61L 15/325
                                                      210/490

(Continued)

FOREIGN PATENT DOCUMENTS

WO    2013/120082 A1    8/2013

OTHER PUBLICATIONS

International Searching Authority, International Search Report, PCT/US2014/070931, dated May 14, 2015.

(Continued)

*Primary Examiner* — Seema Mathew

(74) *Attorney, Agent, or Firm* — Mark C. Reichel; Natalie J. Dean; Reichel Stohry Dean LLP

(57) ABSTRACT

Luminal grafts and methods of making and using the same. An exemplary luminal graft of the present disclosure is configured as a generally tubular element configured for nerve cells to grow therethrough and comprises at least one sheet of biological tissue having elastin fibers and collagen fibers, with the elastin fibers being a dominant component thereof; and a plurality of microchannels formed on a surface of the at least one sheet of biological tissue, each of the microchannels extending longitudinally between a first end and a second end of the at least one sheet of biological tissue and configured to provide intraluminal structural guidance to nerve cells proliferating therethrough.

12 Claims, 19 Drawing Sheets

Related U.S. Application Data

(60) Provisional application No. 62/520,847, filed on Jun. 16, 2017, provisional application No. 62/492,544, filed on May 1, 2017, provisional application No. 62/488,042, filed on Apr. 20, 2017, provisional application No. 62/047,691, filed on Sep. 9, 2014, provisional application No. 61/917,051, filed on Dec. 17, 2013.

(51) Int. Cl.
| | | |
|---|---|---|
| *A61L 27/58* | (2006.01) | |
| *A61L 27/26* | (2006.01) | |
| *A61L 27/36* | (2006.01) | |
| *A61L 27/54* | (2006.01) | |
| *A61M 1/36* | (2006.01) | |
| *A61L 27/50* | (2006.01) | |
| *A61F 2/00* | (2006.01) | |
| *A61F 2/06* | (2013.01) | |
| *A61L 27/56* | (2006.01) | |
| *A61B 17/00* | (2006.01) | |

(52) U.S. Cl.
CPC ............ *A61L 27/26* (2013.01); *A61L 27/3604* (2013.01); *A61L 27/507* (2013.01); *A61L 27/54* (2013.01); *A61L 27/56* (2013.01); *A61L 27/58* (2013.01); *A61M 1/3655* (2013.01); *A61B 2017/00004* (2013.01); *A61B 2017/00526* (2013.01); *A61B 2017/00876* (2013.01); *A61B 2017/00893* (2013.01); *A61B 2017/1107* (2013.01); *A61B 2017/1132* (2013.01); *A61F 2002/0081* (2013.01); *A61F 2210/0004* (2013.01); *A61F 2210/0076* (2013.01); *A61L 2300/252* (2013.01); *A61L 2300/414* (2013.01); *A61L 2300/604* (2013.01); *A61L 2300/622* (2013.01); *A61L 2430/32* (2013.01)

(56) References Cited

U.S. PATENT DOCUMENTS

| | | | |
|---|---|---|---|
| 5,922,024 A * | 7/1999 | Janzen | A61F 2/12 623/8 |
| 6,517,571 B1 | 2/2003 | Brauker et al. | |
| 6,596,296 B1 * | 7/2003 | Nelson | D06M 15/03 424/426 |
| 9,259,334 B2 * | 2/2016 | Kaufmann | A61L 27/58 |
| 9,675,358 B2 * | 6/2017 | Wagner | A61L 27/58 |
| 10,582,996 B2 * | 3/2020 | Wang | A61L 27/20 |
| 10,799,620 B2 * | 10/2020 | Xie | A61L 27/54 |
| 2002/0058983 A1 | 5/2002 | Dzau et al. | |
| 2003/0027332 A1 * | 2/2003 | Lafrance | A61F 2/2412 435/366 |
| 2006/0257447 A1 | 11/2006 | Hinds et al. | |
| 2008/0112998 A1 * | 5/2008 | Wang | A61K 35/44 424/423 |
| 2008/0131473 A1 * | 6/2008 | Brown | A61L 27/52 424/423 |
| 2009/0248145 A1 * | 10/2009 | Chan | A61L 27/507 623/1.41 |
| 2010/0196478 A1 * | 8/2010 | Masters | A61K 9/0024 424/484 |
| 2015/0024025 A1 * | 1/2015 | Floyd | A61L 27/56 424/425 |

OTHER PUBLICATIONS

Internaonal Searching Authority, Written Opinion of the International Searching Authority, PCT/US2014/070931, dated May 14, 2015.

* cited by examiner

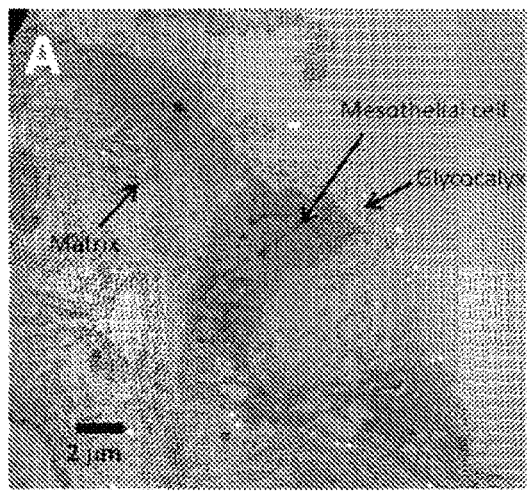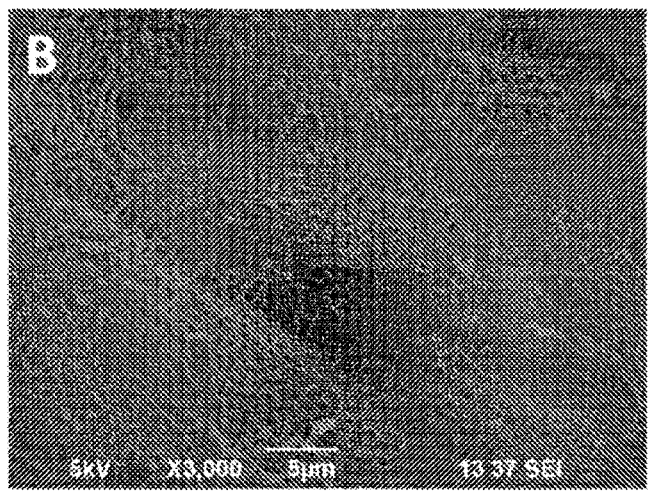
Fig. 13A   Fig. 13B
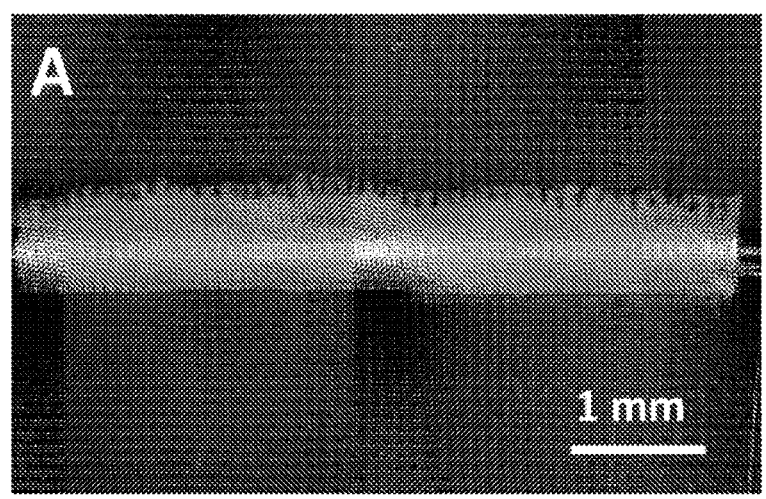
Fig. 14A
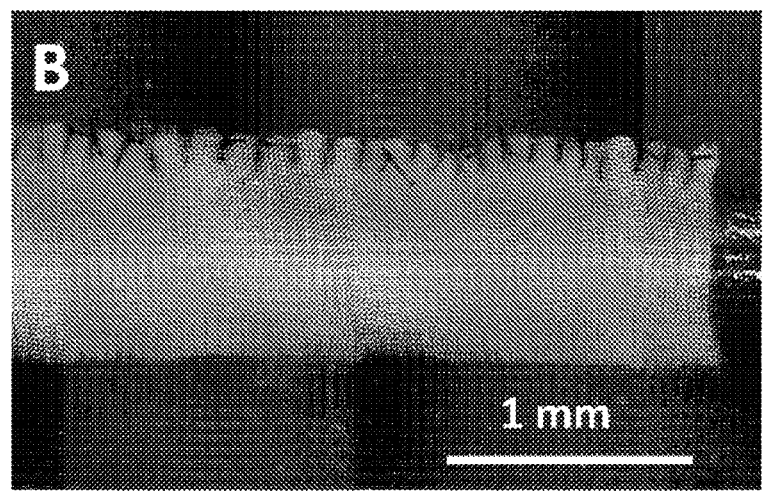
Fig. 14B

LUMINAL GRAFTS AND METHODS OF MAKING AND USING THE SAME

PRIORITY & RELATED APPLICATIONS

The present application a) is related to, and claims the priority benefit of, U.S. Provisional Patent Application Ser. No. 62/520,847, filed Jun. 16, 2017, b) is related to, and claims the priority benefit of, U.S. Provisional Patent Application Ser. No. 62/492,544, filed May 1, 2017, c) is related to, and claims the priority benefit of, U.S. Provisional Patent Application Ser. No. 62/488,042, filed Apr. 20, 2017, and d) is related to, claims the priority benefit of, and is a U.S. continuation-in-part patent application of, U.S. patent application Ser. No. 15/105,508, filed Jun. 16, 2016, which is related to, and claims the priority benefit of, and is a U.S. § 371 national stage patent application of, International Patent Application Serial No. PCT/US2014/070931, filed Dec. 17, 2014, which is related to, and claims the priority benefit of, a) U.S. Provisional Patent Application Ser. No. 62/047,691, filed Sep. 9, 2014, and b) U.S. Provisional Patent Application Ser. No. 61/917,051, filed Dec. 17, 2013. The entire contents of the aforementioned applications are hereby incorporated by reference in their entirety into this disclosure.

BACKGROUND

Luminal or tubular grafts are useful for an extensive number of medical applications.

A. Small-Diameter Vascular Grafts

Vascular grafts, especially, are in high demand due to recent expansions in the field. A major problem in vascular surgery is how to effectively supply blood to organs and tissues whose blood vessels are inadequate either through congenital defects or acquired disorders such as trauma, arteriosclerosis or other diseases.

To date, the search for the ideal blood vessel substitute has focused on biological tissues and synthetics. Initially, arterial homografts (human arteries) were used to restore vascular continuity; however, limited supply, inadequate sizes, development of aneurysms and arteriosclerosis necessitated the search for a better substitute. Additional substitutes that have been employed include autologous blood vessels, vessels of xenogenic origin, as well as vascular prostheses typically made from Dacron or polytetrafluoroethylene.

Despite intensive efforts to improve the nature of blood vessel substitutes, many problems with conventional substitutes remain. For example, conventional vascular grafts typically suffer from high failure rates related to (a) occlusion by thrombosis or kinking, or due to an anastomotic or intimal and subintimal hyperplasia (exuberant cell growth at the interface between the native vessel and graft); (b) a decreasing caliber of the blood vessel substitute; (c) resulting infection; (d) biological failure or degradation; and/or (e) aneurysm formation. Other problems may involve compliance mismatches between the host vessel and a synthetic vascular prosthesis, which may result in anastomotic rupture, stimulated exuberant cell responses, and/or disturbed flow patterns and increased stresses leading to graft failure.

Vascular grafts can be used in the treatment of numerous types of medical conditions, spanning a broad range of biological tissues. For example, and as described in further detail below, vascular grafts can be employed in treating cardiovascular disease, obtaining vascular access for hemodialysis, as well as in nerve regeneration procedures. Unfortunately, conventional knowledge has yet to identify a functional graft that is capable of addressing the various biological issues necessary to maintain long term patency for these applications.

For example, cardiovascular disease, including coronary artery and peripheral vascular disease, is typically treated by surgical replacement. With around 8 million people with peripheral artery disease, 500,000 patients diagnosed with end-stage renal disease, and 250,000 patients undergoing coronary bypass surgeries each year in the United States alone, there is a significant demand for luminal grafts in vascular surgery. This is especially true with respect to functional small-caliber blood vessels (<4 mm in diameter).

Despite this clear clinical need for a functional small-diameter vessel graft, replacement therapy with respect to small-diameter blood vessels has been met with limited success. One reason or this is that the application of conventional methods for creating replacements for large-caliber vessels have generally proved inadequate when applied to small-caliber vessel substitutes. For example, while artificial, biological and modulated materials (including, without limitation, synthetic polymer scaffolds (polyurethane), synthetic scaffolds treated with biological molecules such as collagen, heparin, laminin, anti-coagulant peptides, etc.) have proven successful with respect to large-caliber vessel grafts, these materials are not particularly suited for creating small-diameter luminal grafts. This is due, at least in part, to the lower blood flow velocities of smaller vessels, which require a different set of design criteria and introduce a host of new problems not encountered in large-caliber vessel substitutes. Indeed, in low-flow situations, synthetic and other conventional grafts are prone to sudden thrombosis and provoking a wound-healing response from adjacent vessels and the surrounding tissue that under some circumstances narrows the lumen and reduces blood flow therethrough. Accordingly, when conventional materials are used to prepare small-diameter vessel grafts, the replacement grafts' have shown an increased tendency (a) for thrombogenicity; (b) to develop embolism and/or occlusion of the graft lumen (i.e. intimal hyperplasia and negative remodeling); (c) to develop anastomotic intimal hyperplasia; (d) for aneurysm formation of the graft itself; and/or (e) to cause a compliance mismatch with the host vessel.

For these reasons, operations using autologous vessels remain the standard for small-diameter grafts. However, there are also issues associated with this approach. Many patients do not have a vessel suitable for use because of vascular disease, amputation, or previous harvest, and this method requires a second complicated surgical procedure to obtain the vessel. As a result, there is a demand for a vascular prosthesis which is suited to the small-diameter blood vessels.

Recently, tissue engineering has emerged as an alternative approach to address the shortcomings of current options. Specifically, decellularized scaffolds (decellularized artery, vein and/or other suitable tissue) have been made by removing the cellular components of the tissue, thereby resulting in a decellularized scaffold that is entirely comprised of natural extracellular matrix. After the decellularized scaffold is formed, the same is recellularized by host cells. For example, the scaffolds may host smooth muscle cells and fibroblasts that mimic native blood vessels. Purified proteins have also been used to form scaffolds of such tubular constructs.

Preparation of the scaffolds typically requires a few months (about three months) for the native smooth muscle and fibroblasts to seed on the scaffold for inhibition of immunoreactions before implantation. Due to the composition of such decellularized scaffolds, the scaffolds retain beneficial native mechanical properties, promote regeneration and exhibit favorable biocompatibility. While over the last decade, cardiovascular tissue engineering has experienced a dramatic paradigm shift from biomaterial-focused approaches and towards the more biology-driven strategies, there currently remains no functional vessel graft that has addressed the various biological issues necessary to maintain long term patency.

B. Hemodialysis

It has been estimated that, globally, approximately 8.3% of adults have diabetes and the number of people with diabetes is set to rise beyond 592 million by 2025. Further, according to recent projections, 53.1 million Americans will have diabetes in the year 2025 (diagnosed and undiagnosed), representing a 63% increase from the number of Americans with diabetes today. As may be expected, the burden of cardiovascular disease and premature mortality that is associated with diabetes will also substantially increase, reflecting not only an increased amount of individuals with coronary artery disease, but an increased number of younger adults and adolescents with type 2 diabetes who are at a two- to four-fold higher risk of experiencing a cardiovascular-related death as compared to non-diabetics. Accordingly, aside from promoting awareness and prevention of the disease, there is a vast need to facilitate both treatment and cost efficacy in the treatment of those afflicted with the chronic disorder.

Adults with diabetes or high blood pressure (or both) have an increased risk of developing chronic kidney disease (CKD). It has been estimated that more than 20 million Americans have CKD, including approximately 1 of 3 adults with diabetes and 1 of 5 adults with high blood pressure. Other risk factors for CKD include cardiovascular disease, obesity, high cholesterol, lupus, and a family history of CKD. While some of these patients undergo treatment to maintain some kidney functions, some patients lose their kidney function altogether, which is referred to as end-stage renal disease (ESRD). As the kidneys are responsible for filtering out waste products from the blood, patients with ESRD require either dialysis or a kidney transplant to survive. Conventionally, three-times weekly, in-center dialysis is the most commonly performed modality.

In 2012, it was estimated that around 398,000 Americans relied on some form of dialysis to keep them alive. Needless to say, the cost associated with providing such procedure is considerable. A significant portion of the total cost is spent on hemodialysis vascular access, which has been long considered to be the most problematic part of dialysis. There are three basic kinds of vascular access for hemodialysis: 1) ateriovenous (AV) fistula; 2) an AV graft; or 3) a venous catheter. Hemodialysis patients who do not have adequate veins for a fistula become candidates for an AV graft or a venous catheter. Conventional AV grafts and venous catheters are typically discouraged due to their high morbidity and mortality. Specifically, such types of vascular access tend to have more problems than fistulas with respect to clotting and infection.

An AV graft is created by connecting an artery to a vein with a synthetic tube of biocompatible material (i.e. the graft), and implanting the same subcutaneously. The graft then functions as an artificial vein that can be used repeatedly for needle placement and blood access. One problem associated with this technique is that thrombosis of the graft is common, which can develop due to poor blood flow. Another risk relates to an increased risk in the development of vascular access steal syndrome, which refers to vascular insufficiency resulting from the AV graft. Considering the limitations of conventional AV grafts and the prevalence of hemodialysis in the United States alone, a need exists for an improved design. Accordingly, it would be desirable to have a vessel graft that is capable of long term patency and does not increase the risk of aneurysm.

C. Nerve Regeneration

Nerve injuries are common in clinical practice. Nervous system injuries are most commonly caused by trauma, tissue loss, bone fracture, or burns. Severe nerve injury is either a segmental transection or defect resulting in partial or total loss of the motor, sensory, and autonomic functions conveyed by the injured nerves to the denervated segments of the body. In many cases, these injuries can lead to chronic functional disability as well as the development of neuropathic pain, both of which can have a devastating impact on patient quality of life.

While the central nervous system is, for the most part, incapable of self-repair and regeneration, the peripheral nervous system (PNS) has the intrinsic ability to repair and regenerate. Specifically, nerve fiber regeneration is due to the growth of transected axons of the nerve stump proximal to the lesion and not to a regenerative process of axons of the distal stump. Indeed, functional re-innervation requires that the axons extend from the proximal nerve stump until reaching their distal target. However, PNS nerve regeneration is a complex biological phenomenon and typically does not occur spontaneously without treatment. Furthermore, nerves in the PNS can regenerate only under certain circumstances. For example, while spontaneous natural regeneration may occur in peripheral nerve injuries if the distance to target is short, over large gaps, microsurgical repair is necessary.

Historically, the common surgical approach to repairing a transected nerve has been direct suture (or gluing) of the two stumps together when the ends can be approximated without tension. However, this technique is difficult, time-consuming and often yields poor functional results. Furthermore, where nerve substance loss occurs (i.e. the defect is longer), a neurorrhaphy without tension at the site of repair cannot be performed. For more extensive peripheral nerve injuries/lesions (e.g., where the nerve defect gap is longer than, for example, about 20 mm) the surgical repair of nerve gap has conventionally been achieved using autologous nerve grafts harvested from other sites in the body. In such cases, a nerve graft is typically used to bridge the two stumps or ends and promote nerve regeneration, rather than suturing the two stumps under tension. However, there are significant disadvantages to this autologous nerve grafting technique as well as it requires an extra incision for the withdrawal of a healthy nerve (which could also result in sensory residual deficits) and, often, the length of the graft material is limited. Furthermore, sensory and motor neurons have different Schwann cell modalities and, if placed in the incorrect microenvironment, may have limited regenerative ability. As such, autologous nerve grafting is limited to a critical nerve gap of approximately 5 cm in length. While allografts may be used for nerve gaps of over 5 cm, allografts require the use of extensive immune suppression up to 18 months post implantation.

Currently, biomedical strategies for PNS regeneration focus on developing alternative treatments to nerve grafting (e.g., nerve guidance channels or tubulization), whereas efforts for spinal cord injury are focused on creating a permissive environment for regeneration. Unfortunately, a solution to completely repair long spinal cord injuries has not yet been identified.

Sutureless tubulization techniques provide an alternative to direct nerve sutures and nerve grafting. Tubulization involves forming non-nervous luminal grafts (e.g., venous or arterial conduit grafts) to create optimal conditions for nerve regeneration over the empty space intentionally left between two nerve stumps. Nevertheless, such alternatives have not shown substantial benefits compared with standard nerve grafts.

In order to achieve a better clinical outcome, various materials (both biological and synthetic) have been studied in connection with tubulization. Enriching the graft tubes with other tissue (e.g., pieces of nerve or skeletal muscle to form a "biological" graft) has seen some success when used in tubulization applications, however, only with limited efficacy—functional recovery has only been achieved for injured gaps shorter than about 4 cm for both sensory and mixed nerves. Alternatively, non-biological synthetic materials have also been employed, albeit also with limited success. When nonabsorbable synthetic grafts are used in humans, the occurrence of complications due to local fibrosis (triggered by the implant material) and nerve compression becomes a substantial concern. This is due, at least in part, to the graft's non-degradable nature and its inability to adapt to the nerve growth and maturation. As such, synthetic nerve repair conduits used for bridging strategies have increasingly been made of biodegradable or bioresorbable materials. Among these, polyglycolic acid nerve repair conduits are an example of one biodegradable material that has shown a decreased prevalence of complications as compared to non-absorbable synthetic materials. However, even such bioabsorbable/bioresorbable nerve conduits have flaws and the results thus far are still not satisfactory.

Finally, nerve reconstruction by tissue engineering has seen an increased interest in recent years. In tissue engineering, two concepts have guided the development of recent nerve regeneration technologies: 1) the manipulation of tissues and organs in vitro to fashion conduit should attempt to mimic important features of the nerve environment; and 2) various elements considered essential for promoting nerve fiber regeneration are missing in non-nerve grafts and, as such, an attempt should be made to enrich biological or synthetic tubes with the same. However, currently, despite the ongoing research and working concepts, conventional conduits (whether formed by tissue engineering or otherwise) continue to fall short and exhibit critical flaws. Accordingly, it would be desirable to have a luminal graft that satisfies all of the biological requirements necessary for the successful promotion of peripheral nerve regeneration.

In the Diabetes Mellitus and Chronic Kidney Disease patient, End Stage Renal Disease (ESRD) is the terminal phase requiring kidney replacement therapy for survival. Hemodialysis is the primary therapy for kidney function replacement. In 2011, the United States Renal Disease System (USRDS) reports approximately 500,000 patients receiving hemodialysis.[1] The USRDS reports expenditures for ESRD care approached $50 billion.

Vascular access of arterial blood is the preferred method for hemodialysis. For effective hemodialysis, maintaining a patent, high-flow vascular access site is the minimum requirement. In 2011, approximately $6.2 billion was spent just to keep existing vascular access sites open. For hemodialysis, the current solutions (arteriovenous fistula (AVF), arteriovenous graft (AVG), and tunneled catheter (TC) do not offer overall satisfactory outcomes in the immediate, short-term, or long-term. Patients must endure an access method that introduces frequently occurring, significant and costly complications.

For the ESRD patient, hemodialysis is required to replace kidney function, filtering waste and toxins from the blood, excreting excess fluids, and maintaining electrolyte balance. Hemodialysis requires a surgically created access site for the chronic application of the large bore needles, in which the blood is extracted, cleaned and balanced externally, and then reinserted into the body. For the ESRD patient, it is essential to have a functioning vascular access site that can tolerate the multi-weekly dual-needle puncture injury while sustaining high blood flow.

Despite advances in long-term dialysis vascular access, a satisfactory solution remains elusive for patients and physicians.

In recent years, the AVF has become the widely preferred first choice for permanent vascular access because of a lower incidence of associated morbidity and mortality than other access types. Per the Kidney Disease Outcomes Quality Initiative (KDOQI) guidelines, the Rule of Three 6s must exist for vascular access, namely that the selected vein must mature to allow 600 ml/min blood flow, growth to a diameter greater than 6 mm, and resides less than 6 mm below the surface of the skin.

Fistulas require significant time to mature for surgical healing of the anastomosis site and wound, and more importantly vein adaptation (diameter enlargement and wall thickening) in response to the high arterial blood flow rate and pressure. Besides the lengthy time to mature, one of the primary drawbacks to AVFs is the high failure to mature rate (up to 57%) where the surgically created fistula never enters service as an access site for dialysis.

The major advantage of AVF is for those that mature and functionally provide dialysis access; the subsequent complication and intervention rates are 7-fold lower than currently available AVGs. There is a wide range of failure rates in the literature ranging from 25% to 57%. In a multi-center prospective initiative by Huijbregts et al. of 491 new fistulas, the 1-year primary patency (from the day of surgical creation and includes failure to mature) was 49%. In a large meta-analysis (n=12,383), the 1-year primary patency (defined as creation of access to first AVF intervention to maintain or restore blood flow) and secondary patency (defined as creation of access until access abandonment including failures), was 60% and 71%. Primary failures were reported to at 23%. To date, the performance of AVFs in a level 1 randomized clinical trial where an intent-to-treat approach to avoid treatment by indication bias has not been studied. The AVF solution may be the preferred form of hemodialysis, but it is not without significant problems.

Synthetic and autologous vascular grafts have been available for hemodialysis access for many years now. The expanded polytetrafluoroethylene (ePTFE) with Heparin-bonded to the material has become the preferred graft material choice. From a hemodialysis access hierarchy standpoint, AVGs are a second or third choice behind a native fistula or a second native fistula in another upper extremity location. Recent professional dialogue argues that recommendations originating from KDOQI to prefer AVFs over grafts are largely based on single center studies patency results from the 1980's and early 90's that excluded those fistulas that failed to mature. And in patients with compromised forearm vessels, grafts have been shown to have higher patency than AVFs. Grafts have distinct advantages over fistulas, namely an engineered diameter for appropriate blood volume, the time to become operational is significantly shorter than fistula (1-2 weeks), low failure to mature rates, and lower tunneled catheter use. If thrombosis occurs the clearing of clot is more predictable. Most importantly, functional secondary patency is equal to the fistula. Current AVG have significant disadvantages compared to AVFs, namely five times the infection risk, lower primary patency, higher rates of thrombosis, higher intervention rates, a higher potential for pseudo-aneurysm (needle puncture sites due to material failure), stenosis at the venous anastomosis, and a 2.5× higher mortality rate (this position is challenged in the literature as it hypothesized that sicker patients receive more grafts). Despite their shortcomings of thrombosis and infection, the advantages of dialyzing quickly with low failure rates and comparable secondary patency rates positions AVG as a viable option.

TC are the temporary option for hemodialysis during which an AVF or AVG is given time to mature. During this lag time for the permanent access solutions to become operational, a dual-lumen catheter, usually placed in the non-dominant internal jugular and terminating in the superior vena cava, is inserted to enable dialysis in the short-term. They may also be used as permanent access when a patient lacks a suitable site for access. The advantage for TC is that dialysis can begin immediately, but there exists several significant shortcomings, including primary dysfunction, frequent low flow due to thrombosis, fibrin collecting on the catheter tip or an anatomically malposition tip, central vein stenosis/thrombosis, or infection originating at the external site. Each shortcoming requires intervention ranging from a simple catheter-lumen thrombolysis to a radiologic procedure and/or extensive antibiotic therapy. Infection of the tunneled catheter is a common complication. When the catheter is left in place less than 2 weeks, incidence of infection is less than 5%. However, incidence increases to 25% with longer placement. The clinical need for a solution that can be readily created, mature at a high rate, begin dialysis quickly, demonstrate low early and late thrombosis rates, exhibit low neointimal hyperplastic tendencies, and yield long-term access is clearly evident.

BRIEF SUMMARY

In at least one exemplary embodiment of a luminal graft (also referred to as a blood vessel graft in various embodiments herein that pertain to blood vessel grafting in particular) of the present disclosure, the graft comprises a generally tubular element configured for plasma and/or blood cells to flow therethrough. The tubular element is comprised of elastin and collagen fibers, with the elastin fibers being a dominant component thereof. Alternatively, or additionally, the tubular element may comprise a ratio of collagen fibers to elastin fibers ranging from about a 1.2 ratio value to about a 0.8 ratio value. For example, in at least one embodiment, the collagen to elastin ratio may comprise about a 1:1 ratio. Alternatively, the collagen to elastin ratio may comprise about a 1.10 ratio value. In at least one exemplary embodiment, the biological tissue comprised pulmonary ligament tissue or visceral pleura tissue. Additionally or alternatively, the at least one layer may comprise a biological tissue comprising between about 11% and about 12% collagen fibers and between about 12.5% and 13.5% elastin fibers. In yet another embodiment, the biological tissue exhibits mechanical properties that are similar pre- and post-fixation. Additionally or alternatively, in at least one embodiment, the generally tubular element is flexible.

Where the luminal graft comprises at least one layer, each of the layers may comprise a first edge and a second edge, both of which extend between the proximal and distal ends of the layer. Additionally, each of the layers may comprise a seam extending between the proximal and distal ends thereof, the seam comprising the first and second edges sealed together via one or more closure mechanisms. For example, the closure mechanism(s) may comprise an arrow-lock configuration, magnetic strips, a series of perforations and sutures, and/or a series of clips. Additionally or alternatively, the closure mechanism may comprise sutures.

In at least one embodiment, the at least one layer of the generally tubular element comprises three concentric layers. There, at least one of the layers may be comprised of a synthetic material and at least one of the layers is comprised of pulmonary ligament or pulmonary visceral pleura. In those embodiments having more than one layer, the seam of each of the layers may be offset from the seam of each of the immediately adjacent layer(s). While such offset may comprise any angle, in at least some embodiments, the offset comprises between about a ninety degree angle and about a one hundred and eighty degree angle.

In yet another embodiment, the lumen of the generally tubular element comprises at least one diameter that is equal to or less than about 5 mm or equal to or less than about 1 mm.

Still further, the generally tubular element may comprise a luminal surface having mesothelium thereon. Additionally, the generally tubular element may be configured to allow cells from an adjacent blood vessel to integrate within the fibers thereof and thus remodel the same when the graft is implanted within a mammalian body.

Additional embodiments of the luminal graft of the present disclosure are formed by wrapping at least one layer around a mandrel having a cylindrical configuration and at least one diameter to form the generally tubular element; coupling at least one closure mechanism with the at least one layer to form a seal along the length of the layer; and withdrawing the mandrel from the generally tubular element. The at least one diameter of the tubular element may be substantially equivalent to the at least one diameter of the mandrel. In at least one embodiment, the at least one diameter of the mandrel comprises about or less than 5 mm, or even about or less than 1 mm. The seam of the at least one layer may comprise a minimal profile. Additionally or alternatively, the graft may be further formed by wrapping at least one additional layer around the mandrel and the previously wrapped layer and coupling at least one closure mechanism with each additional layer to form a seam along the length thereof. For example, in at least one embodiment, the generally tubular element comprises three concentric layers. Still further, at least one of the layers may comprise pulmonary ligament tissue or pulmonary visceral pleura tissue and, optionally, one of the additional layers may comprise a tissue or material other than pulmonary visceral pleura. For example, at least the inner-most layer may comprise visceral pleura and, in at least one embodiment, a luminal surface of the inner-most layer comprises mesothelium.

In at least one exemplary embodiment of a luminal graft of the present disclosure, the graft comprises at least one layer formed into a generally tubular element that may or may not be flexible. The tubular element has a proximal end, a distal end and a lumen extending therebetween, and is configured so that passage of plasma and blood cells into or through the lumen is permitted. Furthermore, in at least one embodiment the layer comprises a biological tissue comprising elastin and collagen fibers, where the elastin fibers are the dominant component thereof. Additionally or alternatively, the biological tissue may comprise between about 11% and about 12% collagen fibers and between about 12.5% and 13.5% elastin fibers. Still further, the biological tissue may exhibit mechanical properties that are similar pre- and post-fixation. In at least one exemplary embodiment, at least one of the layers comprises a biological tissue such as pulmonary ligament tissue and/or visceral pleura. Accordingly, the tubular element of the luminal graft may comprise in inner wall (i.e. a luminal surface) having mesothelium thereon. Additionally, in another exemplary embodiment, the lumen of the tubular element comprises a diameter that is equal to or less than about 5 mm. In addition to a layer of biological tissue, at least one of the additional layer(s) of the graft may comprise a synthetic material.

In another embodiment, each layer of the luminal graft comprises a first edge and a second edge. Both the first and second edges extend between the proximal and distal ends of the layer. Furthermore, the luminal graft further comprises a seam extending between the proximal and distal ends of the layer, the seam comprising the first and second edges sealed together via one or more closure mechanisms. The closure mechanism(s) may comprise an arrow-lock configuration, magnetic strips, a series of perforations and sutures, and/or a series of clips.

In at least one embodiment, the at least one layer of the graft comprises three concentric layers. There, the seam of each of the three concentric layers may be offset from the seam of each of the immediately adjacent layer(s). Further, in at least one embodiment, the offset comprises about a ninety degree angle.

In at least one embodiment of a system for the manufacture of a luminal graft, the system comprises a mandrel having a cylindrical configuration and at least one diameter, at least one layer comprising a length, and at least one closure mechanism configured to couple with the layer to form a seam along the length of the layer. Here, when the layer is positioned around the mandrel, a generally tubular element having at least one diameter that is substantially equivalent to the at least one diameter of the mandrel is formed. For example, and without limitation, the first diameter of the mandrel may comprise less than or equal to about 5 mm. Furthermore, at least one layer of the system may comprise at least three layers and, in at least one exemplary embodiment, at least one of the layers comprises pulmonary ligament tissue and/or visceral pleura oriented such that mesothelium faces the lumen of the tubular element.

In at least one exemplary embodiment of a method for manufacturing a luminal graft of the present disclosure, the method comprises the steps of (a) wrapping a first layer around a mandrel having at least one diameter; (b) positioning a closure mechanism coupled with the first layer for deployment; (c) engaging and/or deploying the closure mechanism, thereby forming a seam along a length of the first layer and defining a generally tubular element having at least one diameter that is substantially equal to the at least one diameter of the mandrel; (d) minimizing the profile of the seam; and (e) withdrawing the mandrel from the first layer. Where the luminal graft comprises more than one layer, the method for manufacturing the same may further comprise repeating steps (a)-(d) for the additional layers as necessary. Furthermore, the method may further comprise the step of ensuring a surface of the first layer comprising mesothelium is positioned facing the mandrel.

Methods for performing a luminal grafting procedure are also disclosed. In at least one embodiment, the method comprises the steps of: implanting a luminal graft within a mammalian body at a location of an arterial anastomosis, the luminal graft comprising at least one layer formed into a generally tubular element having a proximal end, a distal end and a lumen extending therebetween and configured such that passage of plasma and/or blood cells into or through the lumen is permitted, and wherein at least one of the layers comprises biological tissue comprising elastin and collagen fibers, with elastin being a dominant component thereof; providing at least an initial barrier between endothelial and smooth muscle cells of the artery using the luminal graft; and facilitating a remodeling process such that the smooth muscle cells of the artery integrate into the luminal graft. For example, the luminal graft may be configured to remodel pursuant to a physiological remodeling process of the mammalian body.

The biological tissue of the luminal graft used in the method of the present disclosure may comprise pulmonary ligament tissue and/or visceral pleura. Further, each of the layers of the luminal graft may comprise a first edge and a second edge, both of which extend between the proximal and distal ends of the layer. Additionally, a seam may extend between the proximal and distal ends of the layer, such seam comprising the first and second edges sealed together via one or more closure mechanisms.

In at least one alternative embodiment, the anastomosed artery comprises a small-diameter vessel and the lumen of the luminal graft comprises at least one diameter that is equal to or less than about 5 mm. In yet another embodiment, the lumen of the luminal graft comprises at least one diameter that is equal to or less than about 1 mm.

In additional embodiments of the method for performing a luminal grafting procedure, at least one of the layers of the luminal graft comprises a synthetic material, the tubular element of the luminal graft may further comprises a luminal surface having mesothelium thereon, at least one closure mechanism of the luminal graft may further comprise one or more sutures and/or the at least one closure mechanism of the luminal graft may comprise an arrow-lock configuration, magnetic strips, a series of perforations and sutures, and/or a series of clips.

In at least one exemplary embodiment of a luminal graft of the present disclosure, the luminal graft comprises at least an inner layer formed into a generally tubular element having a proximal end, a distal end, and a lumen extending therebetween. The inner layer of the luminal graft comprises biological tissue and additionally has a luminal surface having mesothelium thereon. In at least one alternative embodiment, the luminal graft additionally comprises at least one additional layer positioned concentrically around the inner layer.

In at least one embodiment, the biological tissue comprises elastin and collagen fibers, with elastin being a dominant component. In at least one embodiment, the biological tissue used for the luminal graft may comprise pulmonary pleura, parietal pleura, pleura ligament tissue, and mediastinal pleura, or a combination thereof.

In yet another embodiment, the lumen of the tubular element comprises at least one diameter that is equal to or less than about 4 mm (i.e. a small-diameter graft). The tubular element of the graft may be flexible and, in at least one embodiment, the luminal surface of the inner layer is capable of attenuating the growth of scar tissue and exhibits anti-thrombotic and anti-adhesive properties. Additionally, the tubular element of the luminal graft is capable of arterialization.

In certain embodiments, the luminal graft may comprise a cell guidance conduit and each of the proximal and distal ends of the tubular element may be configured to receive a nerve stump. Alternatively, in other embodiments, the luminal graft may comprise an arteriovenous graft. There, the proximal end of the tubular element may be configured to receive blood flow into the lumen from an artery, the distal end of the tubular element may be configured for placement into a vein, and the lumen of the tubular element may be configured for passage of blood from the proximal end to the distal end.

In at least one exemplary embodiment of a method for promoting regeneration of a damaged nerve, the method comprises the steps of: (a) providing a luminal graft comprising an inner layer formed into a generally tubular element having a proximal end, a distal end, and a lumen extending therebetween, wherein the inner layer comprises biological tissue and a luminal surface having mesothelium thereon; and (b) placing the luminal graft at a site of neuronal injury to facilitate regeneration of the nerve. In certain embodiments of the aforementioned method, the biological tissue of the inner layer comprises elastin and collagen fibers, with elastin being a dominant component thereof. Furthermore, the biological tissue may be selected from a group consisting of pulmonary pleura, parietal pleura, pleura ligament tissue, and mediastinal pleura, or comprise any combination thereof (where, for example, the luminal graft comprises multiple layers). In certain embodiments, the method of the present application may further comprise the step of maintaining patency of the tubular element for at least 6 months such that the nerve is allowed to regenerate within the lumen thereof.

In additional embodiments of the method, the lumen of the tubular element comprises at least one diameter that is equal to or less than about 4 mm. Additionally or alternatively, the tubular element may be flexible and the luminal surface of the inner layer may be capable of attenuating the growth of scar tissue and exhibits anti-thrombotic and anti-adhesive properties. In yet another exemplary embodiment, the nerve of the method is a mammalian peripheral nerve. Furthermore, in certain cases where the nerve is severed and comprises a first severed end and a second severed end, the method may further comprise the steps of: (c) bringing the first severed end of the nerve into contact with the proximal end of the tubular element; and (d) bringing the second severed end of the nerve into contact with the distal end of the tubular element so as to bridge the neuronal injury such that the lumen of the tubular element is substantially collinear with the first and second severed ends of the nerve. Additionally, in at least one embodiment stemming from the aforementioned, the ends of the severed nerve are sutured to each respective end of the tubular element.

In yet another exemplary embodiment of the present disclosure, a method for providing vascular access in connection with the delivery of hemodialysis to a patient is provided. In at least one embodiment, the method for providing vascular access in connection with the delivery of hemodialysis to a patient comprises the steps of: (a) providing a luminal graft comprising an inner layer formed into a generally tubular element having a proximal end, a distal end, and a lumen extending therebetween, and wherein the inner layer comprises biological tissue and a luminal surface having mesothelium thereon and at least the inner layer is capable of arterialization; (b) implanting the luminal graft in a patient to achieve vascular access such that the luminal graft connects an artery of the patient to a vein of the patient; (c) establishing blood flow from the artery to the vein through the lumen of the tubular element; and (d) allowing at least the inner layer to arterialize over time while being subjected to continuous blood flow through the lumen of the tubular element. Additionally, the method may comprise the additional steps of: (i) inserting the distal end of the tubular element of the luminal graft through an incision into the vein such that the distal end of the tubular element passes to a point downstream of the incision; (ii) surgically securing the luminal graft to the vein; (iii) anastomosing the proximal end of the tubular element to a preselected artery such that blood flow is established through the lumen of the tubular element, the blood flow entering the lumen through the proximal end of the tubular element and exiting the lumen through the distal end of the tubular element; and (iv) allowing at least the inner layer to arterialize over time. Moreover, in at least one embodiment, the method may further comprise the step of maintaining patency of the tubular element for at least 6 months while subjecting the luminal graft to continuous blood flow therethrough.

The present disclosure includes disclosure of a luminal graft comprising a generally tubular element configured for nerve cells to grow therethrough, the luminal graft comprising:

at least one sheet of biological tissue having elastin fibers and collagen fibers, with the elastin fibers being a dominant component thereof; and a plurality of microchannels formed on a surface of the at least one sheet of biological tissue, each of the microchannels extending longitudinally between a first end and a second end of the at least one sheet of biological tissue and configured to provide intraluminal structural guidance to nerve cells proliferating therethrough.

The present disclosure includes disclosure of a luminal graft, wherein the biological tissue comprises pulmonary ligament tissue or visceral pleura tissue.

The present disclosure includes disclosure of a luminal graft, further comprising a plurality of biodegradable microspheres affixed to the surface of the at least one sheet of biological tissue and positioned in rows extending longitudinally between the first end and the second end of the at least one sheet of biological tissue, wherein the rows of microspheres define side portions of the plurality of microchannels.

The present disclosure includes disclosure of a luminal graft, wherein each of the biodegradable microspheres encapsulates a substance and, when the biodegradable microsphere degrades, the substance is released therefrom.

The present disclosure includes disclosure of a luminal graft, wherein the substance comprises a neurotrophic factor.

The present disclosure includes disclosure of a luminal graft, wherein the plurality of biodegradable microspheres further comprises a first set of biodegradable microspheres encapsulating a first neurotrophic factor and a second set of biodegradable microspheres encapsulating a second neurotrophic factor.

The present disclosure includes disclosure of a luminal graft, wherein the first neurotrophic factor comprises NGF and the second neurotrophic factor comprises NT-3.

The present disclosure includes disclosure of a luminal graft, wherein the plurality of biodegradable microspheres further comprises a first set of biodegradable microspheres that have a first rate of degradation and a second set of biodegradable microspheres that have a second rate of degradation; wherein the first rate of degradation is faster than the second rate of degradation.

The present disclosure includes disclosure of a luminal graft, wherein the first set of biodegradable microspheres is positioned at or near the first and second ends of the at least one sheet of biological tissue and the second set of biodegradable microspheres is positioned in a middle portion of the at least one sheet of biological tissue.

The present disclosure includes disclosure of a luminal graft, wherein the at least one sheet of biological tissue is arranged to form cylinder comprising a plurality of internal layers, each layer comprising a plurality of biodegradable microspheres positioned in rows extending longitudinally between the first end and the second end of the sheet, wherein the rows of microspheres define side portions of the plurality of microchannels.

The present disclosure includes disclosure of a grating module for fabricating a luminal graft comprising a plurality of microspheres, the grating module comprising a series of notches, each notch separated by an interval and comprising a depth and a width, wherein the depth is about 20% smaller than the width.

The present disclosure includes disclosure of a grating module, wherein each notch comprises a length of 6 cm, the width of each notch is selected from the group consisting of 100 μm, 200 μm, and 400 μm, and the depth of each notch is selected from the group consisting of 80 μm, 160 μm, and 320 μm, respectively.

The present disclosure includes disclosure of a method for performing a luminal grafting procedure, the method comprising the steps of implanting a luminal graft within a mammalian body at a location of a proximal nerve stump and a distal nerve stump, the luminal graft comprising at least one sheet of biological tissue having elastin fibers and collagen fibers, with the elastin fibers being a dominant component thereof, a plurality of microchannels formed on a surface of the at least one sheet of biological tissue, each of the microchannels extending longitudinally between a first end and a second end of the at least one sheet of biological tissue and configured to provide intraluminal structural guidance to nerve cells proliferating therethrough, and a plurality of biodegradable microspheres affixed to the surface of the at least one sheet of biological tissue and positioned in rows extending longitudinally between the first end and the second end of the at least one sheet of biological tissue, wherein the rows of microspheres define side portions of the plurality of microchannels and each of the microspheres encapsulates a neurotrophic factor, wherein the at least one sheet of biological tissue is arranged into a cylindrical configuration such that the plurality of microchannels comprise a ceiling and a floor formed from the at least one sheet of biological tissue.

The present disclosure includes disclosure of a method, further comprising the steps of releasing a first set of neurotrophic factors from a first set of the microspheres to facilitate nerve proliferation at or near the first end and the second end of the at least one sheet of biological tissue; and releasing a second set of neurotrophic factors from a second set of the microspheres to facilitate nerve proliferation in a middle portion of the at least one sheet of biological tissue.

The present disclosure includes disclosure of a method, wherein the step of releasing a first set of neurotrophic factors occurs at a first time and the step of releasing a second set of neurotrophic factors occurs at a second time, the second time occurring after the first time.

The present disclosure includes disclosure of a hybrid luminal graft comprising a generally tubular element, the luminal graft comprising a first layer comprising one or more synthetic materials, the first layer defining an inner surface and an opposing outer surface; and a biological material applied to the inner surface of the first layer; wherein when the first layer is configured as a generally tubular element, the biological material is present within a defined lumen of the first layer.

The present disclosure includes disclosure of a hybrid luminal graft, wherein the synthetic material is selected from the group consisting of silicone, polytetrafluoroethylene, and elastomer.

The present disclosure includes disclosure of a hybrid luminal graft, wherein the biological material is selected from the group consisting of pulmonary visceral pleura, pulmonary ligament, a component harvested from pulmonary visceral pleura, and a component harvested from pulmonary ligament.

The present disclosure includes disclosure of a hybrid luminal graft, wherein a biological glue is used to facilitate adherence of the biological material to the inner surface.

The present disclosure includes disclosure of a hybrid luminal graft, wherein the biological material comprises glycocalyx.

The present disclosure includes disclosure of a hybrid luminal graft, further comprising a second layer comprising one or more synthetic materials, the second layer positioned around a relative outside of the first layer.

The present disclosure includes disclosure of a hybrid luminal graft, further comprising a third layer comprising one or more synthetic materials, the third layer positioned around a relative outside of the second layer.

BRIEF DESCRIPTION OF THE DRAWINGS

FIGS. 4A and 5B show an embodiment of a magnetic closure mechanism of a luminal graft according to the present disclosure;

FIGS. 5A and 5B show an embodiment of a perforated closure mechanism of a luminal graft according to the present disclosure;

Figure 10A:
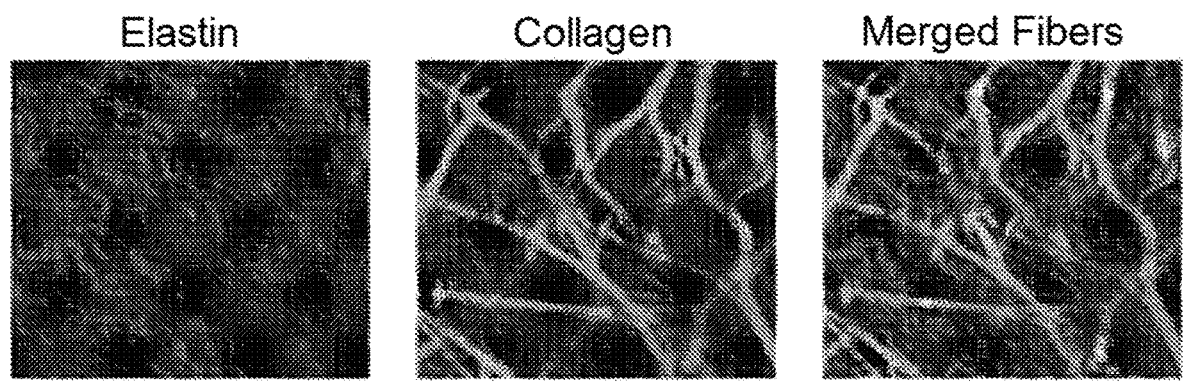
FIG. 10A shows two-photon microscopy and fluorescent images of the ultrastructure of a pulmonary visceral pleura tissue sample, with elastin fiber (left), collagen fibers (middle), and merged images (right)
Figure 10B:
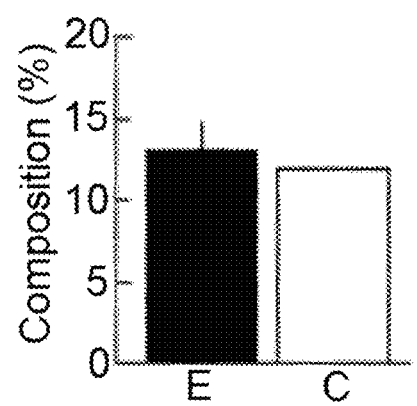
FIG. 10B shows a graphical representation of the elastin fiber (E, n=10) and collagen fiber (C, n=10) content of pulmonary visceral pleura tissue.
Figure 10C:
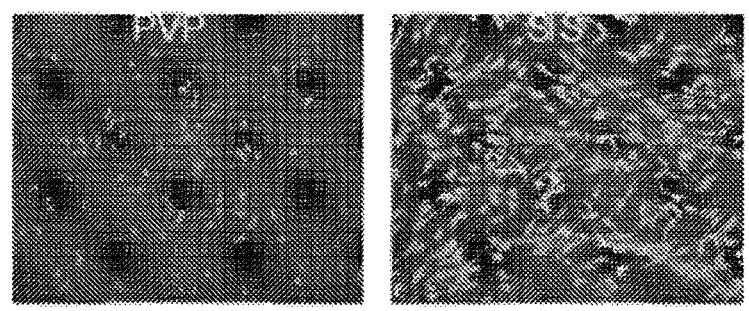
FIG. 10C shows representative images of fibroblast attachment to pulmonary visceral pleura tissue (PVP, left)
Figure 10D:
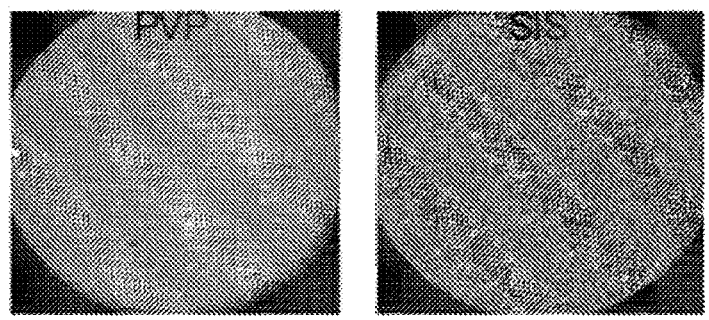
Figure 11A:
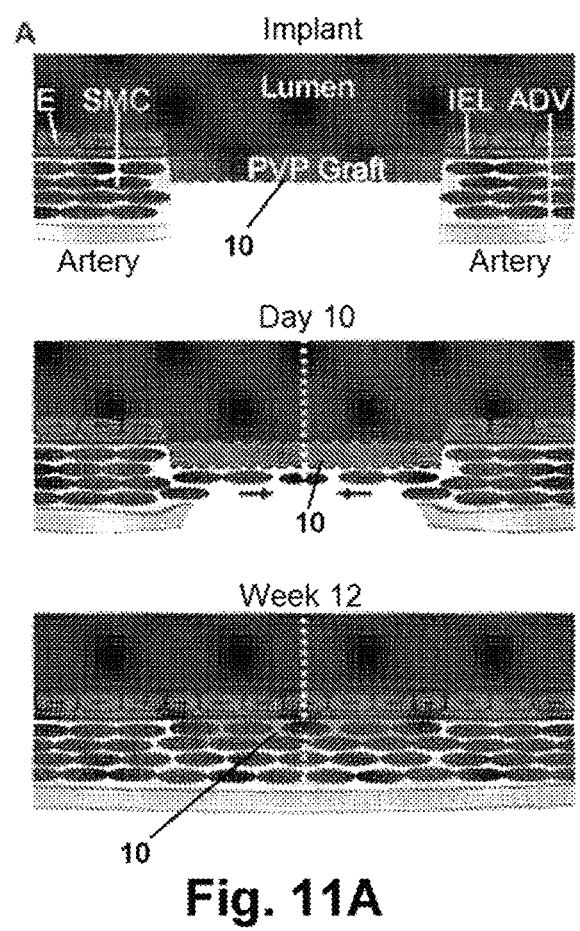
Figure 11B:
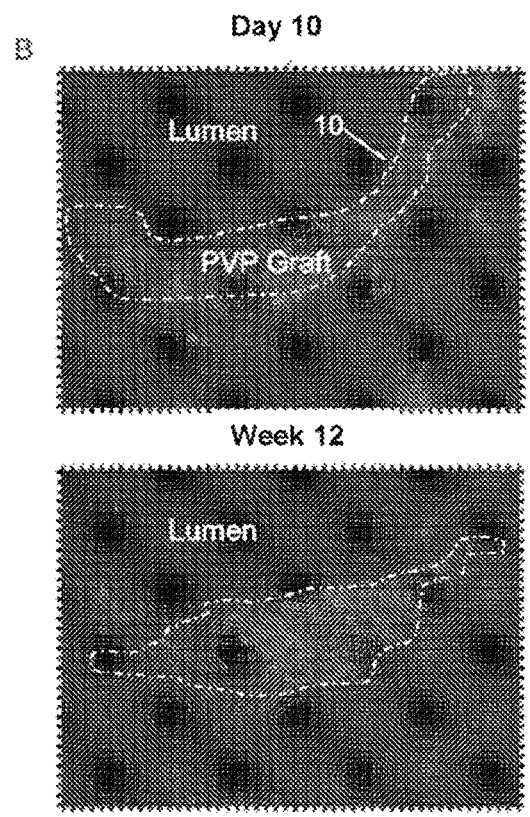
Figure 12A:
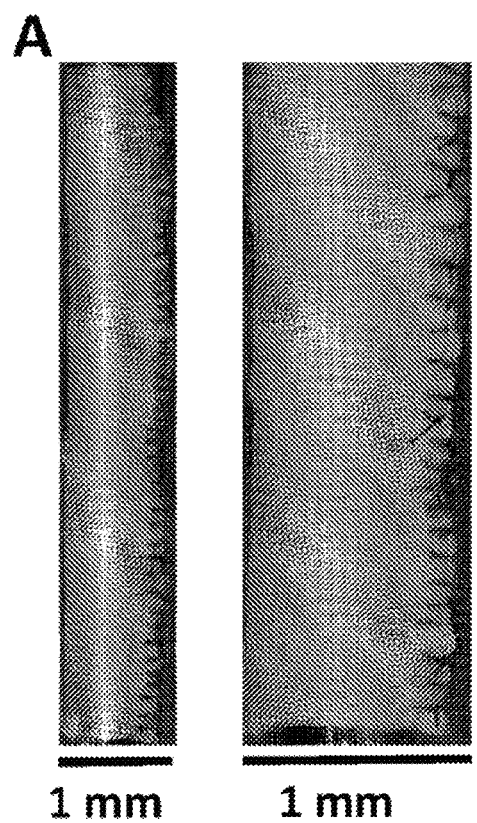
Figure 12B:
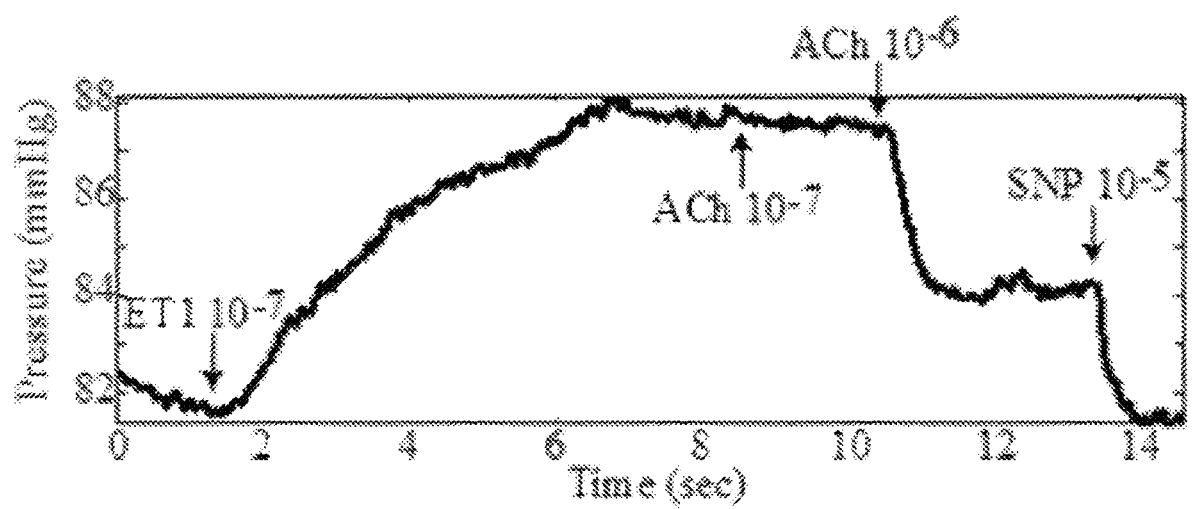

and small intestine submucosa (SIS, right), and highlights reduced fibroblast adhesion to pulmonary visceral pleura as compared to small intestine submucosa;

FIG. 10D shows representative images of pulmonary visceral pleura (PVP) and small intestine submucosa (SIS) that illustrates reduced cytotoxicity of PVP as compared to SIS;

FIG. 11A shows a schematic of in vivo remodeling of a pulmonary visceral pleura graft (E—endothelial cells, SMC—smooth muscle cells, IEL—internal elastic lamina, ADV—adventitia);

FIG. 11B displays immunofluorescent images of a pulmonary visceral pleura graft cross-section at 10 days and 12 weeks in vivo (20× objective; Red-Elastin, Blue-Nuclei);

FIG. 12A shows a side view representing a 0.80 mm pulmonary visceral pleura (PVP) graft prior to implantation;

FIG. 12B shows a graphical representation of the functional response of the PVP graft of FIG. 12A to pharmacological vasodilation and constriction after 6 months of in vivo remodeling (Acetylcholine, ACh; Sodium Nitroprusside, SNP; Endothelin-1, ET1; concentrations in mol/L).

Figure 3A:
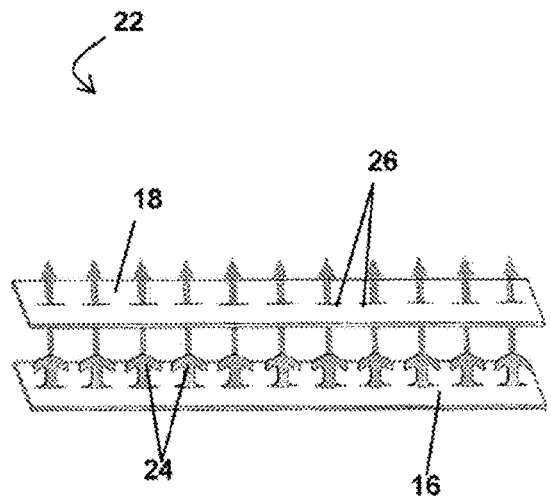
FIGS. 3A and 3B show an embodiment of an arrow-locking closure mechanism of a luminal graft according to the present disclosure.
Figure 14C:
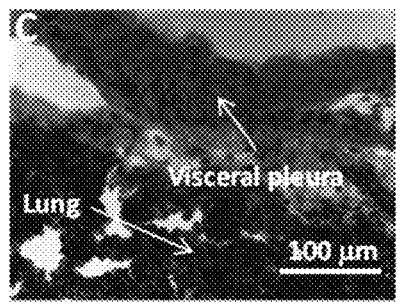
Figure 15A:
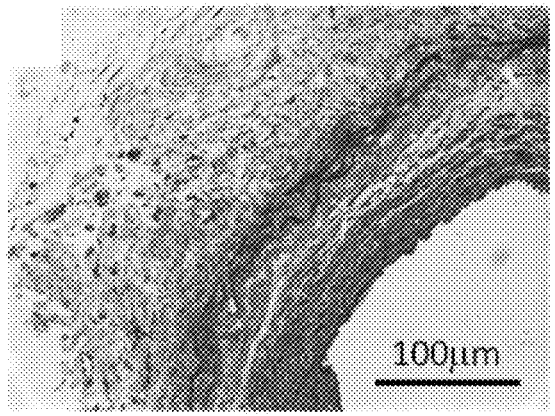
Figure 15B:
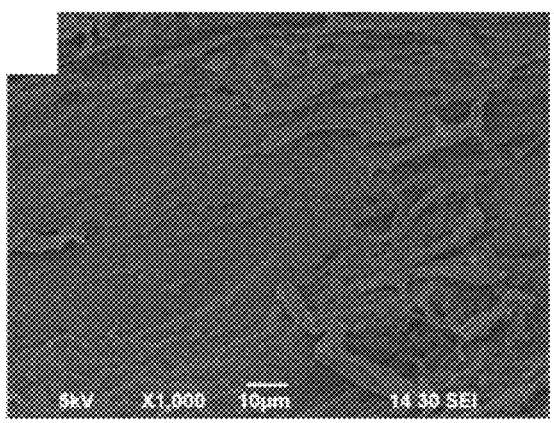
Figure 15C:
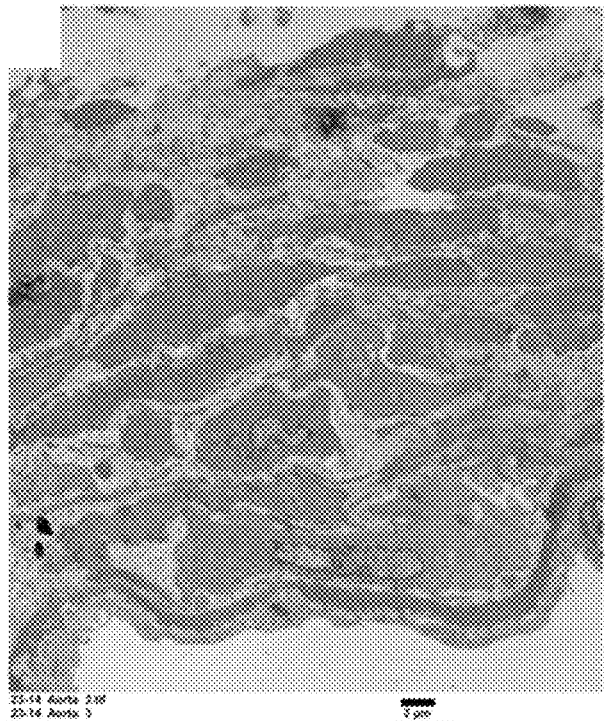
Figure 16A:
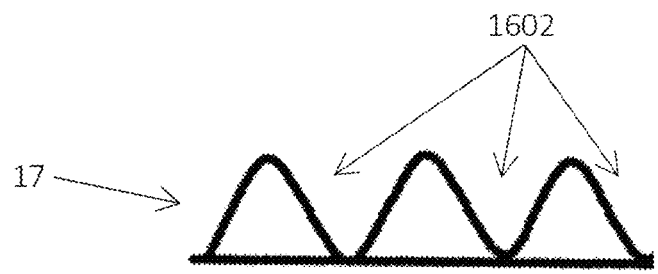
Figure 16B:
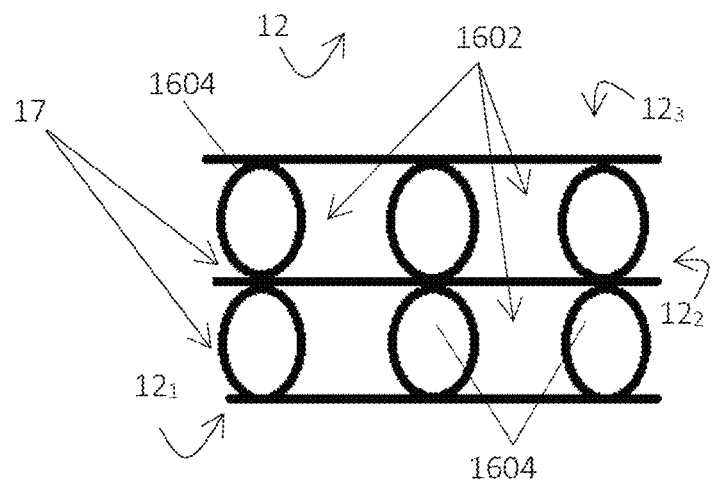
Figure 16C:
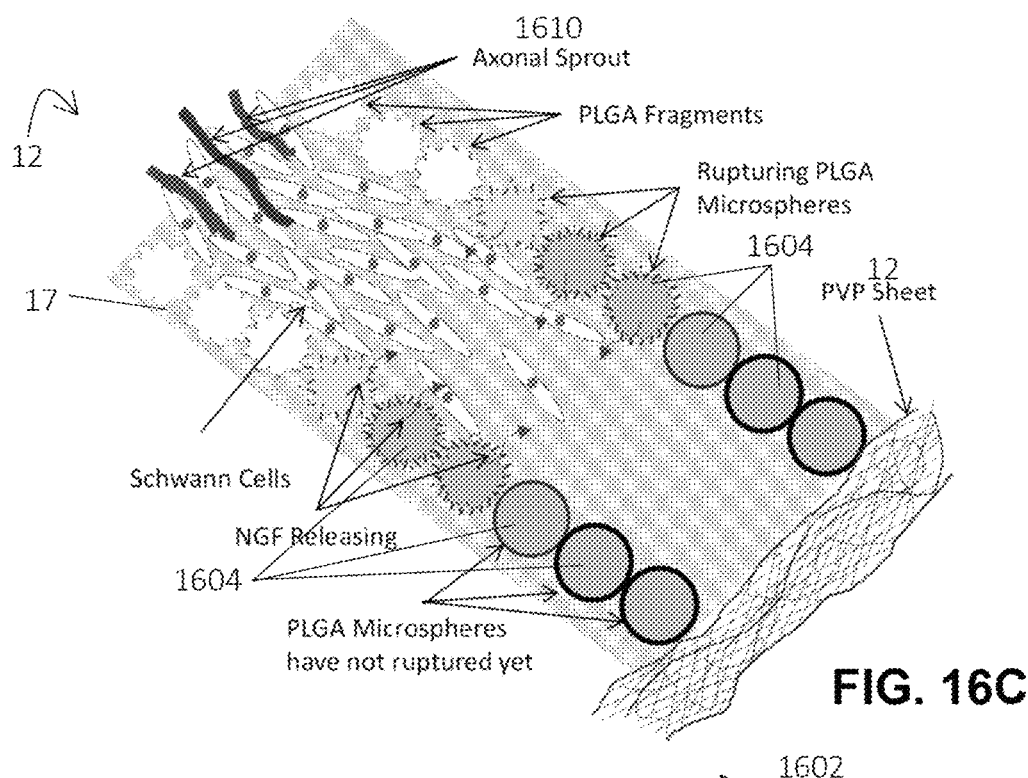
Figure 17:
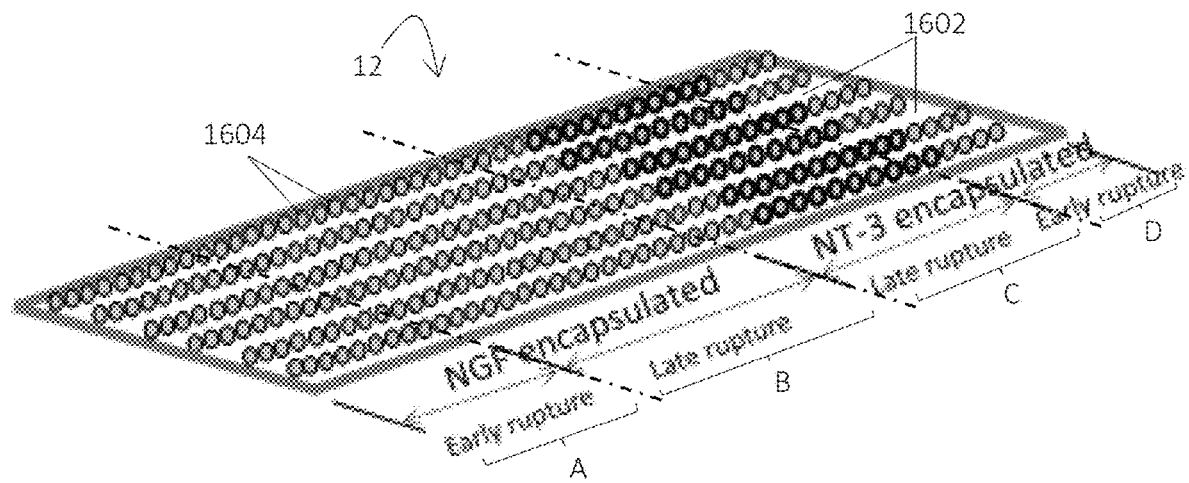
Figure 18:
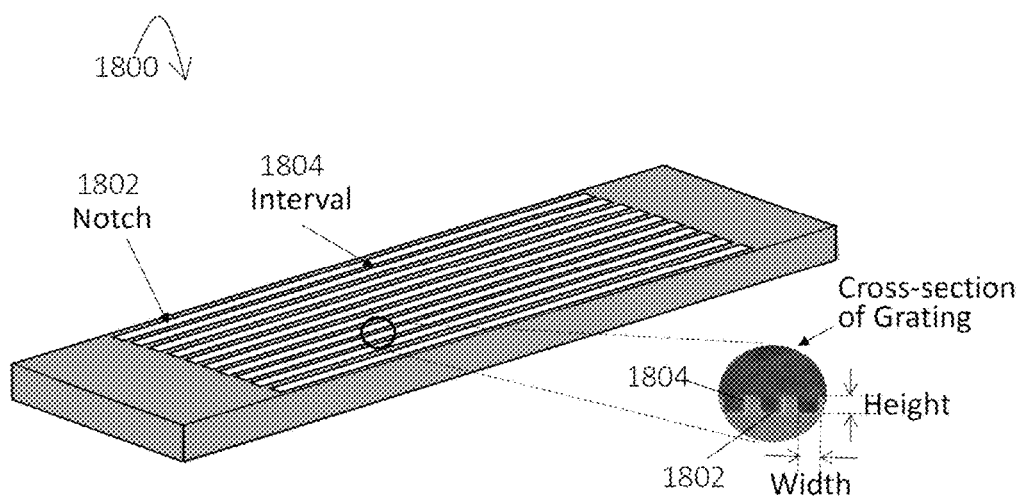
Figure 19:
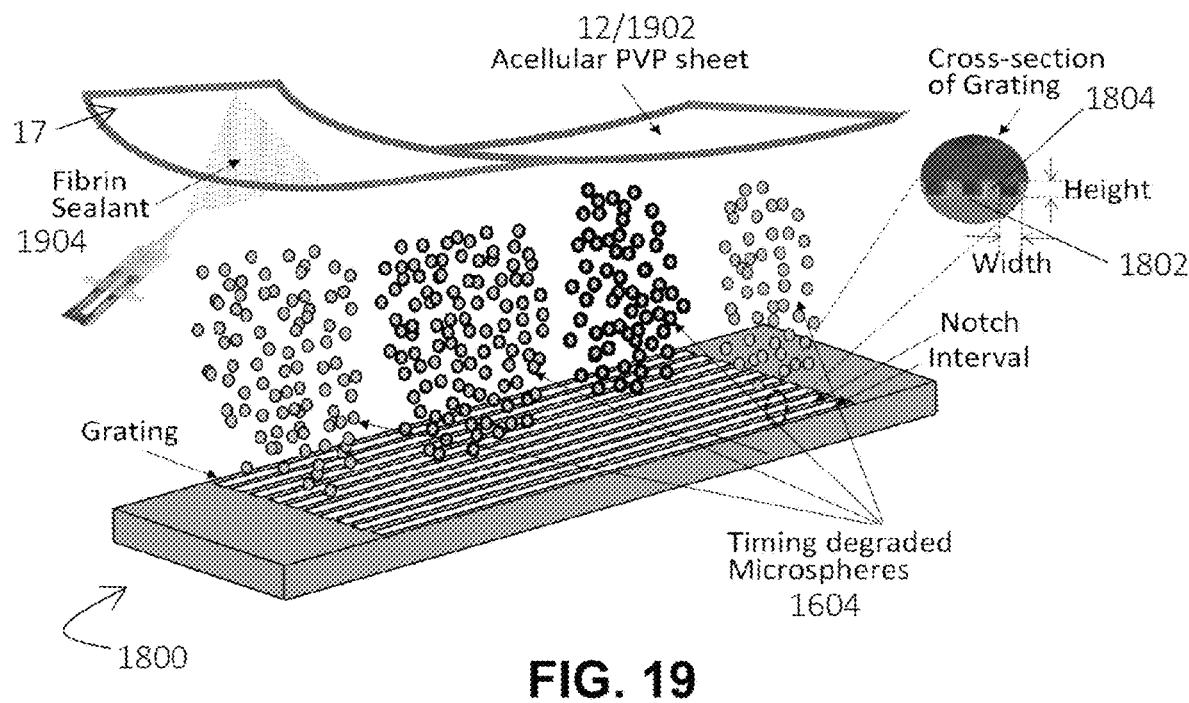
Figure 20:
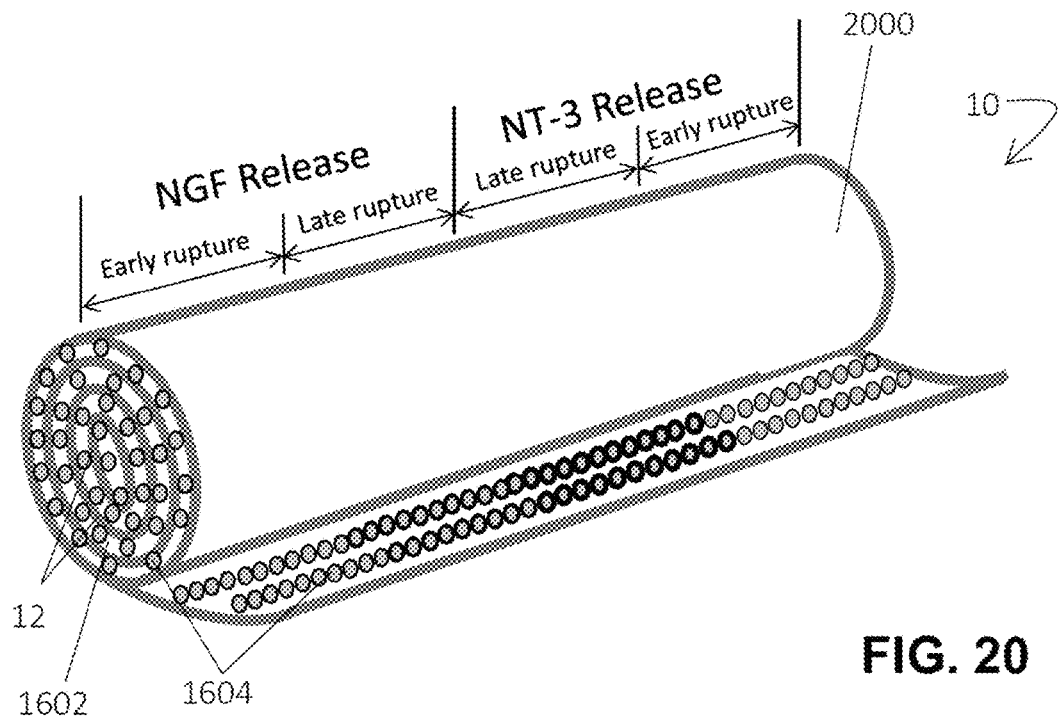
Figure 21A:
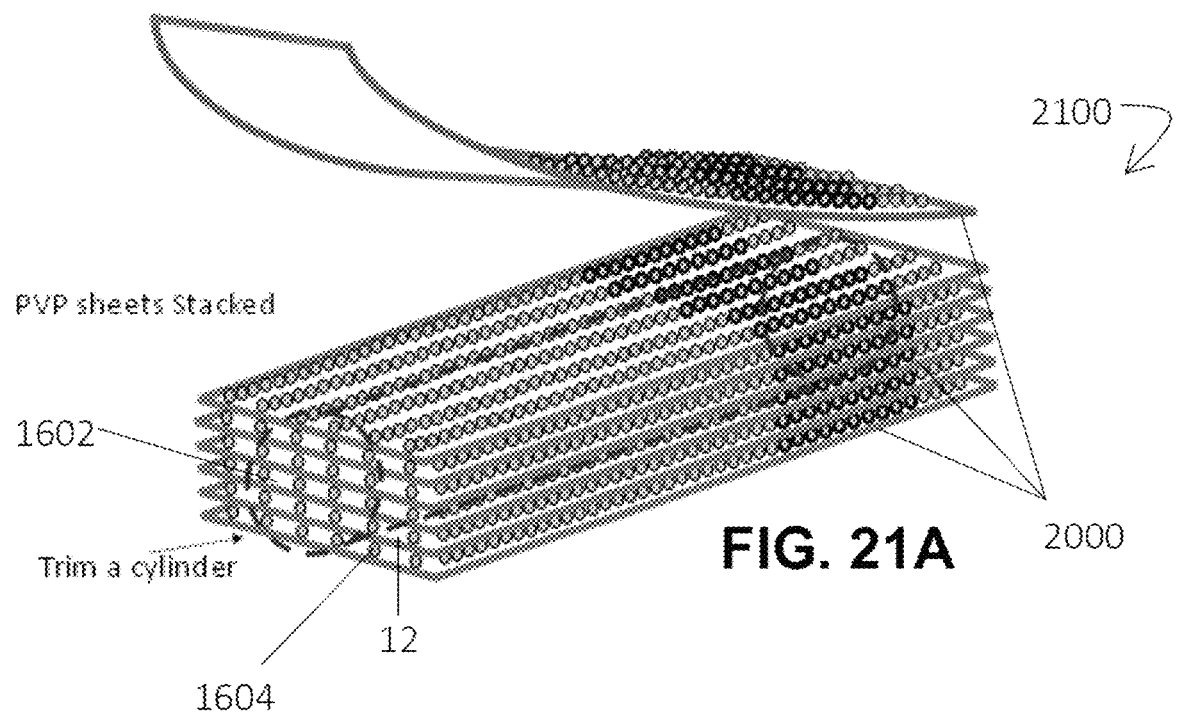
Figure 21B:
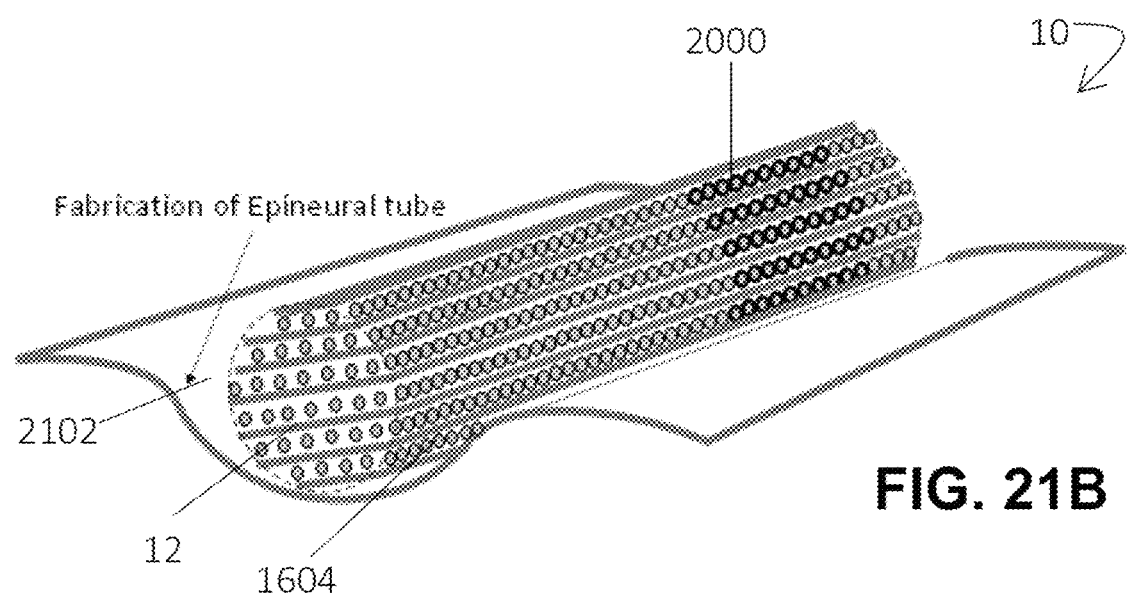

FIG. 13A shows a transmission electron microscope image of a cross-section of pulmonary pleura;

FIG. 13B shows a scanning electron microscope image of the pulmonary pleura shown in FIG. 3A;

FIGS. 14A and 14B show A) a luminal graft according to the present disclosure being used as a nerve guidance conduit, and B) the end of the nerve guidance conduit of FIG. 14B;

FIG. 14C shows a close-up view of a sample of pulmonary pleura in vivo;

FIGS. 15A, 15B, and 15C show histological images of a graft implanted in a femoral artery for 24 weeks, with FIG. 15A showing an optical image, FIG. 15B showing a transmission electronic microscopy image, and FIG. 15C showing a scanning electron microscopy image, according to the present disclosure;

FIGS. 16A and 16B show traverse cross-sectional views of a luminal graft according to the present disclosure comprising microchannels;

FIG. 16C shows a schematic of a microchannel of the luminal graft of FIG. 16B;

FIG. 17 shows a perspective view of a biological sheet of the present disclosure coated with microspheres to form microchannels within a luminal graft according to the present disclosure;

FIG. 18 shows a perspective view of a grating module for fabricating the luminal graft comprising microspheres according to the present disclosure;

FIG. 19 shows a perspective view of the grating module of FIG. 18 being used to coat the biological sheet of FIG. 17 with microspheres to form microchannels;

FIG. 20 shows a perspective view of a sheet coated with microspheres according to the present disclosure rolled up to form a cylindrical luminal graft;

FIGS. 21A and 21B show perspective views of the steps of a method for fabricating a multi-layered cylindrical luminal graft according to the present disclosure.

Figure 22:
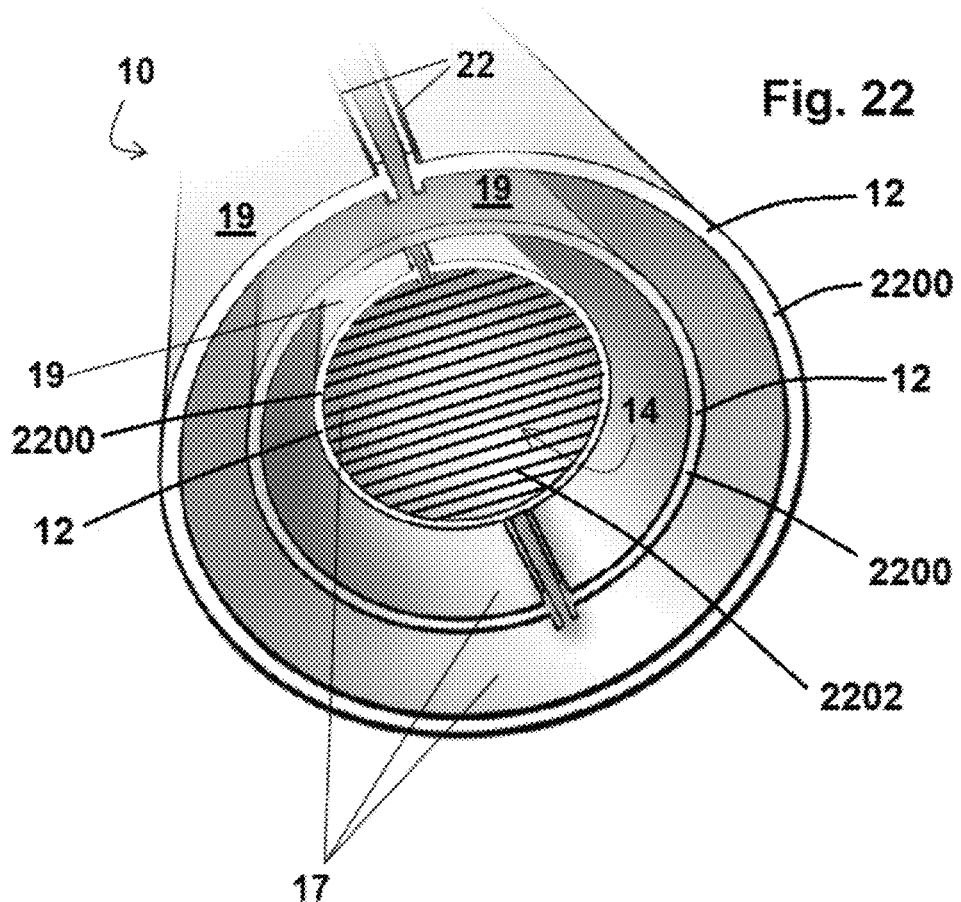
Figure 23:
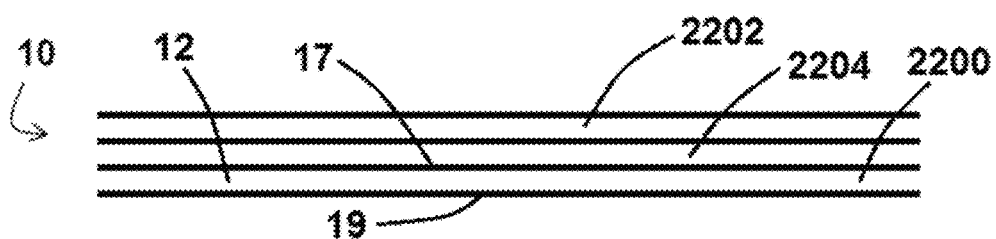
Figure 24:
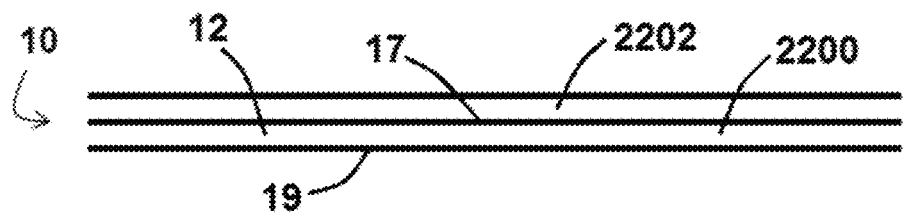
Figure 25:
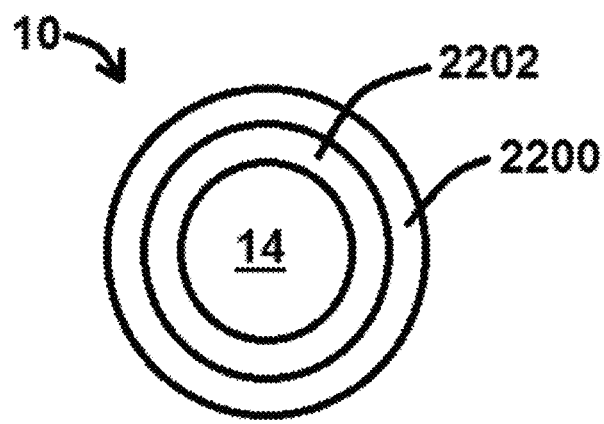
Figure 26:
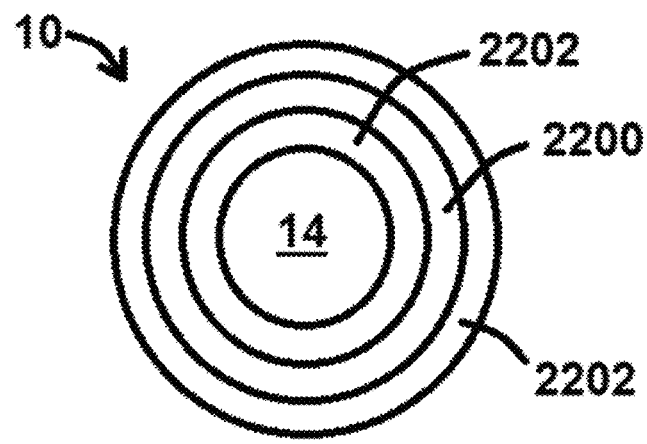
Figure 27:
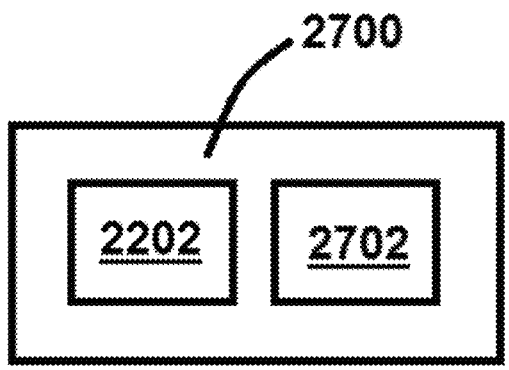

FIG. 22 shows a perspective, exploded view of a portion of an embodiment of a luminal graft having three layers;

FIGS. 23 and 24 show side views of elements of grafts prior to being configured as tubular elements, according to the present disclosure;

FIGS. 25 and 26 show grafts in tubular or cylindrical form, according to embodiments of the present disclosure; and FIG. 27 shows a block component diagram of elements of a mixture of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. On the contrary, this disclosure is intended to cover alternatives, modifications, and equivalents as may be included within the spirit and scope of this application as defined by the appended claims. As previously noted, while this technology may be illustrated and described in one or more preferred embodiments, the devices, systems and methods hereof may comprise many different configurations, forms, materials, and accessories.

For example, the novel systems, methods and techniques of the present application will be described in the context of replacing damaged or compromised blood vessels and engineering luminal grafts for various medical applications. Unlike conventional luminal grafts, the inventive grafts of this disclosure are capable of not only maintaining long term patency, but also arterializing over time. While the luminal grafts described herein may be prepared having any diameter, it will be appreciated that the inventive blood vessel grafts of this disclosure may be configured and functional for the replacement of small-diameter blood vessels. Indeed, the blood vessel grafts described herein do not experience the problems associated with small-diameter constructs prepared in accordance with conventional methods such as stenosis, aneurysm, or thrombosis formation. Furthermore, while the systems and methods described herein are suitable for preparing blood vessel grafts (exemplary luminal grafts of the present disclosure as useful in connection with blood vessels), having any diameter, such systems and methods are especially suited for preparing blood vessel grafts having at least a portion with a small diameter (e.g., less than or equal to about 5 mm). Additionally, it is contemplated that the inventive concepts underlying the grafts, systems and methods described herein may also be applied to other tissue engineering applications such as, and without limitation, venous valves, microvessels, nerve grafts, dura matter, and stent coverings. Indeed, certain embodiments of the present disclosure provide a novel nerve guidance conduit that is abundant in extracellular matrix (elastin, collagen, and glycocalyx) for providing chemical cues for regenerating axons, provides intraluminal microchannels for topographic guidance cues for regenerating axons, and allows for the spatial and/or temporal release of neurotrophic factors to further promote axonal regeneration. Importantly, such guidance conduits show significant promise in not only promoting axonal regeneration for shorter nerve injury gaps, but also in larger gaps as well.

Because of these unique and advantageous properties, and as will be described herein in further detail, the luminal grafts of the present disclosure are particularly well suited for use in, and are functional for, vascular replacement therapies (small-diameter and otherwise), anastomosis formation, tubulization or nerve regeneration therapies, and arteriovenous graft hemodialysis. Additionally, while the luminal grafts described herein may be prepared having any diameter, it will be appreciated that the inventive grafts of this disclosure may be configured and are functional for the replacement of small-diameter blood vessels (e.g., vasculature having at least a portion with a diameter of less than or equal to about 4 mm) or for use as small-diameter conduits (e.g., conduits having at least a portion with a diameter of less than or equal to about 4 mm). Likewise, the systems and methods described herein are suitable for preparing grafts and conduits having any diameter, including but not limited to those grafts and conduits having at least a portion with a small diameter (e.g., less than or equal to about 4 mm).

In the following description, numerous specific details are set forth in order to provide a thorough understanding of the present disclosure. Particular examples may be implemented without some or all of these specific details. In other instances, well known harvesting, processing, and storing operations have not been described in detail so as to not unnecessarily obscure the present disclosure.

Various techniques and mechanisms of the present disclosure will sometimes describe a connection between two components. Words such as attached, affixed, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. For example, a closure mechanism may be connected to a graft, but it will be appreciated that one or more components may reside between the actual graft layer and the closure mechanism. Consequently, a connection does not necessarily mean a direct, unimpeded connection unless otherwise noted.

Furthermore, wherever feasible and convenient, like reference numerals are used in the figures and the description to refer to the same or like parts or steps. The drawings are in a simplified form and not to precise scale. For example, the disclosure and Figures of the present application for the most part reference the inventive luminal grafts described herein as having a single diameter or as being "small-diameter blood vessels." It is understood that the disclosure is presented in this manner merely for explanatory purposes and the principles and embodiments described herein may be applied to grafts that have varying diameters along their lengths (as well as the systems and methods for manufacturing the same). For example, the disclosure hereof may be applied to luminal grafts that are longer than about 30 mm in length and configured to have a varying diameter so as to more accurately mimic a native blood vessel (i.e. the distal diameter may be smaller than the proximal diameter). In fact, as described herein, the use of pulmonary ligament tissue, visceral pleura, and/or mediastinal pleura in the composition of a varying diameter luminal graft can have a particularly advantageous effect, especially where the smallest diameter thereof is less than or equal to about four millimeters (≤4 mm) or is less than or equal to about five millimeters (≤5 mm)

Figure 1:
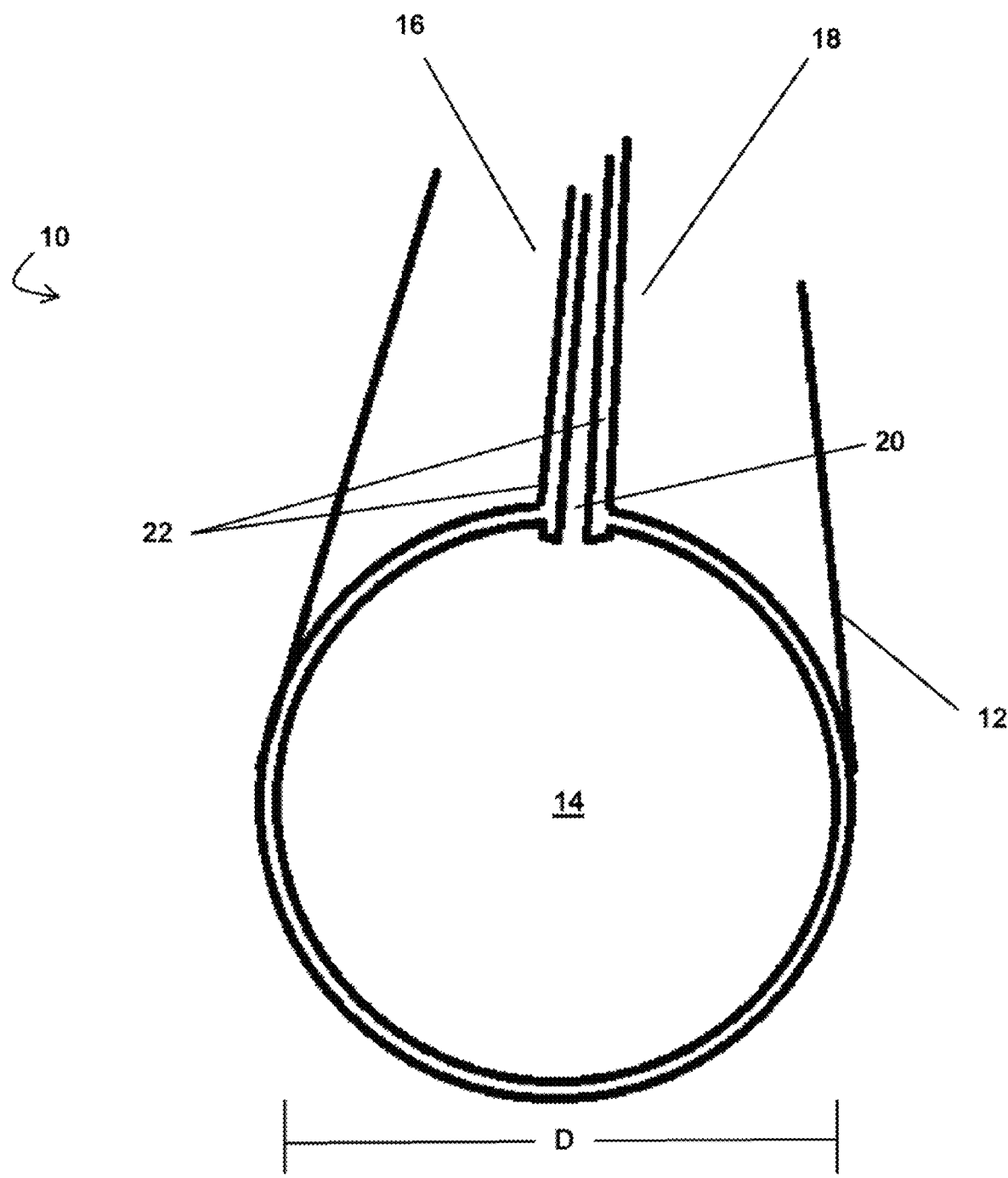
FIG. 1 shows a perspective view of a portion of an exemplary embodiment of a luminal graft suitable for the replacement of small-diameter vessels according to the present disclosure.

FIG. 1 shows a perspective view of at least one embodiment of an exemplary luminal graft 10. Luminal graft 10 comprises a tubular construct having a diameter D and one or more concentric layers 12. Diameter D (also considered to be a perimeter in the event luminal graft 10 is not absolutely circular in cross-section) of the graft 10 may comprise any diameter of a vessel in need of replacement or of a desired conduit, but in at least one exemplary embodiment, diameter D is less than or equal to about four or five millimeters (≤4 or ≤5 mm). For example, in at least one exemplary embodiment, diameter D of the graft 10 may be/comprise three millimeters or less than about three millimeters (≤3 mm) or even may be/comprise eight tenths of a millimeter or less than about eight tenths of a millimeter (≤0.8 mm).

Figure 2A:
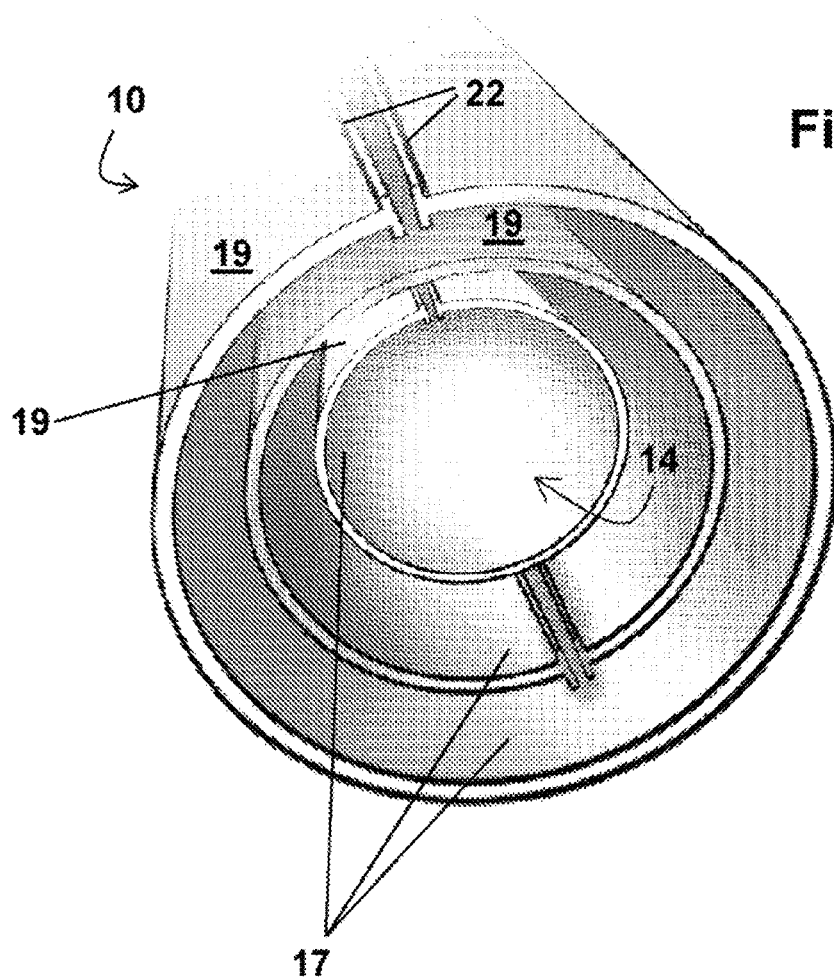
FIG. 2A shows a perspective, exploded view of a portion of an embodiment of a luminal graft having three layers.

Each of the one or more layers 12 of the graft 10 comprises a first edge 16 and a second edge 18, as shown in FIG. 1, and an inner surface 17 and an outer surface 19, as shown in FIG. 2. The layer 12 is shaped to define a lumen 14 extending the length thereof, where the first and second edges 16, 18 are positioned proximally to each other, the inner surface 17 faces the lumen 14, and the outer surface 19 faces outwardly. The first edge 16 and the second edge 18 are securely sealed together via one or more closure mechanisms 22 to form a seam 20 extending the length of the luminal graft 10.

In the exemplary embodiment shown in FIG. 1, luminal graft 10 comprises one layer 12; however, luminal graft 10 may comprise any number of concentric layers 12 wrapped around each other. For example, and without limitation, FIG. 2 illustrates at least one embodiment of the luminal graft 10 having three layers 12 (it will be understood that FIG. 2 illustrates an exploded view of the luminal graft 10 to clearly illustrate the various layers 12; in actuality, such layers 12 are in contact with each other and wrapped tightly together). The number of layers 12 and/or dimensions of the luminal graft 10 may be selected depending upon the desired wall thickness of the luminal graft 10 or pursuant to a particular application or patient specifications. For example, where a graft 10 having a thicker wall is desired (such as for replacement of a portion of a larger vessel), the luminal graft 10 may comprise multiple layers 12. Alternatively, where a thinner wall is more appropriate, the graft 10 may comprise fewer layers 12. The thickness of each individual layer 12 may also be selected to achieve a desired overall wall thickness of the graft 10 and/or to affect the properties thereof (by way of a non-limiting example, the inner-most layer 12 may be thicker than the outer-most layer 12). In this manner, in application, the overall wall thickness of the luminal graft 10 can be matched to the native blood vessel or nerve of interest, for example, such that the ratio of wall thickness to diameter is nearly constant (e.g., thickness may be about ten percent (10%) of graft 10 diameter at any given point and assuming about a +/−20% acceptable variance range between the graft and native blood vessel). In the case of nerve conduit, thickness may be at or about thirty percent (30%) of graft 10 diameter and the diameter of nerve conduit is at or about three to eight percent (3-8%) larger than native nerve to allow insertion if native nerve stump/end into the lumen of the nerve conduit.

Furthermore, where a luminal graft 10 comprises more than one layer 12, the layers 12 may be positioned relative to each other such that the seams 20 thereof are positioned in an offset configuration. For example and without limitation, in the embodiment shown in FIG. 2A, the seams 20 of the layers 12 are alternated at roughly one hundred and eighty degree (180°) angles to ensure an "air tight"—i.e. leak proof—construct. Additionally or alternatively, the seams 20 may be offset at other degrees as well, including ninety degrees (90°) or any degree of offset, or combinations thereof, that may be desired.

Figure 2B:
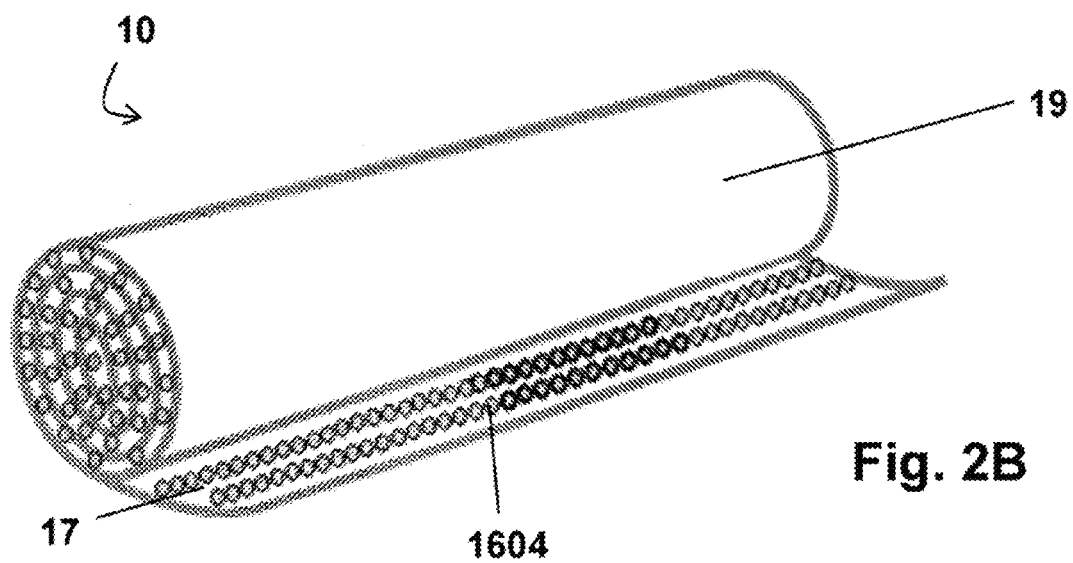
FIG. 2B shows a perspective view of an embodiment of a luminal graft of the present disclosure comprising a rolled configuration formed from a single sheet of tissue.

Other embodiments of the present disclosure contemplate a graft 10 comprising a single sheet of tissue that is simply rolled up to provide a multi-layered cylinder (see FIG. 2B). This rolled configuration minimizes the number of seams 20 within the luminal graft 10, while still providing a multi-layered structure.

In at least one exemplary embodiment of the present disclosure, the one or more layers 12 of luminal graft 10 are comprised of a thin scaffold of biological tissue that consists largely of elastin and some collagen fibers (the converse of small intestine submucosa (SIS)) (Conventional methodologies have previously evaluated fixed acellular biomaterials such as the pericardium and SIS as small-diameter vessel grafts. While both of these biomaterials showed promise as large diameter vessel grafts, neither remained patent as small-diameter vessel grafts and, as such, are not conventionally used in coronary artery bypass grafting surgery.). For example, and without limitation, the one or more layers 12 of luminal graft 10 may comprise pulmonary ligament tissue and/or visceral pleura, both of which exhibit characteristics that are conducive to forming a functional small-diameter blood vessel construct. The tissue used for the one or more layers 12 of the luminal graft 10 described herein may be derived from any organism, but preferably cells derived from vertebrates are used. More preferably, cells derived from mammals (e.g., primates, artiodactyls (such as swine and bovine), rodents, etc.) are used.

In at least one exemplary embodiment, the layer(s) 12 of a luminal graft 10 comprises glutaraldehyde-fixed pulmonary ligament tissue and/or visceral pleura. For example, and without limitation, in at least one embodiment, the one or more layers 12 of luminal graft 10 may comprise pleura tissue and/or pleura ligament tissue, which both exhibit characteristics that are conducive to forming a functional small-diameter luminal construct. The tissue used for the one or more layers 12 of the luminal graft 10 described herein may be derived from any organism, but preferably comprises cells derived from vertebrates. For the avoidance of doubt, as used herein, the term "pleura tissue" means and includes tissue from the visceral pleura, pulmonary pleura, parietal pleura and/or, more specifically, mediastinal pleura. Furthermore, the term "pleura ligament tissue" as used herein means and includes tissue from the pulmonary ligament.

For reference, a pleura is a serosa membrane that folds back onto itself to form a two-layered membrane structure. Generally, the outer pleura lines the thoracic cavity, whereas the inner pleura (visceral or pulmonary pleura) covers the lungs. The parietal pleura lines the inner surface of the chest wall, covers the superior surface of the diaphragm, and encases all of the thoracic viscera (excluding the lungs). Accordingly, the parietal pleura separates the pleural cavity (where the lungs are positioned) from the mediastinum or the "middle" section of the chest cavity.

The parietal pleura is divided into different portions according to its position. For example, the costal pleura is the portion of the parietal pleura that lines the inner surfaces of the ribs and intercostals, the diaphragmatic pleura is that which lines the convex surface of the diaphragm, and the cervical pleura is the portion that rises into the neck and over the apex of the lung. Furthermore, mediastinal pleura is the portion of parietal pleura that defines the mediastinum and encases all of the thoracic viscera except for the lungs, as it runs therebetween.

As the mediastinal pleura separates the right and left lungs, inflation of the lungs causes a corresponding expansion of the mediastinal membrane, thereby resulting in significant friction between the mediastinal pleura and the lungs' surfaces during breathing. While the mediastinal pleura is relatively thin, it nevertheless exhibits substantial integrity and elasticity to accommodate the lungs' expansion and tolerate the friction imposed thereby. The significant elasticity of the mediastinal tissue is indicative of its composition, which consists of multiple fiber-sheet layers having an abundance of elastin fibers in addition to the collagen typically present in connective tissue. This is significant from a tissue product and medical application perspective as, unlike collagen, elastin cannot be fixed and largely retains its elasticity and biomechanical activity post-fixation. Furthermore, both surfaces of the mediastinal pleura are lined with mesothelium, which provides for significant integrity, promotes its friction-resistant nature, and provides for antithrombotic properties. Accordingly, post fixation mediastinal pleura has high elasticity, and both sides of the mediastinal pleura tissue are smooth and covered with an epithelial layer that secrets a lubricant.

Visceral pleura plays an important physiologic role in lung function and is responsible for approximately twenty percent (20%) of the work done during deflation. It is inherently compliant and non-thrombogenic due, at least in part, to its mesothelial lining. In particular, visceral pleura (as well as the pulmonary ligament, which will be discussed in further detail below) comprises a smooth, continuous layer of mesothelial cells, which perform a significant role in maintaining homeostasis akin to vascular endothelial cells. Furthermore, the pulmonary visceral pleura has an extracellular composition that is similar to arteries, with a roughly equal proportion of elastin and collagen. Indeed, while arteries have a collagen to elastin ratio (C/E) ranging from 3.0-1.0, visceral pleura exhibits about a 1.0 C/E ratio (note that because collagen is dominant in most tissue (C/E>>1), a C/E ratio of around 1.0 is considered an elastin dominant tissue). Perhaps more specifically, the C/E ratio of visceral pleura varies to some extent along the various portions of the tissue even with respect to the same lung (e.g., front, dorsal, apex, etc.), as well as from baby, adult, to aged swine. As such, at least one representative C/E ratio range for visceral pleura (including the pulmonary ligament) is from about a 1.2 ratio value to about a 0.8 ratio value (all of which are considered elastin dominant).

As discussed in further detail herein, visceral pleura grafts do not suppress in vivo remodeling, but rather their efficacy is, at least in part, due to the grafts' unique ability to work with the natural in vivo remodeling process to result in a functional vessel graft. Importantly, visceral pleura is abundantly available (e.g., from swine, bovine, and other mammalian sources) and can be easily and quickly fabricated into grafts having numerous diameter sizes. Overall, the composition, biocompatibility, and material properties of the pulmonary visceral pleura make it a strong candidate for vessel grafts.

The pulmonary pleura (also known as visceral pleura) covers the lungs and extends to the hilum where it becomes continuous with the parietal pleura. As the anterior and posterior pleura extend below the pulmonary veins, the two layers of pleura come together to form the inferior pulmonary ligament or, as termed herein, the pleura ligament. Hence, the pleura ligament is a double layer of pleura that drapes caudally from the lung root and loosely tethers the medial aspect of the lower lobe of the lung to the mediastinum. However, and importantly, pleura ligament tissue does not functionally behave the same as two layers of pleura, as the non-isotropy of pleura ligament tissue is notably different than just two layers of pleura. Furthermore, the degree of collagen within the pleura ligament is also different than in two layers of pleura, and the function of the pleura ligament is also different, as pleura ligament tissue resists load in one direction. The pleura ligament tethers the lung and has substantial elasticity (over 200% extension, which may be a lateral extension) to expand with each inflation of the lung.

Similar to the mediastinal pleura previously discussed, the significant elasticity of pleura ligament tissue stems from its high elastin content, which is beneficial in that it largely retains its elasticity post fixation.

The characteristics of pleura ligament tissue and/or pleura tissue are exceedingly beneficial, especially with respect to luminal grafts 10 comprising a small-diameter (≤about 4 mm). Primarily, as previously indicated, the major components of pleura ligament tissue and pleura tissue are elastin and collagen, with elastin being the dominant component. This composition is particularly beneficial with respect to forming luminal grafts 10 because elastin is not as prone to fixation as collagen fibers. Furthermore, where a luminal graft 10 comprises a small-diameter construct, tissue comprising elastin largely maintains its elasticity and hence biological mechanical activity following fixation. Additionally, both pleura ligament tissue and pleura tissue are thin, native tissues that are readily available, easily harvested in large sections, and do not require processing prior to formation.

Moreover, and importantly, mesothelial cells cover the surface(s) of both pleura ligament tissue and pleura tissue, which provides for a slippery, non-adhesive and protective surface. Specifically, pleura ligament tissue, mediastinal pleura, and parietal pleura have mesothelium on both sides, while pulmonary pleura has mesothelium on only one side. The mesothelial surfaces of the pleura ligament and pleura tissue have antithrombotic and anti-adhesive properties, which are especially beneficial in connection with the low-pressure conditions present within a small-diameter vessel and for nerve regeneration conduits and applications. In application, where the inner-most layer 12 of the luminal graft 10 comprises visceral/pulmonary pleura, the tissue is positioned such that the inner surface 17 of the layer 12 comprises the side of the tissue having mesothelium thereon. As pleura ligament tissue, mediastinal pleura and parietal pleura have mesothelium on both sides, such considerations are not necessary where the inner-most layer 12 of a luminal graft 10 comprises any of the aforementioned.

Due to the beneficial characteristics of pleura ligament tissue and the pleura tissue, luminal grafts 10 comprising pleura ligament tissue and/or pleura tissue make superior scaffold for vascular cells and nerve tissue as they do not require any processing prior to formation (such as the stripping of muscle or treatment with antibiotics). Furthermore, it is not necessary to seed the same with smooth muscle cells or fibroblasts before implantation as is required with other constructs. Additionally, it has been determined that such tissues are anti-thrombotic, anti-adhesive and attenuate the growth of scar tissue due to their inherent structure.

Figure 3B:
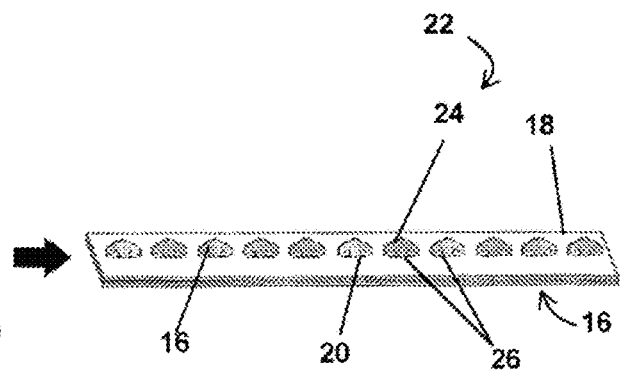

For example, as can be seen in FIGS. 3A and 3B, such tissues comprise abundant glycocalyx, which covers the apical surface of such tissue's mesothelial cells and promotes intracellular adhesion while concurrently inhibiting coagulation and leukocyte adhesion (the tissue in FIGS. 3A and 3B comprises pulmonary pleura). Indeed, it has been determined that swine pulmonary visceral pleura, in particular, contains abundant fibrous extracellular matrices containing collagen, elastin, fibronectin, and laminin, as well as integrins binding sites (e.g., RDG peptide, the active domain of collagen for cell adhesion) and heparin sulfate and sialic acid which are components of glycocalyx. In addition to the benefits described above, such extracellular matrices provide chemical cues to stimulate nerve regeneration and the collagen, elastin, and glycocalyx promote Schwann cell migration and proliferation.

Figure 7:
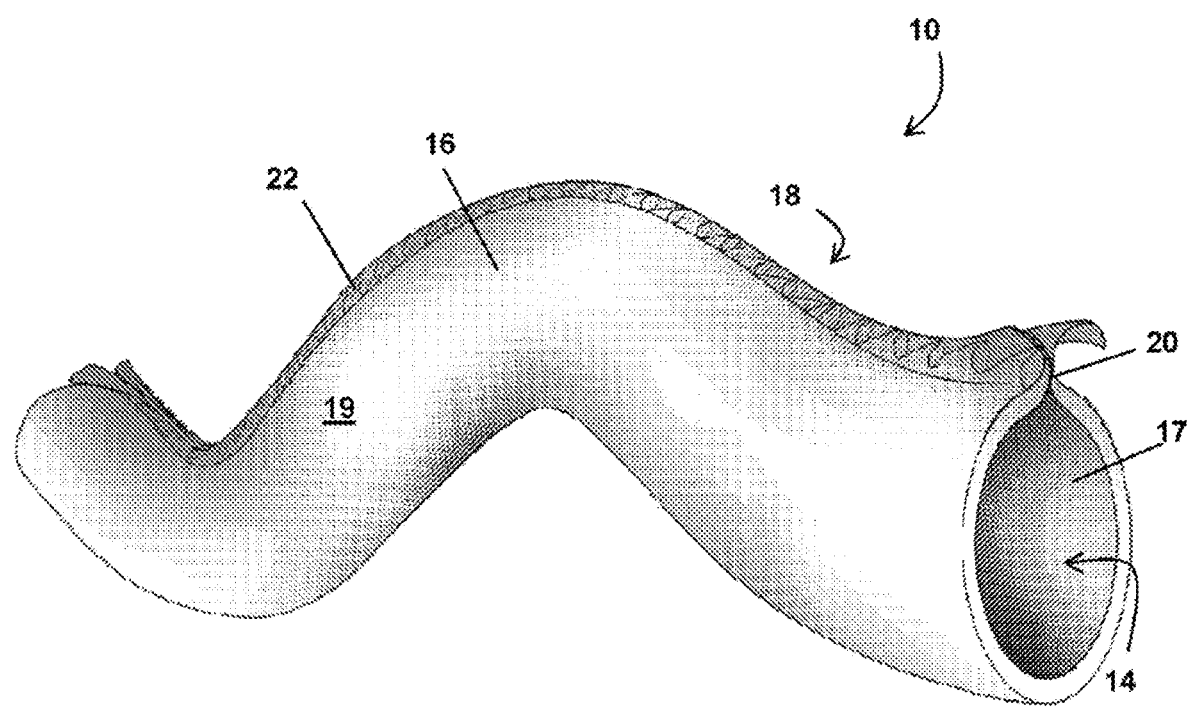
FIG. 7 shows a perspective view of the luminal graft of FIG. 1.

Now referring back to the configuration of the luminal graft 10 itself, as previously described, each layer 12 of the luminal graft 10 is shaped to form an elongated tubular construct comprising a seam 20 running the longitudinal length thereof. The seam 20 comprises the two edges 16, 18 of the layer 12 sealed together via one or more closure mechanisms 22. The precise configuration of the seam 20 may be modified depending upon the particular application of the graft 10 and/or patient specifications. For example, in at least one embodiment, the first edge 16 overlaps the second edge 18 at the seam 20 such that the inner surface 17 of the first edge 16 is secured by the closure mechanism(s) 22 to the outer surface 19 of the second edge 18. As shown in FIG. 7, the edges 16, 18 may alternatively be positioned relative to each other such that the inner surfaces 17 of both edges 16, 18 are held together by the closure mechanism(s) 22 at the seam 20. Still further, the first and second edges 16, 18 may not overlap at all, but rather be coupled end-to-end via the closure mechanism(s) 22.

The closure mechanism(s) 22 may comprise any mechanism or adhesive capable of securely coupling the two edges 16, 18 of the layer 12 together. Furthermore, in at least one embodiment, the closure mechanism 22 is sufficiently flexible or semi-flexible to render the luminal graft 10 with appropriate curvature as needed (see FIG. 7).

The closure mechanism(s) 22 may be positioned along the length of the seam 20 in any fashion provided a secure coupling of the first and second edges 16, 18 can be achieved and a seal formed along the seam 20. For example, in at least one embodiment, a closure mechanism 22 spans the entire length of the seam 20. Alternatively or additionally, closure mechanisms 22 may be positioned strategically or sporadically along the seam 20, provided the two edges 16, 18 of the layer 12 are securely sealed together. Still further, the closure mechanism(s) 22 may be used in conjunction with an adhesive or other biological bonding agent.

Now referring to FIGS. 3A-6B, various embodiments of specific closure mechanism 22 configurations are shown. In the at least one exemplary embodiment of FIGS. 3A and 3B, the closure mechanism 22 comprises an arrow-lock configuration. Specifically, the layer 12 comprises a plurality of protrusions 24 positioned along the length of the first edge 16 and a plurality of corresponding openings 26 positioned along the length of the second edge 18. The protrusions 24 may be comprised of any implantable material suitable for use with the luminal graft 10 such as, by way of non-limiting example, stainless steel, implantable biopolymers, polytetrafluoroethylene, etc.

The protrusions 24 and openings 26 are configured and sized such that each opening 26 may easily receive its corresponding protrusion 24 when the first and second edges 16, 18 are moved in close proximity to each other. Additionally, the size and shape of the protrusions 24 and openings 26 are also configured such that when the protrusions 24 are seated within their respective openings 26, the protrusions 24 cannot be easily withdrawn. For example, as shown in FIGS. 3A and 3B, the protrusions 24 of the closure mechanism 22 may comprise an arrow-like configuration such that they can slide easily into an opening 26, but not be withdrawn therefrom. In this manner, after the protrusions 24 are received by the openings 26, the protrusions 24 are securely positioned therein, thus sealing the first and second edges 16, 18 of the layer 12 together along the seam 20.

It will be appreciated that while the protrusions 24 shown in FIGS. 3A and 3B each comprise an arrow-like configuration, the protrusions 24 may be shaped in any manner provided they are capable of being received by and securely engaging the corresponding openings 26. Furthermore, it is noted that the spacing between the protrusions 24 allows for the underlying luminal graft 10 to remain flexible such that the graft 10 may have curvature as needed when used as a replacement vessel or as a nerve guidance conduit in a body.

Figure 4A:
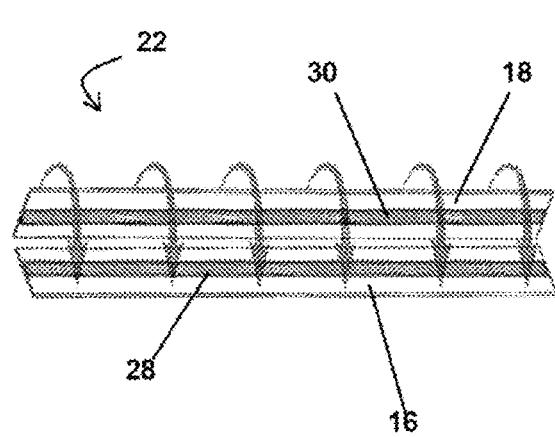
Figure 4B:
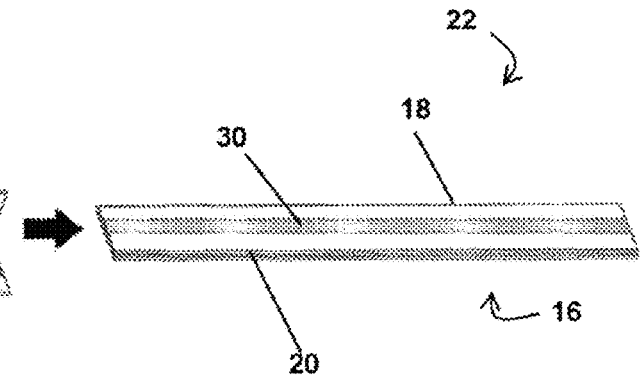

FIGS. 4A and 4B illustrate an alternative embodiment of a closure mechanism 22 of the present disclosure that does not require puncturing or creating a hole in the layer 12 of the luminal graft 10. In the at least one exemplary embodiment of FIGS. 4A and 4B, the closure mechanism 22 comprises a first magnetic strip 28 and a second magnetic strip 30, where the first and second magnetic strips 28, 30 are each configured for attachment to opposing edges 16, 18 of the layer 12. Each of the magnetic strips 28, 30 may be comprised of any permanent magnetic material known in the art and may be flexible, semi-flexible or articulated. In at least one embodiment, the first and second magnetic strips 28, 30 each comprise a thin, smooth, ferromagnetic strip.

The first and second magnetic strips 28, 30 of the closure mechanism 22 may be configured in any shape provided each strip 28, 30 lies relatively flat in application. Furthermore, the first and second magnetic strips 28, 30 are polarized such that they are magnetically biased toward each other. Due to the matching configuration and the bias between the first magnetic strip 28 and the second magnetic strip 30, the first and second magnetic strips 28, 30 are capable of magnetically engaging each other. When the first and second magnetic strips 28, 30 are magnetically engaged, the two magnetic strips 28, 30 form a single unit. Accordingly, when the first edge 16 is folded over or moved into the general proximity of the second edge 18 (see the directional arrows shown in FIG. 4A), the first and second magnetic strips 28, 30 magnetically engage, thereby securely sealing the first and second edges 16, 18 of the layer 12 together.

It will be noted that the magnetic strips 28, 30 may be positioned on either side of the edges 16, 18 of the layer 12. For example, in the least one embodiment shown in FIGS. 4A and 4B, the magnetic strips 28, 30 are positioned on opposite surfaces of the layer 12 (e.g., one on inner surface 17 and one on outer surface 19). In this manner, when the second edge 18 is folded over as indicated by the directional arrows in FIG. 4A, the magnetic strips 28, 30 are in direct contact with each other (see FIG. 4B). Alternatively, the magnetic strips 28, 30 may be positioned such that when the second edge 18 engages the first edge 16, at least one layer 12 is compressed between the two magnetic strips 28, 30 and the magnetic strips 28, 30 magnetically engage each other therethrough.

Figures 5A, 5B:
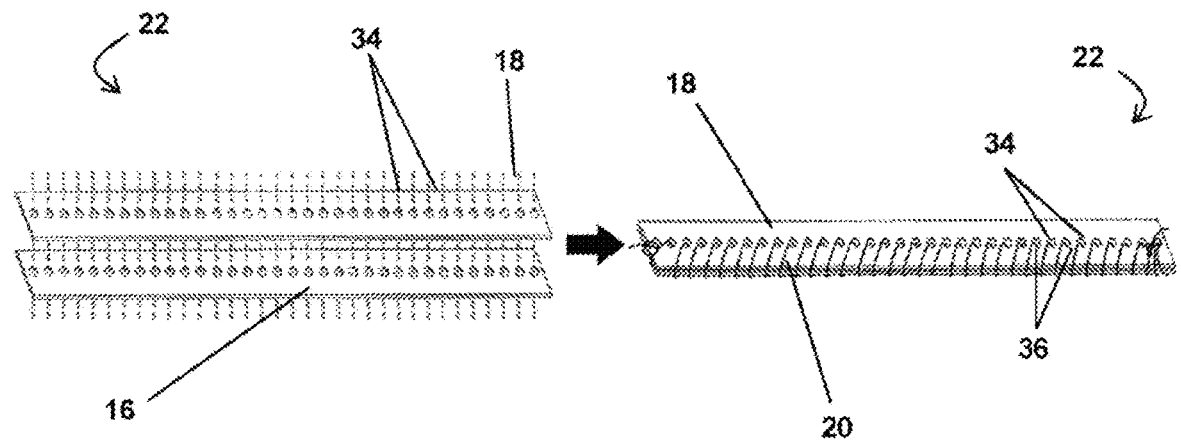

Now referring to FIGS. 5A and 5B, an additional embodiment of a closure mechanism 22 of the present disclosure is shown. In this at least one embodiment, each of the edges 16, 18 of the layer 12 further comprise a series of perforations 34 extending along at least part of the length thereof. The perforations 34 are configured and spaced to allow for sutures 36 to be threaded therethrough as shown in FIG. 5B. In at least one embodiment, the perforations 34 are formed through the layer 12 itself. Alternatively or additionally, the closure mechanism 22 may comprise two perforated strips (not shown), each coupled with an edge 16, 18 of the layer 12 such that the underlying tissue is not punctured by the sutures 36 threaded therethrough. In at least one embodiment, each of the edges 16, 18 of layer 12 comprise both a series of perforations 34 formed therethrough and a perforated strip such that a double perforated line extends substantially the entire length of the seam 20.

The sutures 36 may comprise any material suitable for use in connection with the luminal graft 10 including, without limitation, metal wire, wound and braided wires, suture material, plastic strings, rope and the like. As shown in FIG. 5B, the sutures 36 may be performed to include a single revolution through paired perforations 34 on the first and second edges 16, 18 thereby defining a loop and securing the seam 20. In this at least one embodiment, the loops are positioned perpendicular to the longitudinal axis of the seam 20. It will be appreciated that the suture 34 and its resulting loops are flexible and may be adjusted in shape, size and orientation based on how the suture 34 is tensioned, the suturing technique employed and/or the diameter(s) of the underlying luminal graft 10 (e.g., pursuant to certain principles of vascular surgery, the smaller the diameter of the graft, the smaller the suture). Accordingly, the underlying luminal graft 10 may be flexible or rigid depending upon the type of suture and suturing technique employed.

Figures 6A, 6B:
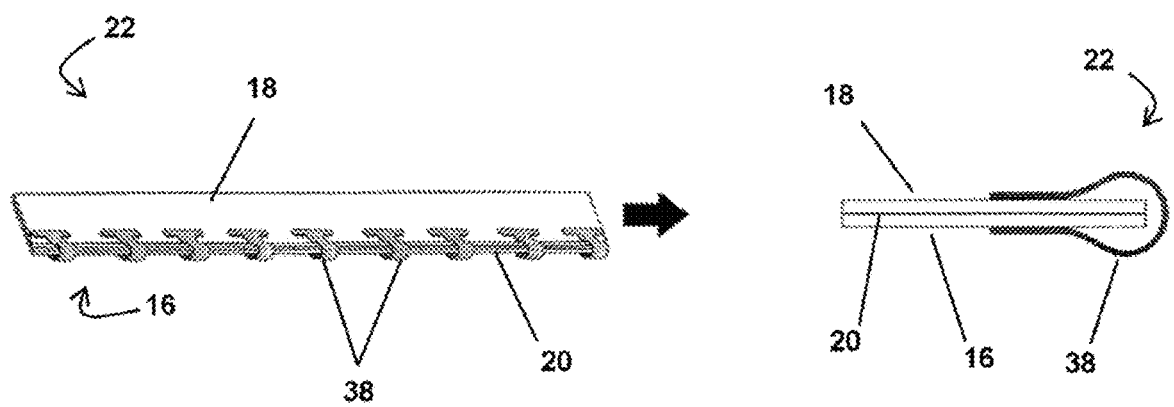
FIG. 6A shows an embodiment of a clamp closure mechanism of a luminal graft according to the present disclosure.
FIG. 6B shows a cross-sectional view of the clamp closure mechanism of FIG. 6A.

FIGS. 6A and 6B illustrate yet another embodiment of a closure mechanism 22 of the present disclosure. In this embodiment, the closure mechanism 22 comprises a series of clips 38 positioned along the length of the seam 20 of the luminal graft 10. Each clip 38 of the closure mechanism 22 is configured and sized to securely compress the edges 16, 18 of the layer 12 together when such edges 16, 18 are positioned within the clip 38 and the clip 38 is deployed. For example and as shown in the cross-sectional view of FIG. 6B, in application, the two edges 16, 18 of the layer 12 are brought together to form seam 20 and the clips 38 are slid thereover. The clip 38 may then be compressed or deployed, thereby sealing the edges 16, 18 of the layer 12 together. The clips 38 may comprise any configuration, provided they are comprised of a material suitable for use in connection with the luminal graft 10 and can securely engage the edges 16, 18 of the layer 12 and seal the seam 20.

FIG. 7 illustrates a perspective view of at least one embodiment of a luminal graft 10 according to the present disclosure that is sufficiently flexible to render the graft 10 with curvature. In this embodiment, the luminal graft 10 comprises one layer 12 that is sealed along the seam 20 with a closure mechanism 22 comprising sutures. As shown in FIG. 7, the graft 10 is configured such that the first and second edges 16, 18 of the layer 12 are secured in a manner so that the inner walls 17 of both the first and second edges 16, 18 are in contact with each other.

Due to its unique properties, a luminal graft 10 of the present application is particularly suitable and exceedingly functional for many different medical applications. Primarily, the luminal grafts described herein do not experience the problems associated with conventional luminal constructs such as stenosis, aneurysm or thrombosis formation. Because of this, the luminal grafts 10 are capable of maintaining long-term patency, an undertaking that has not been previously achieved in conventional constructs. Indeed, in at least one experiment conducted using embodiments of luminal graft 10, the grafts 10 were fully functional at 24 weeks following coupling with a murine femoral artery and maintained their patency for 6 months (subject grafts formed of layers of pulmonary pleura and pleura ligament tissue).

Additionally, the luminal grafts 10 of the present disclosure are also capable of arterializing over time. For example, an embodiment of luminal graft 10 was prepared using as graft of femoral artery of rat. Surprisingly, at the 24th week following implantation, the subject luminal graft not only contracted efficiently in response to 60 mM of potassium chloride (about 10 mmHg elevation), but also achieved about 70% of maximal vasodilation in response to an endothelium-dependent vasodilator (acetylcholine, ACh). Furthermore, vasodilation in response to a nitric oxide donor showed definite vascular tone, and significant Endothelin1 (ET1)-induced contraction was achieved. Accordingly, all functional measurements indicate that the luminal graft had arterialized and was functioning as a true artery. Histological images confirmed that a substantial smooth muscle media developed (as shown in FIGS. 15A and 15B) adjacent to the graft and endothelium covered the luminal surface at this time point (as shown in FIGS. 15B and 12C). The external space of the graft was occupied by connective tissue which combined with the graft to act as the adventitia of the new artery (FIG. 15A).

In light of this, in at least one application, embodiments of the luminal graft 10 may be employed as an arteriovenous (AV) graft for use in connection with the delivery of hemodialysis. An AV graft is created by connecting an artery to a vein with a tube of biocompatible material, and implanting the tube subcutaneously. The AV graft then functions as an artificial vein that can be used repeatedly for needle replacement and blood access. A high occurrence of thrombosis has historically been associated with this procedure, which typically develops due to poor blood flow therethrough. Furthermore, aneurysms and graft failure are additional common complications of conventional AV grafts in hemodialysis patients.

The luminal graft 10 of the present disclosure is suitable for use as an exemplary AV graft due to its unique ability to arterialize and avoid the complications typically associated with conventional grafts. Specifically, because the luminal graft 10 is capable of arterialization, the luminal graft 10 is capable of maintaining adequate blood flow through the vascular access point when employed as AV graft, thereby reducing the likelihood of thrombosis. Additionally, the intimal wall of the luminal graft 10 is an anti-thrombotic material that does not produce stenosis or aneurysm. Accordingly, application of the luminal graft 10 of the present disclosure as an AV graft for hemodialysis overcomes many of the shortcomings of conventional AV grafts.

Yet another exemplary application of the luminal graft of the present application relates to peripheral nerve regeneration techniques (for example, tubulization). As previously described, although it is widely accepted that the peripheral nervous system is capable of regeneration in a laboratory setting, current strategies are associated with quite significant limitations in a patient's functional recovery. Indeed, all autologous nerve graft alternatives (including decellularized nerve grafts and autologous and non-autologous conduits) demonstrate some degree of efficacy, but only when used with sensory nerves having small gaps (<3 cm). There is a significant need for nerve guidance conduits capable of repairing large gaps.

Generally, with respect to the peripheral nervous system, there are four requirements for an "ideal" tissue-engineered nerve graft: 1) that it is compatible with the surrounding tissues; 2) that it is of an adequate size and length; 3) that it contains substances that enable and support axonal regeneration of the nerve; and 4) that it protects the regeneration of the nerve fibers from scar invasion. Generally, biological tissue is better on compatibility as compared to artificial tissue. In the graft, complete compatibility of pleura tissue with the host was found as there was no evidence of inflammation or rejection of the graft. Here, due to the composition and configuration of the luminal graft 10 and, perhaps more specifically, the use of swine PVP which is acellular and contains both collagen and elastin, the intimal walls thereof are anti-adhesive, provide protection, and attenuate the growth of scar tissue. Accordingly, the luminal graft 10 contains substances that enable and support axonal regeneration of the nerve and is capable of protecting the regenerating nerve fibers from scar invasion when used as a nerve guidance conduit.

Furthermore, the luminal graft 10 can be manufactured to various diameters and lengths depending on the particular application and/or nerve(s) at issue. In this manner, the luminal graft 10 can be formed into a nerve guidance conduit having a size and length tailored to the nerve lesion/defect at issue (see FIGS. 14A-14C). Finally, the materials that form luminal graft 10 (namely, pleura ligament tissue and/or pleura tissue) are biocompatible, provide sufficient flexibility to achieve an optimal nerve regeneration environment, and do not cause nerve compression.

Consequently, it is apparent that the characteristics of the luminal graft 10 and its underlying materials satisfy all major requirements of a nerve regeneration conduit. Furthermore, experimental results stemming from tests of the luminal graft 10 in this capacity (described in further detail below) showed that the resulting nerve guidance conduit is capable of maintaining long-term patency and even recovers neuromuscular functions.

Accordingly, use of pleura ligament tissue and/or pleura tissue in the composition of the luminal graft 10 enables the graft 10 to be effective in the aforementioned applications in large part because it is capable of maintaining long-term patency. With respect to blood vessels, the disclosure of the present application provides for a luminal graft 10 suitable for the replacement of blood vessels, including, without limitation, small-diameter blood vessels. Use of pulmonary ligament tissue and/or visceral pleura in the composition of luminal graft 10 enables the graft 10 to be effective as a functional small-diameter conduit vessel (for vascular or nerve applications, for example) capable of maintaining long-term patency. Because of the mesothelial surfaces of glutaraldehyde-fixed pleura ligament tissue and pleura tissue, as well as the other beneficial properties of such tissues described herein, manufacturing these tissues into scaffolds provides a graft environment suitable for the infiltration, adhesion, proliferation and expression and maintenance of cells so that the scaffolds are replaced with tissue made of vascular and/or nerve cells, depending on the application.

In at least one exemplary embodiment especially suited to promote neuronal regeneration for large gaps in nerve injuries, the luminal graft 10 hereof may also comprise one or more intraluminal microchannels 1602. As shown the cross-sectional view of a layer 12 of FIG. 16A, the inner surface 17 of a layer 12 of the graft 10 may comprise or define a series of longitudinally positioned, intraluminal microchannels 1602. Such microchannels 1602 may comprise a series of ridges or other detents formed on the inner surface 17 of a layer 12, or may be defined by a plurality of degradable microspheres 1604 positioned thereon in longitudinally extending rows (see FIG. 2B). In such embodiments, the microspheres 1604 may be aligned and affixed on a layer 12 as parallel cohorts (affixed, for example, using fibrin sealant). It will be appreciated that only the inner-most layer 12 of a graft 10 may comprise the microchannels 1602 or, alternatively, where a graft 10 comprises more than one layer 12 (whether rolled or stacked from different sheets of tissue), more than one (or all) of the layers 12 may comprise microchannels 1602 on each of their respective inner surfaces 17.

The microspheres 1604 themselves may be made of natural and/or synthetic materials. For example, in at least one embodiment, one or more microspheres 1604 may be formed from biological polymers (alginate, chitosan, collagen, and fibrin) and/or synthetic polymers (poly lactic acid (PLA), poly-glycolic acid (PGA), and poly lactic-co-glycolic acid (PLGA)). Furthermore, the microspheres 1604 may be bio-absorbable and/or biodegradable. In at least one exemplary embodiment, the microspheres 1604 are formed from PLGA, which is biocompatible and biodegradable, exhibits a wide range of erosion times, has tunable mechanical properties and, importantly, is an FDA-approved polymer.

As shown in FIG. 16B, where a graft 10 comprises multiple rolled or stacked layers 12 that define microchannels 1602 on their inner surfaces 17, the microspheres 1604 (or other ridges or the like) form pillars between the various layers 12 thus defining microchannels 1602 (space) therebetween. Here, the portion of the graft 10 shown comprises a first layer $12_1$ having longitudinal microchannels 1602 formed from microspheres 1604, positioned below a second layer $12_2$ having longitudinal microchannels 1602 formed from microspheres 1604, positioned below a third layer $12_3$. When multiple layers $12_1$, $12_2$, $12_3$ are used to form the graft 10 (whether using multiple sheets of tissue or through a rolled configuration), each microchannel 1602 formed between two layers comprises four walls—i.e. sidewalls formed by the microspheres 1604 (or ridges or the like) and a ceiling and floor formed by the bases of layers 12 themselves (here $12_1$, $12_2$ and $12_3$).

The distances between the aligned cohorts of microspheres 1604 (and/or ridges or the like) and the diameter of the microspheres 1604/ridges determine the cross area (and ultimately number) of the microchannels 1602. It will be appreciated that the dimensions of the microchannels 1602 and/or microspheres 1604/ridges are fully customizable, need not be consistent throughout an entire layer 12 and/or the luminal graft 10, and may be flexibly adjusted based on the desired application. Microsphere 1604 dimensions may even be adjusted on a per-sphere basis. Furthermore, the number of microchannels 1602 present on a layer 12 may be determined by microsphere 1604/ridge/etc. diameter, the distance between two alignments of microspheres 1604/ridges/etc., the thickness of the tissue forming the layer 12 itself, and the cross-sectional area of the graft 10.

In at least one embodiment, the microsphere 1604 diameters may comprise 100, 200, and/or 400 µm to build up four types of microchannels 1602 having cross areas of about 100×100 µm$^2$, 200×200 µm$^2$, and 400×400 µm$^2$. In another embodiment, the number of microchannels 1602 present will be up to about 150 when the cross area of a microchannel 1602 is around 200×200 µm$^2$ and the diameter of the luminal graft 10/nerve guidance conduit is 3 mm. Still further, in certain cases, microchannels 1602 comprising greater than about 20 µm may be desirable for guiding nerve regeneration due to debris in proximal and distal nerve stumps and fibroblasts migration during nerve regeneration. It will be appreciated that no limitation is intended by providing such dimensional examples. Indeed, as previously stated, the dimensions and number of the microchannels 1602 and/or microspheres 1604 of a luminal graft 10 are fully customizable and may be selected as desired.

In application and as shown in FIG. 16C, the microchannels 1602 provide topographic intraluminal guidance cues, while the extracellular matrix of the tissue of the layers 12 (e.g., swine PVP) provide chemical cues, both of which promote the regeneration of axons 1610. Without the formation of an aligned extracellular matrix bridge within a hollow conduit, limited migration of native Schwann cells on the side of the lesion typically occurs (i.e. hollow conduits are limited in their ability to guide regenerating axons as they lack a scaffold across which regeneration can occur). However, each microchannel 1602 serves as a structural guidance conduit, forming a sub-lumen that mimics the natural fascicular organization of a nerve. In this manner, the microchannel 1602 configuration of the luminal graft 10 can significantly enhance nerve regeneration therethrough. However, even where the luminal graft 10 comprises cohorts of microspheres 1604/ridges and Schwann cells begin to proliferate within the microchannels 1602, the growth factors secreted by such Schwann cells alone may be not be sufficient to stimulate axonal sprouting. To address this, in at least one exemplary embodiment of the present disclosure, exogenous neurotrophic factors are encapsulated within one or more of the microspheres 1604 such that the hydrolysis of the microspheres 1604 during biodegradation/absorption results in the controlled release of the encapsulated substance (i.e. neurotrophic factor(s)) over time. Additionally, as the microspheres 1604 degrade over time, so too will the microchannels 1602 defined thereby, thus allowing for the more spacious accommodation of nerve fiber expansion.

Generally, in nerves, neurotrophic or growth factors can enhance functional regeneration by supporting axonal growth, Schwann cell migration and proliferation, and/or increasing neuroprotection through receptor-mediated activation of a specific intrinsic signaling pathway. Neurotrophins, including without limitation nerve growth factor (NGF), brain-derived neurotrophic factor (BDNF), neurotrophin-3 (NT-3), and neurotorophin-4/5 (NT-4/5), promote nerve regeneration. NGF is present at low concentrations in healthy nerves, but is upregulated following injury in the distal nerve stump and plays an important role in the survival of sensory neurons and neurite outgrowth. NGF (acting through the high affinity TrkA receptor) may improve histological, electrophysiological, and functional outcomes, at least in small animal models of nerve gap injury, and the application of exogenous NGF has been linked to increased sensory neuron regeneration. NT-3 promotes motor neuron survival and promotes the axonal growth of both motor and sensory neurons.

Conventionally, however, the application of neurotrophic factors has not proven effective, especially in promoting nerve regeneration in response to a nerve gap injury. This may be attributed—at least in part—to poor release kinetics because most conventional delivery systems exhibit a high initial burst release. Indeed, it remains difficult to deliver the neurotrophic factors using microspheres over the entire duration of nerve regeneration due to the relatively small capacity of the microspheres themselves.

Encapsulation of one or more neurotrophic factors within a microsphere 1604 of the luminal graft 10 allows for the application of one or more neurotrophic factors in combination with or via sustained release delivery systems or scaffolds to further enhance axonal regeneration—particularly for conduits used with nerve gap injuries. Indeed, this, taken in conjunction with the use of pleura ligament tissue and/or pleura tissue to form the layer(s) 12 of the graft 10 and the use of microchannels 1602 thereon, allow for the successful combination of multiple stimuli, all of which promote axonal regeneration for even larger gaps in nerve injury. The placement of each microsphere 1604 on the layer 12, the substance that each microsphere 1604 contains, and the speed at which each microsphere 1604 dissolves may all be manipulated to achieve the controlled release of particular substances to the regenerating axons in a controlled manner (i.e. to achieve spatially-specific and/or temporal-specific release) and match the Schwann cells' migration and proliferation through the microchannels 1602 of the luminal graft 10.

Primarily, temporal-specific release from the microspheres 1604 may be achieved by using at least two different types of microspheres 1604, each having a different degradation rate for timing the release of the encapsulated substances therefrom. In other words, the biodegradability of the microspheres 1604 is controllable so that the release of neurotrophic factors can occur at two different time points (e.g., first release at 7 days and second release at 21 days, which will be adjusted for longer grafts 10 of 6 cm). Furthermore, the microspheres 1604 may be spatially arranged on the one or more layers 12 to leverage this variable release timing to facilitate desirable results—such as releasing neurotrophic factors or other agents at specified locations within the luminal graft 10 to match the cell migration and proliferation through the microchannels 1602.

For example, in at least one nerve regeneration application as shown in FIGS. 16C and 17, the microspheres 1604 with shorter biodegradable periods are positioned on both the proximal and distal portions of the layer 12/luminal graft 10 where they are connected to the proximal and distal stumps of the injured nerve (see axonal sprout 1610 in FIG. 16C and the areas marked A and D in FIG. 17). Conversely, the microspheres 1604 with longer biodegradable intervals are positioned in the middle portion of the layer 12/luminal graft 10 (see areas marked B and C in FIG. 17, for example).

This delayed release of the substances within the middle microspheres 1604 allows for the Schwann cells 1610 growing through the microchannel 1602 to reach that area of the layer 12 prior to or concurrently with the substances being released. Indeed, using these design principles, the release of the substances from the microspheres 1604 may be coordinated to roughly match the time that the Schwann cells migrate into such areas (i.e. temporal-specific release). In this manner, the late release of the encapsulated substances/neurotrophic factors can effectively match and stimulate Schwann cell proliferation continuously through the microchannel 1602 to fill the entire conduit/microchannel 1602.

It is also contemplated that different layers 12 of the luminal graft 10 may comprise microspheres 1604 having different degradation rates. In at least one embodiment where the luminal graft 10 comprises three concentrically wrapped layers 12, the innermost layer 12 may comprise microspheres 1604 having the fasted degradation (release) rate, followed by the microspheres 1604 of the middle layer 12, while the microspheres 1604 of the outer layer 12 degrade the slowest. Accordingly, the concept of varying degradation rates of the microspheres 1604 to achieve a controlled release of substances encapsulated therein may be employed in any manner to achieve the effect desired.

In addition to varying the degradation rates of the microspheres 1604, the substance(s) encapsulated within a microsphere 1604 and its placement on the layer 12 may also be manipulated to achieve certain goals. As shown in FIG. 17, it may be desirable for the microspheres 1604 encapsulating a first neurotrophic factor to be distributed on the proximal half (marked A and B) of the layer 12 and the microspheres 1604 encapsulating a second neurotrophic factor to be distributed on the distal half of the layer 12 (marked C and D). In this manner, the technique provides the capability for spatially-specific release of an encapsulated substance. Notably, this spatially-specific release may be customized to achieve a desired effect.

In at least one exemplary embodiment, the proximal half (marked A and B) of the layer 12 comprises PLGA microspheres 1604 encapsulating NGF and the distal half of the layer 12 (marked C and D) comprises PLGA microspheres 1604 encapsulating NT-3. In application to nerve regeneration, these neurotrophic factors will be released and anastomose to proximal nerve stumps upon degradation and subsequent rupture of the microspheres 1604. NGF and NT-3 release stimulates Schwann cell migration and proliferation in the microchannels 1602, and the degradation of the PLGA microspheres 1604 also provides more space for the Schwann cells to grow into. The degradation of the PLGA microspheres 1604 may also be controlled at an incremental delay axially from ends to middle of the luminal graft 10 as previously described in connection with the temporal-specific release approaches described herein. There, the release of NGF from the microspheres 1604 placed within the proximal half of the layer 12 will be sequentially delayed from proximal end to middle of the layer 12. The release of NT-3 from the microspheres 1604 placed within the distal half of the layer will be sequentially delayed from distal end to middle of the layer 12 to stimulate Schwann cell migration from the distal stump of the injured nerve to middle of the luminal graft 10. Because NT-3 may delay axonal degeneration, the NT-3 release in the distal half of the luminal graft 10 is designed to delay Wallerian degeneration. Therefore, the proposed luminal graft 10 can bridge a large peripheral nerve defect (for example, up to 6 cm).

The combination of neurotrophic/growth factors can be easily adjusted using the present design and any number of different substances may be employed as desired within the microspheres 1604. Accordingly, by manipulating where and when particular neurotrophic factors or other substances are released, a clinician can use the luminal graft 10 to provide specific therapies tailored to a specific patient and/or the application at issue.

Use of the presently disclosed luminal grafts 10 that incorporate biomolecular therapy, delivery technique, and intraluminal structure to advance a potential "off-the-shelf" peripheral nerve guidance conduit for the repair of large nerve injury (e.g., >4 cm). The embodiments of the luminal graft 10 presented herein are abundant in extracellular matrix (elastin, collagen and glycocalyx), intraluminal microchannels 1602, and spatial and temporary release options for neurotropic factors and/or other substances, the combination of which can effectively promote axonal regeneration for both small and large gaps in nerve injury.

Application of the luminal graft 10 may be particularly useful to patients who have been diagnosed with peripheral artery disease, end-stage renal disease (ESRD), or who have undergone coronary bypass surgeries or suffered peripheral nerve damage. The devices, systems and methods of the present disclosure can be used in connection with such patients to provide a safe, effective, and long-term solution where small-conduit or other vessels may be compromised or damaged.

Now referring back to FIGS. 8A-8D, an exemplary system 200 for manufacturing a luminal graft 10 of the present disclosure is shown. As this system 200 is designed to assemble a luminal graft 10, system 200 comprises and, in application produces, many of the same components of luminal graft 10. Accordingly, like reference numerals depict like components throughout the Figures of this disclosure.

Figure 8A:
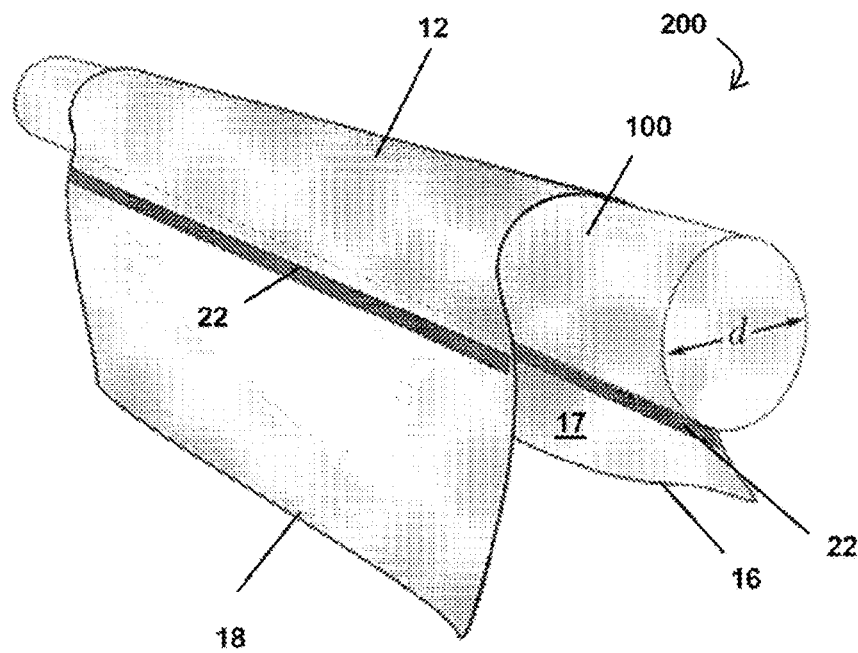
FIGS. 8A-8D show embodiments of a system for manufacturing a luminal graft according to the present disclosure.

FIG. 8A shows an exemplary embodiment of at least a portion of a system 200 for manufacturing a luminal graft 10. In at least one embodiment, the system 200 comprises a mandrel 100 and one or more layers 12 of tissue. Each of the layers 12 of tissue comprises a closure mechanism 22 configured to couple therewith and seal the resulting seam 20. The closure mechanism(s) 22 may or may not be pre-attached to the layer(s) 12 in locations conducive to the creation of a desired seam 20 and a lumen 14 comprising the appropriate diameter D.

The mandrel 100 comprises a cylindrical configuration having a diameter d. The specific configuration and dimensions of the mandrel 100 may be modified, depending on the desired design of the resulting graft 10 and/or particular aspects of such graft's components. For example, in at least one embodiment where a varying diameter luminal graft 10 is desired, the diameter d of the mandrel 100 may gradually increase or decrease along the length of the mandrel 100.

Each layer 12 of the system 200 comprises a relatively flat sheet of fixed tissue comprised of any tissue type suitable for the manufacture of a luminal graft 10. In at least one exemplary embodiment, the layer(s) 12 comprise one or more sheets of pulmonary ligament tissue or visceral pleura. Alternatively or additionally, the layers 12 of a graft 10 may each be comprised of a different type of tissue or even a synthetic material or scaffold. However, even where multiple types of layers 12 are employed in the construct of a luminal graft 10, the inner-most layer 12 of the luminal graft 10 comprises a sheet of pulmonary ligament tissue or visceral pleura such that mesothelium lines the luminal surface of the graft 10.

Where one or more of the layers 12 of a graft 10 comprise tissue, the tissue to be used for the layer(s) 12 of the graft 10 must be harvested and prepared prior to use. Accordingly, such layer(s) 12 may be purchased pre-processed in accordance with the desired specifications or the harvesting and preparation may be performed directly. If necessary, harvesting and preparation may be performed as is known in the medical arts and as is appropriate with respect to the type(s) of tissues used. Where the layer(s) 12 of tissue comprises pulmonary ligament tissue and/or visceral pleura, such tissue may be harvested and prepared as set forth in International Application Number PCT/US2013/025591 to Kassab et al., which is incorporated herein by reference in its entirety, and described generally below (at least in part).

For general reference, an overview of a pulmonary ligament and/or visceral pleura harvesting procedure is described as follows. In at least one method, targeted biological tissues are pre-stretched or otherwise pre-stressed in vivo for optimal function prior to harvesting. Thereafter, the tissue is extracted from a mammal and placed in a relatively cold saline solution to promote preservation. For example, such tissues may be isolated via blunt dissection from an en bloc lung obtained from a local abattoir and subsequently stored unstretched in 0.25% buffered glutaraldehyde for about 48 hours at 23° C. At or before the time of processing, the tissue can be inspected for blood infiltration, fatty material, perforations, and/or other irregularities, and portions of the tissue containing the same can be treated to either removed the undesired components or discarded/disregarded in view of other portions of the tissue that are relatively homogenous and free of undesired properties, such as perforations or fat.

After the desired portions of the tissue are selected from the overall resected tissue, the selected membranes are mounted to remove wrinkles and prevent shrinkage and/or folding during fixation and subsequently submerged in a fixation solution. In at least one exemplary embodiment, glutaraldehyde, for example, at 0.25%, 0.625%, 0.625%, etc., is used for fixation/crosslinking collagen, fibronectin, laminin, and glycocalyx of the tissue, as applicable, noting that elastin is not significantly crosslinked by glutaraldehyde. In addition to its crosslinking capabilities, glutaraldehyde can also inhibit the immunogenicity of the tissue.

In at least one embodiment, the tissue is submerged in the fixation solution for about 24 hours. In at least one embodiment, prior to mounting and/or fixation, or after mounting and/or fixation if desired, the pleura ligament and/or pleura tissue may be pre-seeded to make it more likely to endothelialize. As pleura ligament tissue, mediastinal pleura, and parietal pleura all have mesothelium on both sides and pulmonary pleura has mesothelium on only one side, pre-seeding (also referred to as an endothelial seeding) could be performed on the non-mesothelial side of the tissue. It will be appreciated that while the seeding process may be performed in preparation for the manufacture of a luminal graft 10, this step is optional due to the configuration of the graft 10 and the properties of the underlying pleura ligament and/or pleura tissue.

After fixation, a relatively flat piece of fixed tissue will result. Various sizes and/or thicknesses of processed lung ligament and/or processed visceral pleura tissues can be tailored for specific applications. For example, as is described in additional detail below, the tissue can be dissected into a rectangular sheet of appropriate dimensions and wrapped around a cylinder (e.g., 1.6 mm in diameter) for suturing or otherwise fixing the shape of the graft 10. Additionally, as it has been previously described that the overall thickness of the wall of a luminal graft 10 may be modified based the number of concentric layers 12 used in the manufacture thereof, the thickness of the graft 10 wall may additionally or alternatively be manipulated by using layer(s) 12 having a specific thickness. Accordingly, these grafts 10 can be made in a variety of dimensions and/or configurations that are suitable for numerous grafting applications, including coronary artery bypass grafting procedures.

Figure 8B:
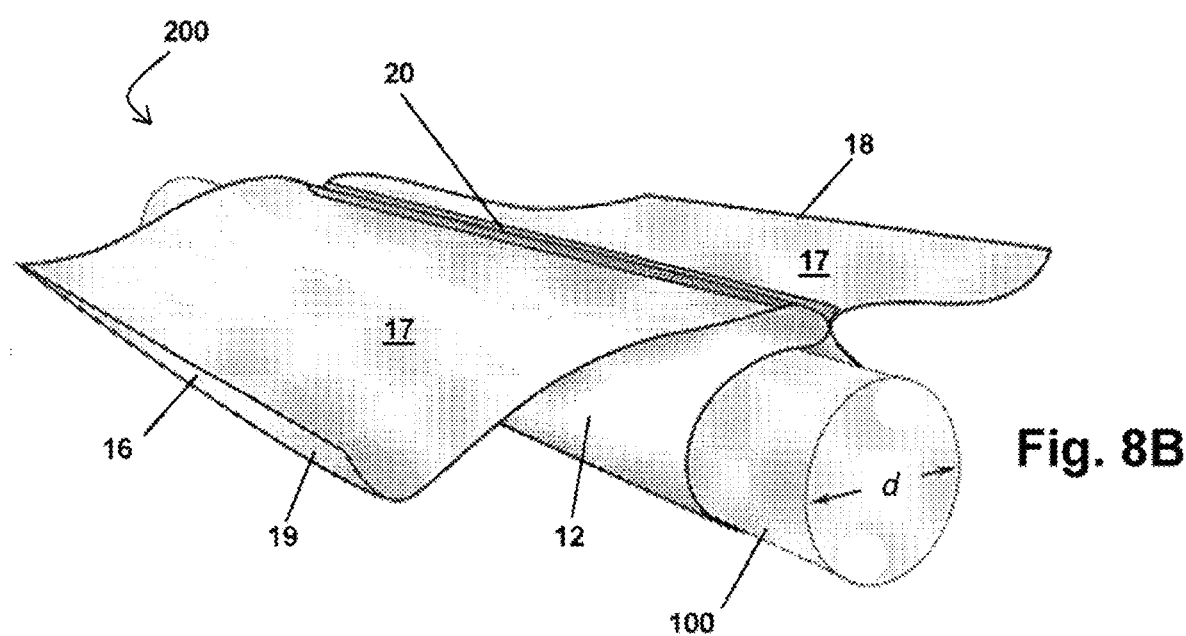

In application, the mandrel 100 forms a model over which the layer(s) 12 of tissue are wrapped as shown in FIGS. 8A and 8B. When the layer(s) 12 are wrapped over the mandrel 100 and the seam 20 is sealed through deploying/engaging the closure mechanism(s) 22, the resulting graft 10 comprises a configuration similar to the shape of the mandrel 100 (see FIG. 8C). Most notably, the lumen 14 of the resulting graft 10 comprises a diameter D that is equivalent to the diameter d of the mandrel 100. Where the system 200 comprises more than one layer 12, the process of wrapping the layer 12 around the mandrel 100 and deploying the closure mechanism(s) 22 is repeated for each subsequent layer 12. It will be appreciated that the closure mechanism(s) 22 need not comprise the same configuration for each layer 12 of the system 200 and, in fact, may even comprise different configurations along the same seam 20.

Figure 8C:
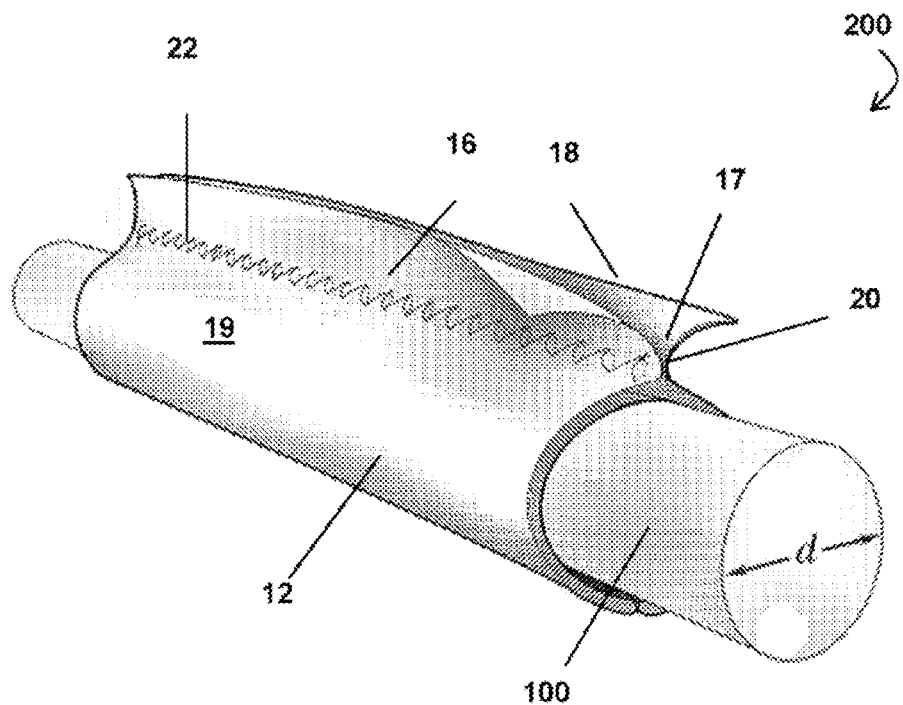
Figure 8D:
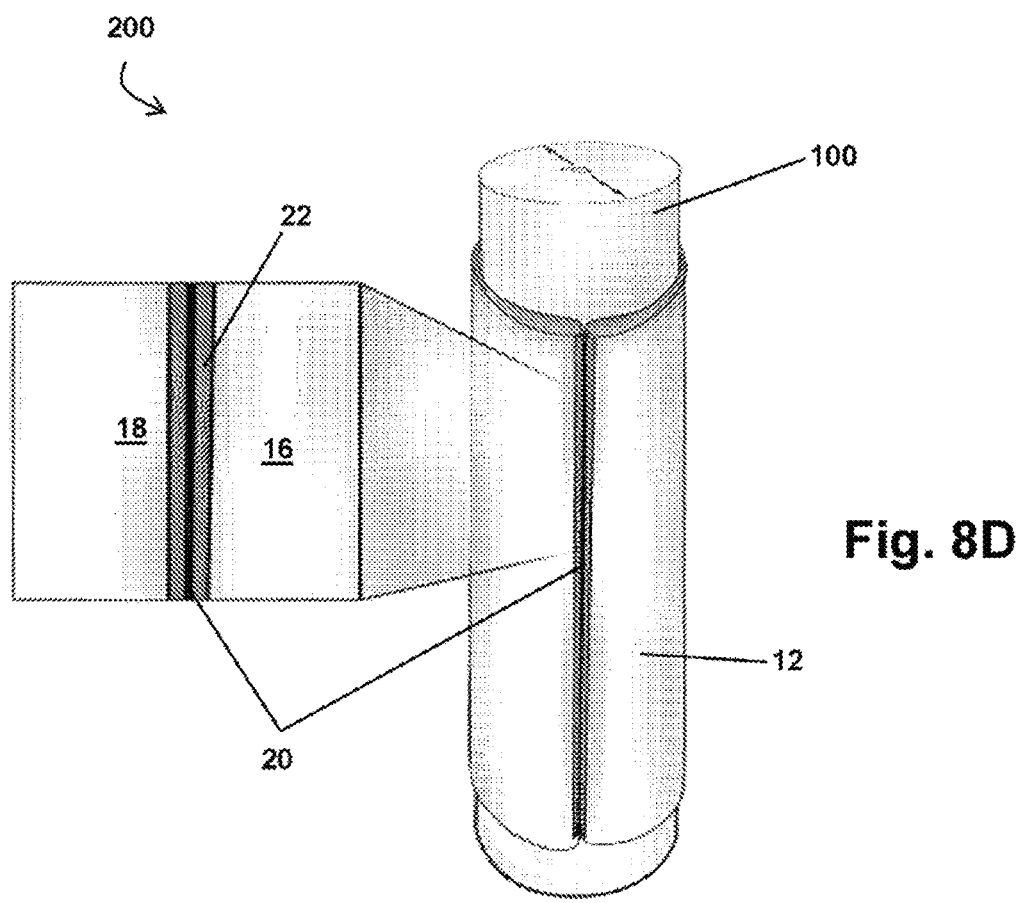
Figure 9:
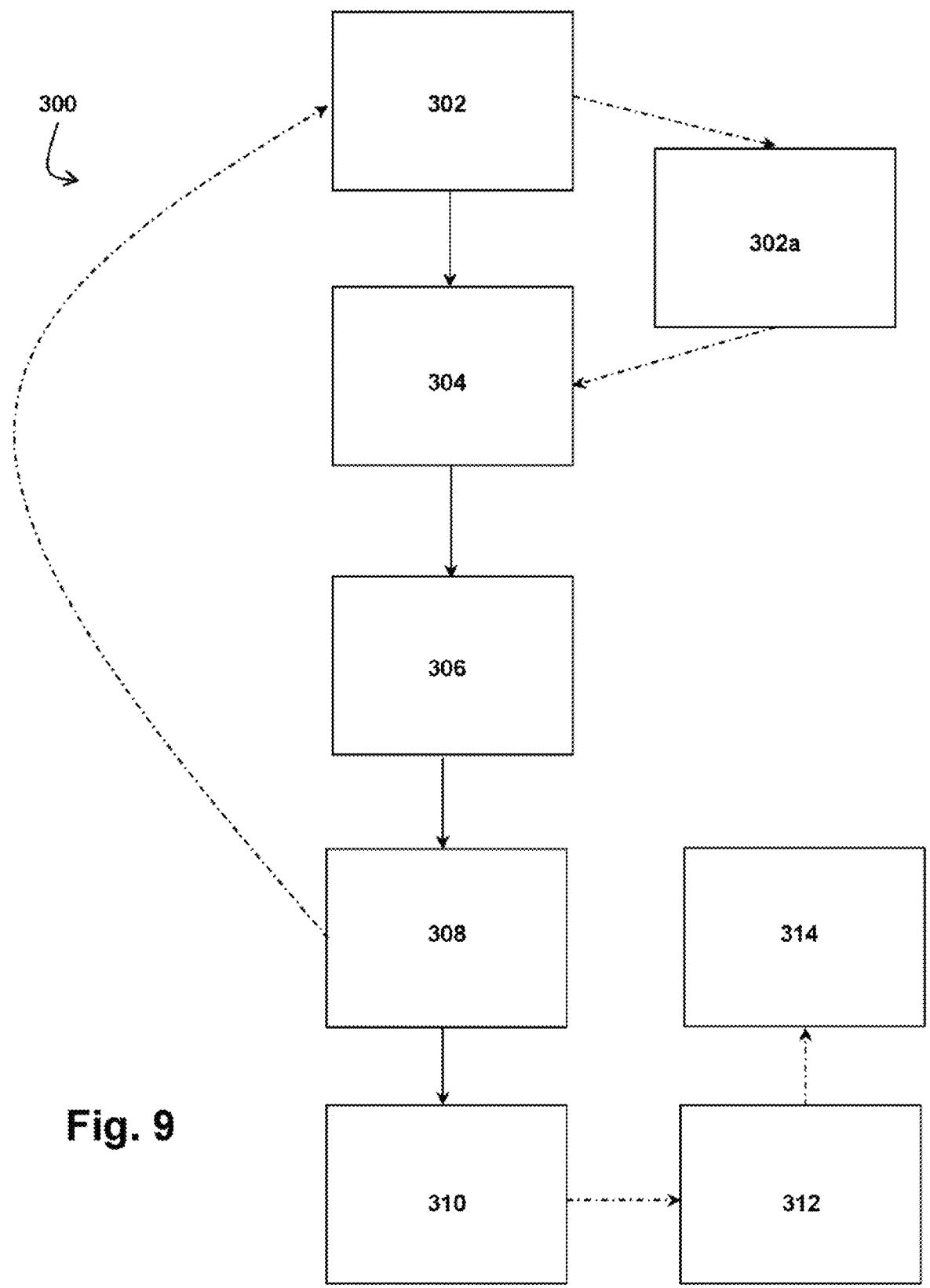
FIG. 9 shows a flow chart depicting various steps of a method for manufacturing a luminal graft according the present disclosure.

Now referring to FIG. 9, a flow chart is shown representing a method 300 for manufacturing a luminal graft 10 in accordance an exemplary embodiment of the present disclosure. FIGS. 8A-8D will also be used for reference in describing the various steps of method 300.

In at least one embodiment, at step 302, the lumen 14 of the luminal graft 10 is formed as shown in FIG. 8. Specifically, a first layer 12 is wrapped around the mandrel 100 such that the first and second edges 16, 18 of the layer 12 are positioned adjacent to each other and the mandrel 100 is substantially encased in the layer 12. As previously discussed, when the layer 12 comprises pleura ligament tissue, mediastinal tissue, parietal tissue or any other pleura tissue having mesothelium on both of its sides, it is irrelevant as to which side of the layer 12 faces toward the mandrel 100. However, where the layer 12 comprises pulmonary pleura or any other type of pleura tissue having mesothelium on only one of its sides, at step 302, care should be taken to position the layer 12 relative to the mandrel 100 such that the mesothelium side of layer 12 faces the mandrel 100 (and thus forms the interior wall or luminal surface of the luminal graft 10). In this manner, the luminal graft 10 is configured such that the mesothelium coats the inner surface 17 (i e luminal surface) of the graft 10 and provides an exemplary scaffold for vascular and/or nerve cells along with its non-thrombogenic properties.

In the embodiment shown in FIG. 8A, the closure mechanism 22 comprises magnetic strips that were pre-attached to the layer 12. In such an embodiment, after the layer 12 is wrapped around the mandrel 100 at step 302, the method 300 proceeds directly to step 304. However, in the event the closure mechanism 22 was not pre-attached to the layer 12, method 300 proceeds from step 302 to step 302a prior to advancing to step 304. At step 302a, the appropriate closure mechanism(s) 22 is/are attached to the layer 12 in the designated position(s).

At step 304, the closure mechanism(s) 22 of the layer 12 is/are positioned for deployment. For example, as shown in FIG. 8B, the inner surface 17 of the first edge 16 is positioned adjacent to the inner surface 17 of the second edge 18 such that the first and second magnetic strips are aligned. At step 306, the closure mechanism(s) 22 are engaged and otherwise deployed, thereby forming seam 20 along the length of the graft 10 and sealing the construct. FIG. 8B illustrates system 200 at step 306 of method 300, where the closure mechanism 22 comprises two magnetic strips. Likewise, FIG. 8C illustrates system 200 at step 306 of method 300 where the closure mechanism 22 comprises perforated strips and sutures.

At step 308, any extra tissue is trimmed away from the exterior of the graft 10 adjacent to the seam 20, thereby minimizing the profile of the same. FIG. 8D shows a close-up view of a seam 20 where the extra tissue has been trimmed away.

In the event the luminal graft 10 comprises a multi-layered construct, following step 308, the method 300 returns to step 302. Accordingly, the second layer 12 is wrapped around the previously wrapped layer(s) of tissue 12 and the underlying mandrel 100. As previously described, any additional layers 12 (other than the inner-most layer 12) can comprise the same or different types of tissue and/or synthetic materials depending on the desired specifications for the luminal graft 10. Thereafter, the method 300 advances through the steps as previously described for each of the remaining layers 12 (e.g., if the luminal graft 10 comprises three layers 12, step 302-308 will be repeated three times). Furthermore, in at least one embodiment, step 302 may additionally comprise aligning any subsequent layers 12 of the luminal graft 10 relative to the previously wrapped layer(s) 12 such that the seams 20 of adjacent layers 12 are offset. For example, as shown in FIG. 2, placement of the seams 20 on the luminal graft 10 may be varied to ensure the construct is sealed and to prevent leaks.

When the final (i.e. outer) layer 12 has been secured at step 308, the method 300 advances to step 310. At step 310, the mandrel 100 is slidingly removed from the lumen 14 of the luminal graft 10, thus resulting in a luminal graft 10 having a diameter D and configuration dictated by the underlying mandrel 100. At optional step 312, the luminal graft 10 may be stored in about 0.25% buffered glutaraldehyde until implantation, and at optional step 314, the graft 10 may be rinsed repeatedly (for example, five (5) times) with saline and incubated in 50 U/ml heparin saline for about thirty (30) minutes prior to implantation. Implantation of the resulting graft 10 may follow the standard techniques of vascular surgery for anastomosis or arteriovenous grafting, microsurgery for nerve guidance conduits, or other applicable methods as appropriate.

In application, at least certain embodiments of the grafts 10 of the present disclosure utilize the natural remodeling process of the host to turn passive grafts 10 into functional vessels. Unlike several conventional approaches that attempt to stymie the remodeling process (e.g., drug elution), the grafts 10 and techniques hereof exploit natural remodeling to orchestrate the engineering of a new vessel. In particular, the grafts 10 can develop into functional conduits in a coronary revascularization setting, even under the complex geometries of coronary arteries in motion. Indeed, following several in vivo and in vitro studies, certain small-diameter grafts 10 (some with diameters ≤1.0 mm) were even patent at 6 months post-implantation, with functional endothelial and smooth muscle cells. Details of such tests and validation processes will now be detailed below; however, it will be understood that such studies and findings are included for explanatory and validation purposes only and are not intended to be limiting in any way.

Now referring to FIG. 18, when a luminal graft 10 comprising microspheres 1604 is manufactured, each layer 12 is coated with the microspheres 1604 such that the microspheres 1603 are aligned and affixed to the layer 12 in parallel cohorts. The layer(s) 12 coated with the parallel lines of microspheres 1604 is/are then assembled into a luminal graft 10 to form the microchannels 1602.

In at least one embodiment, the alignment of the microspheres 1604 and their subsequent affixation to the layer 12 is facilitated by a grating module 1800. FIG. 18 shows a schematic of at least one embodiment of such a grating module 1800. The grating module 1800 comprises a series of notches 1802 separated by intervals 1804, which may be used to axially align microspheres 1604 in preparation for affixing the microspheres 1604 to a layer 12 of the graft 10. The grating module 1800 itself may be manufactured using etching techniques.

The dimensions of each notch 1802 and interval 1804 are selected to produce the desired microchannel 1602 dimensions on the layer 12 when the microspheres 1604 are affixed thereto. Optionally, the depths of the notches 1802 may be somewhat smaller than their respective widths to facilitate the affixation of the microspheres 1604 to the layers 12 (i.e. so the microspheres 1604 are raised up a bit above the top of each interval 1804). For example, in at least one embodiment, the dimensions of the notches 1802 comprise 100, 200, 400 µm in width and 80, 160, 320 µm in depth, respectively, and 6 cm in length (here the notch depths are 20% smaller than the notch widths). Such dimensions can accommodate microspheres 1604 having diameters of 100, 200, 400 µm, respectively. Furthermore, in such example, the intervals 1804 of the notches 1802, a parameter that determines the dimensions of the microchannels 1802, are 100, 200, and 400 µm, respectively. Notably, the dimensions of the intervals 1804 and notches 1802 are independent of the diameters of the microspheres 1604 and the cross figuration of the microchannels 1602 can be adjusted by changing the dimensions of the intervals 1804. Furthermore, while specific examples of grating module 1800 dimensions have been provided, it will be appreciated that it shall not be limiting and any dimensions (and even various dimensions within the same grating module 1800) may be employed.

In application, the microspheres 1604 are loaded into the notches 1802 of the grating module 1800 (see FIG. 19), which forms one-by-one rows of microspheres 1604. Where microspheres 1604 having varying degradation rates and/or encapsulating various substances are employed, the microspheres 1604 are positioned on the grating module 1800 according to the desired degradation duration (e.g., microspheres 1604 having faster degradation rates (early rupture—shown in FIG. 19 as light) at the proximal and distal ends, and microspheres 1604 having slower degradation rates (late rupture—shown in FIG. 19 as dark) in the middle portion of the grating module 1800) and/or positioning of where the substances should be released within the resulting microchannels 1602. The loading of the microspheres 1604 into the grating module 1800 may be performed manually or, in at least one embodiment, by a robot. For example, a robot for biological 3D printing (e.g., Regenova 3D printer) can be employed to precisely distribute various microspheres 1604 at target positions on the grating module 1800.

Likewise, a rectangular sheet 1902 of PVP or other desired material that will form one or more layer(s) 12 is trimmed to a designed length (e.g., 7 cm) and width (e.g., 1.2 cm for 1 mm diameter guidance). In at least one embodiment, the sheet 1902 may be sterilized with 0.1% (v/v) peracetic acid in PBS at 37° C. for 3 hours before being coated with the microspheres 1604. The sheet 1902 is then spread/sprayed with a sealant or adhesive 1904 (such as fibrin sealant, for example). Fibrin sealant has been applied for sealant or glue in various clinical practices and may have positive effects on nerve regeneration.

Once the microspheres 1604 are loaded and axially aligned on the grating module 1800 (either randomly or in a desired order), the sheet 1902 is applied adhesive-side down to cover the grating module 1800 such that the microspheres 1604 affix to the sheet 1902 via the adhesive/sealant 1904. After the adhesive/sealant 1904 is solidified or otherwise cured (if applicable), the sheet 1902 is separated from the grating module 1800, thereby also removing the microspheres 1604 from the notches 1802 of the grating module 1800 as well as they are now affixed to the sheet 1902 via the adhesive/sealant 1904. Indeed, the resulting sheet 1902 is coated with the microspheres 1604 aligned in one-by-one longitudinal rows thereon, forming the microchannels 1602 therebetween. The transverse dimensions of a single microchannel 1602 in the luminal graft 10 is determined by the diameter of microspheres 1604 and interval 1804 of the notch 1802 on the grating module 1800. Accordingly, the method described herein produces a sheet 2000 pre-coated with microspheres 1604 that may then be used to fabricate the luminal graft 10.

Now referring to FIG. 20, one possible method for fabricating the luminal graft 10 from the pre-coated sheet 2000 is to roll the sheet 2000 up into a multi-layer 12 cylinder. Fibrin sealant or another adhesive/sealant may be used to glue the layers 12 during rolling up the sheet 2000; however, the microspheres 1604 distributed within the layers 12 will act as pillars and sustain the microchannels 1602 therein. It will be appreciated that, with this method for fabricating a luminal graft 10, the initial size of the sheet 2000 will dictate the resulting diameter of the luminal graft 10.

At least one alternative method for fabricating the luminal graft 10 from the pre-coated sheet 2000 is shown in FIGS. 21A and 21B. There, a plurality of pre-coated sheets 2000 are stacked to assemble a cubic construct 2100 comprising multiple layers 12 (using fibrin sealant or other glues/adhesives between the layers 12). The precise number of sheets 2000 used to form the cubic construct 2100 can be modified depending on the desired diameter of the resulting luminal graft 10. In at least on embodiment, for example, the cubic construct 2100 may comprise 5 to 20 sheets 2000 such that it comprises a thickness of 1 to 4 mm.

A cylinder is trimmed from the cubic construct 2100 as shown in FIG. 21B. In at least one embodiment, the cylinder is trimmed to comprise a 1 to 4 mm diameter. Thereafter, an epineurium 2102 comprising a sheet of PVP or other desired material (without microspheres 1604 affixed thereto) is wrapped around the trimmed cylinder and glued/sealed thereto to fabricate the luminal graft 10.

As previously noted, the fractional area of microchannels 1602 in the luminal graft 10 comprising microspheres 1604 is adjustable since microsphere 1604 diameter and grating interval 1804 may vary arbitrarily and the thickness of the tissue layer 12 (swine pulmonary ligament tissue and/or visceral pleura in particular) can vary from 30 to 70 µm (depending on the regions harvested). Additionally, pulmonary ligament tissue and/or visceral pleura thickness of animal species may vary from about 20 µm (rabbit) to about 300 µm (bovine). Accordingly, the broad range of both microsphere 1604 dimensions and sheet thicknesses available provide the flexibility for optimization of fractional area of the microchannels 1602 present within the luminal graft 10.

In Vitro Studies

In vitro studies were performed to evaluate the composition and mechanical properties of fresh and fixed visceral pleura. Specifically, visceral pleura grafts 10 were implanted within murine 0.8 mm diameter femoral arteries (n=6) for up to 6 months and canine 2.5 mm cerebral artery (n=2) for up to 2 months in order to address the safety and effectiveness of visceral pleura as small-diameter vessel grafts.

In particular, the visceral pleura ultrastructure was viewed with a multi-photon microscope, with the representative fluorescent images are shown in FIG. 10A. The visceral pleura was found to be 64±6 mm thick. Furthermore, as illustrated in the bar graph of FIG. 10A, the visceral pleura was determined to contain about 11.9% collagen and about 13.2% elastin. Notably, the resulting C/E ratio of 1.10 for visceral pleura falls within arteries 3.0-1.0 C/E ratio.

The biocompatibility of the visceral pleura was also assessed. Primarily, the visceral pleura was cut into 15 mm discs, placed into individual wells of a 24-well plate, and pretreated with 1 ml of full media (DMEM supplemented with 10% FBS) for 24 hours at 37° C. prior to testing. Confluent NIH/3T3 fibroblasts were released from tissue culture plates using 0.25% trypsin, spun, re-suspended, and counted. 100,000 cells were added to each well in fresh media and incubated at 37° C. in 5% $CO_2$ for 24 hours prior to imaging. In the final 2 hours prior to imaging, cells were exposed to Live/Dead (Invitrogen) pursuant to the assay instructions. Discs were subsequently imaged on a fluorescence microscope (Olympus) to determine cell attachment, and compared to small intestine submucosa cells that had undergone like treatment. FIG. 10C shows representative images of the visceral pleura (PVP) and small intestine submucosa (SIS) following the study. Specifically, FIG. 10C highlights reduced fibroblast adhesion to visceral pleura as compared to small intestine submucosa, thus supporting that visceral pleura tissue is indeed biocompatible.

In addition, cytotoxicity was evaluated in both 0.25% glutaraldehyde fixed visceral pleura and small intestine submucosa tissue samples. Each sample received a 10% v/v sterile filtered Fetal Bovine. Extracts were prepared using trypsinized NIH-3T3 cells, which were placed into 6-well plates in Full Media at a concentration of 1:40 v/v per well. The plates were incubated overnight to promote attachment.

The media was removed from each well and replaced with 2 mL of the appropriate extract. The plates were then returned to the cell culture incubator and allowed an incubation time of 120 hours. Each well was imaged and rated for toxicity.

FIG. 10D is representative of the results of this cytotoxicity evaluation, showing images of the visceral pleura (PVP) and small intestine submucosa (SIS) tissue samples that illustrate reduced cytotoxicity of the visceral pleura tissue as compared to the small intestine submucosa tissue. It is thought that the lower collagen content of the visceral pleura as compared to other biologically tested scaffolds (pericardium and small intestine submucosa, for example) reduces cytotoxicity and, thus, would ultimately result in improved clinical outcomes when used in grafting applications.

Finally, the mechanical properties of visceral pleura were evaluated. Such testing revealed that visceral pleura is more compliant than pericardium. Furthermore, fresh versus fixed visceral pleura were confirmed to have similar mechanical properties, most likely due to the large elastin content within the tissue as elastin fibers do not undergo fixation. In sum, the composition, biocompatibility, and material properties of the visceral pleura make it a strong candidate for vessel grafts.

In Vivo Studies

A. Graft Performance in Vascular Applications

In addition to the previously described in vitro evaluations, in vivo graft performance was also studied. Now referring to FIGS. 11A and 11B, schematic representations of the in vivo changes to a graft 10 following implantation are shown. In this at least one embodiment, the grafts 10 evaluated comprised visceral pleura and were implanted in murine right femoral arteries (n=6, 0.80 mm in diameter) and canine internal carotid arteries (n=2, 2.5 mm in diameter). The femoral artery grafts 10 were implanted for 6 weeks, 12 weeks, and 6 months, while internal carotid artery grafts 10 were implanted for 2 months. Blood flow was assessed in vivo in femoral grafts 10 using a transonic flow probe (Transonic Systems, Inc.), while carotid graft patency and flow were assessed using an iE33 ultrasound system (Philips). Preliminary data showed that the blood flow in the right femoral grafts was not different as compared to control left femoral arteries, indicative of a successful grafting procedure. In addition, ultrasonic images revealed fully patent internal carotid artery grafts.

On terminal procedure day, the grafts 10 were explanted and prepared for fluorescence imaging or functional assessment. Graft 10 tissue used for immunofluorescence was sectioned using a cryotome and processed with primary and secondary antibodies with fluorescence probes. Nuclei (FIG. 11B-blue) were visualized with Hoechst 33442 (Life Technologies), while elastin (FIG. 11B-red) was identified using anti-elastin antibody and visualized with Alexa Fluor 546 (Life Technologies). Images were obtained using a fluorescence microscope (TE300, Nikon). From these fluorescence images, the full mechanism of the in vivo remodeling process in connection with the grafts 10 was studied.

Preliminary data from this in vivo study supports that the visceral pleura of the graft 10 initially acts as an internal elastic lamina and separates endothelial cells and smooth muscle cells. As illustrated in FIG. 11A, at 10 days following implantation, there was a population of smooth muscle cells (SMC) on the abluminal side of the graft 10, with no evidence of endothelial cells (E) or an internal elastic lamina (IEL). At 12 weeks, the presence of internal elastic lamina was established, as well as accompanying endothelial cells. At this point, smooth muscle cells migrated within the graft 10 itself, which appeared to also be less dense—i.e. remodeled likely due to the matrix metalloproteinase activity of the myofibroblasts destined to be smooth muscle cells. Finally, at 6 months, the entire graft 10 matrix was occupied by organized smooth muscle cells on the abluminal surface of the internal elastic lamina with endothelial cells on the luminal surface, characteristics indicative of a functional artery. Accordingly, the resulting functional organization was orchestrated by the host vessel and facilitated by the graft 10, with the two anastomotic ends being the source of the migrating smooth muscle and endothelial cells and the graft 10 guiding the proper migration thereof.

FIG. 11B shows immunofluorescence images of the graft 10 crosssection at 10 days and 12 weeks following implantation (20× objective). At 10 days, the elastin fibers of the graft 10 can be clearly seen (see the area highlighted by a dashed-white line, which displays as red in the colorized version of the graph, indicative of the graft's 10 elastin content), however smooth muscle cells have started to migrate on the abluminal side of the graft 10 (the remainder of the image which displays as blue in the colorized version, indicative of the cellular nuclei,). At 12 weeks post-implantation, the smooth muscle cells have significantly integrated into the graft 10, such that the area highlighted by the dashed-white line shows up under immunofluorescence as purple, thus confirming the increased distribution of smooth muscle cells (blue under immunofluorescence) and the graft 10 (red under immunofluorescence). The integration process of the smooth muscle cells appears to be complete at 6 months post-implantation, with multiple layers of organized smooth muscle cells.

In addition to the fluorescence imaging, isovolumic myography was used to investigate vasoreactivity of the grafts 10. FIG. 12A shows a representative 0.80 mm diameter, visceral pleura graft 10 prior to implantation and FIG. 12B shows a graphical representation of a visceral pleura graft's 10 functional response to pharmacological vasodilation and constriction after 6 months of in vivo remodeling. Specifically, Endothelin-1, a potent vasoconstrictor, was added to the perfusate to elicit graft constriction and the resulting intraluminal pressure increase was measured. Conversely, the addition of acetylcholine ($10^{-6}$ M) resulted in endothelium-dependent vasodilation and a decrease in pressure. A further decrease in pressure was achieved by the addition of sodium nitroprus side ($10^{-5}$ M), which caused endothelium-independent vasodilation. As shown in FIG. 12B, the preliminary functional data from these studies supports that visceral pleura grafts 10 at 6 months post-implantation are responsive to pharmacological targeting of endothelial and smooth muscle cells.

In sum, the overall data resulting from these in vivo studies is consistent with the small-diameter (0.80-2.5 mm) visceral pleura grafts 10 remodeling in vivo and ultimately developing into functional, patent conduits. Specifically, the data supports that the graft 10 facilitates the creation of a conduit that is structurally and functionally equivalent to a native artery through use of the body's inherent physiological remodeling process. Notably, these grafts 10 all maintained their patency throughout this in vivo evaluation (6 months), even despite their notably small caliber (<1 mm in diameter). These findings are of significant importance as they verify that the presently disclosed grafts 10 can provide a viable, and readily available, option for vessel grafts (including those of small-diameter) that can not only minimize vessel harvesting, reduce procedure times, and decrease the incidence of re-operations, but also significantly reduce patient morbidity and mortality. In other words, the grafts 10 of the present disclosure can provide surgeons access to a variety of readily available, efficacious, small- and large-diameter grafts, which will translate into improved clinical outcomes for a large patient population and reduce overall healthcare costs.

B. Graft Performance in Nerve Conduit Applications

Additional in vivo graft performance was also studied in connection with nerve regeneration. Swine lungs were harvested from euthanized pigs, immediately stored in 4° C. saline, and the pulmonary visceral pleura (PVP) was gently separated from the lung. A solution containing 0.65% glutaraldehyde was used to crosslink the collagen, fibronectin, laminin, and glycocalyx of the PVP and the PVP was folded around a stainless steel module (~1.6 mm diameter cylinder) and sealed longitudinally with a 10-0 suture to form a graft 10 for the sciatic nerve of rats. The cylindrical grafts 10 were sterilized and rinsed 5 times by saline within 30 minutes before implantation in the murine sciatic neurotomy. The results supported that the conduit of PVP supplied by the graft 10 successfully guided axonal regeneration, with the sciatic functional index of implanted PVP grafts 10 showing a significant improvement at 12-weeks post-operation, indicating that sciatic nerve function was improved.

Additionally, immunofluorescence analysis indicated the successful regeneration of nerve fibers through the PVP grafts 10. Perhaps more specifically, biomarkers of peripheral nerve fiber were used to identify the neo-generation of nerve fibers within the grafts 10. Neurofilament, a component of which is neurofilament light polypetide, is a major component of the neuronal cytoskeleton and functions primarily to improve structural support for axon and to regulate axon diameter. The positive fluorescence images of neurofilament light polypeptide in the PVP graft 10 confirmed that the regeneration of axon bridges the proximal and distal stumps of the sciatic nerve. Indeed, the expression of nerve growth factor receptors were strong in the neo-axon in the PVP graft 10, and the extracellular matrices (laminin and sialic acid) for axon growth and vasa vasorum also developed well.

To further validate the successful nerve regeneration using the PVP graft 10, gastrocnemius muscle function was evaluated (gastrocnemius muscle function at least partially reflecting the function of the sciatic nerve). The gastrocnemius muscle in the murine leg innervated by the sciatic nerve graft 10 was compared with the collateral leg comprising an intact sciatic nerve. The ratio of wet muscle mass was 0.50±0.035, with the wet weight of the muscle in the graft leg decreasing to 2.6±0.8 gm (as compared to 6.5±1.3 gm in the control). The immunofluorescence images also indicated a decrease in the dimensions of muscular fibers, but sarcomere were of integration, which implicates partial recovery of neuromuscular functions in the leg innervated by the nerve comprising the sciatic graft 10.

C. Graft Safety and Efficacy

In an additional study, visceral pleura grafts 10 were tested in a chronic ischemic swine model to determine graft 10 safety (patency and thrombosis) and efficacy, as compared to a saphenous vein graft control group. Graft 10 performance was evaluated in vivo using angiography, echocardiography, and electrocardiography. Grafts were also explanted to further assess graft 10 structure and function.

Primarily, lungs were obtained from a local abattoir and transported en bloc for processing. Within two (2) hours of explants, visceral pleura was isolated via blunt dissection from the parenchyma taking care to avoid edges or fissures. Following isolation, specimens were rinsed and stored unstressed in 0.25% buffered glutaraldehyde solution at 23° C. for 48 hours. A sheet of visceral pleura was wrapped around a stainless steel cylinder and sutured together pursuant to the methods described herein. The resulting grafts 10 were then rinsed with sterile saline five times (5×) just before implantation surgery.

As swine coronary vasculature is more similar to humans as compared to other animal models, male swine were used in the in vivo studies (n=16, 60-80 kg in weight). The swine were randomly divided into two groups, Group I and Group II. Two weeks prior to the bypass surgery, an ameroid constrictor was placed around either the left anterior descending artery, distal of the first diagonal, below the second diagonal, or around the left circumflex artery to create an ischemia/infarct in each swine to induce structural and functional heart changes. After two weeks of ameroid constriction, the swine underwent bypass surgery, with Group I receiving the prepared pulmonary visceral pleura grafts 10, while Group II serving as a control group and receiving saphenous vein grafts as per conventional methodologies. Animals were then monitored over the next 3 months, with angiography, echocardiography, electrocardiography, and blood sample collection done at baseline, 2, 4, 8, and 12 weeks.

On the day of non-survival surgery, all grafts were carefully excised, myocardial tissue collected for histology, and each heart was preserved for tetrazolium chloride (TTC) staining. Myocardial tissue samples (~3×3×3 mm) were obtained from epicardium to endocardium and processed and embedded using conventional histological methods. Thin serial sections (~2 μm) were cut and stained in order to visualize the blood vessels and myocardium. The wall thickness of each graft was also measured, including intima, media and adventitia.

Similarly, TTC staining was used to determine infarct size. Specifically, viable myocardium turned a deep red, while infracted tissue was white. Stained sections were then photographed and custom MATLAB software was used to quantify the infarct size. Colored images of TTC-stained sections were converted into an 8-bit scale and thresholded to delineate infarct from viable tissue. Two-dimensional images were reconstructed to determine an accurate three-dimensional volume.

The vasoreactivity of the visceral pleura grafts 10, control saphenous vein grafts, and dissected circumflex artery were also determined using a novel isovolumic myograph approach disclosed in U.S. Patent Publication Number 2009/0023176 to Kassab et al., which is incorporated herein by reference. Generally, the vessels were each placed within a saline solution aerated with 95% $O_2$ and 5% $CO_2$ that was circulated in a tissue bath and maintained at 37° C. Pharmacological agonists were applied externally to the vessel in the bath and the vessel's intraluminal pressure was monitored during vessel contraction and expansion. Additionally, changes in vessel shape were also recorded with a CCD camera.

In line with other studies, both the visceral pleura grafts 10 and the saphenous vein grafts reversed ischemic damage in each of the respective hearts, including improving electrocardiographic and echocardiographic parameters. Additionally, the visceral pleura grafts 10 avoided dilation and exhibited improved patency as compared to the saphenous vein grafts (controls) at 3 months post-implantation. As supported by the results of both the in vitro and in vivo evaluations, visceral pleura—and like tissue having a high elastin content and mesothelial cells such as pulmonary ligament tissue—has significant potential for use in grafting applications and, in particular, luminal grafts with a small-diameter. Due to the availability of such tissue, the use of these tissues in luminal grafting and, specifically, CABG surgery could address a significant clinical problem as it would provide surgeons with numerous conduit size options even with respect to small-diameter grafts.

Additionally, the biocompatibility of swine PVP implanted as blood vessel (patch and graft) and skin grafts was also evaluated. In 4 pigs, carotid arteries remained 100% patency and arterial incisions were remodeled to similar medial thickness with phenotype vascular smooth muscle cells 3 months post-operation following the implantation of swine PVP as carotid artery patches (7 mm×15 mm). Similarly, jugular veins in 6 pigs all remained patency following the implantation of swine PVP as jugular vein patches (12 mm×32 mm), with the incisions under the patches successfully remolding the similar tissue to native vein. Swine PVP implanted in the femoral arteries (0.7 mm luminal diameter) of 30 rats also exhibited very high patency of 91% 3 months post-operation, indicative of excellent biocompatibility. These findings indicate swine PVP in particular can provide a beneficial biomaterial for nerve guidance conduit as well as in vascular applications.

The various devices, systems, and methods for replacing damaged or compromised blood vessels and engineering luminal grafts for various medical applications have various benefits to patients in need of vascular surgery or nerve regeneration. For example, the devices, systems and methods hereof may be employed to facilitate vessel replacement for patients in need of replacement blood vessels including, without limitation, small-diameter conduit vessels. Furthermore, the devices, systems and methods of the present disclosure may be employed to facilitate placement of vascular access—namely, an arteriovenous graft—in connection with delivery of hemodialysis. Additionally, the devices, systems and methods herein may also be employed in connection with nerve regeneration applications and, in particular, tubulization and nerve guidance conduits. FIGS. 14A and 14B show A) a luminal graft according to the present disclosure being used as a nerve guidance conduit, and B) the end of the nerve guidance conduit of FIG. 14B. FIG. 14C shows a close-up view of a sample of pulmonary pleura in vivo.

We have previously disclosed pulmonary visceral pleura (PVP) and pulmonary ligament (PL) as novel tissue for graft purposes, such as disclosed within U.S. patent application publication nos. 2015/0064140 and 2006/0067031 of Kassab et al. To date, our experience show excellent patency (greater 90%) in as long as nine months in a rat model and the formation of a neo-artery (0.8 mm in diameter) from the graft with functional endothelium and smooth muscle cells. In addition to these excellent findings, the AVG requires resistance to multiple (3-4) weekly punctures for dialysis. Since the native PVP and PL tissues are too thin and the need for maturation (thickening of wall) would take several months, it is desirable to combine the ideal surface of PVP or PL with a synthetic tube material (i.e., biological/synthetic hybrid) of appropriate thickness that can withstand multiple punctures with large bore needle. There are at least two approaches to accomplishing the desired outcome.

One exemplary approach is depicted in FIG. 22 and FIG. 23. As shown therein, an exemplary graft 10 (showing inner lumen 14, multiple layers 12 (noting that an exemplary graft 10 referenced herein can have one or more layers 12, such as the one layer 12 shown in FIG. 1 and the multiple layers 12 shown in FIG. 2), inner surfaces 17 of layers 12, and outer surfaces 19 of layers 12) utilizes one or more synthetic materials 2200 (silicone, PTFE, elastomer, or other biologically compatible materials) as one or more layers 12 of graft 10 material, and at least one inner surface 17, such as the inner surface 17 of the layer 12 with the ultimate graft 10 lumen 14) is lined with a biological material 2202 (shown as a series of diagonal lines in FIG. 22), such as PVP or PL, using one or more biological glues 2204 (UV cured, etc.) or other mechanical fixation of the biological material 2202 to the inner surface 17 of the graft 10 (also referred to in such embodiments as a synthetic graft 10, as it comprises synthetic material(s) 2200 and biological material(s) 2202). FIG. 23 shows a graft 10 having one layer 12, as opposed to the multiple layer 12 graft 10 shown in FIG. 22, whereby a biological glue 2204 is shown as being used/applied to help affix biological material 2202 to inner surface 17 of layer 12. FIG. 24 shows a graft 10 also having one layer 12, whereby the biological material is applied directly to inner surface 17 of layer 12, such as either not requiring a biological glue 2204 or incorporating a biological glue 2204 with biological material 2202 to help with application/adhesion.

Another exemplary approach, for example, is to harvest the mesothelium and other surface molecules (glycocalyx such as hyaluronic acid, heparan sulfate, sialic acid, etc.) of the PVP and PL (also referred to herein as biological material 2202) such that they (the biological material 2202) can be sprayed onto the inner surface 17 of a layer 12 of the hybrid graft 10 in combination with adhesion molecules (e.g., platelets) (also referred to herein a biological glues). As such, FIGS. 22 and 23 also depict such an embodiment, whereby biological material 2202 can be applied to inner surface 17 of a layer 12 of the hybrid graft 10, such as by spraying, and an optional biological glue 2204 can also be used whereby said biological glue 2204 is applied, such as by spraying or other application method, prior to or during application of biological material 2202. Biological material 2202 and biological glue 2204 can also be combined and applied to inner surface 17 of a layer 12 of the hybrid graft 10 at a single time, such as by spraying.

FIG. 24 shows a portion of an exemplary hybrid graft 10 of the present disclosure. As shown therein, hybrid graft 10 comprises a synthetic material 2200 and a biological material 2202, whereby the synthetic material 2200 and the biological material 2202 are generally configured as layers. In various embodiments, synthetic material 2200 may be a contiguous layer of material, and biological material 2202 may be a complete/contiguous layer of material or less than a complete/contiguous layer of material. Hybrid graft 10, as shown in FIG. 24, could be shaped as desired, such as ultimately shaped as a cylinder or tube.

FIG. 25 shows an exemplary hybrid graft 10 of the present disclosure configured as a cylinder or tube. As shown therein (in cross-section), hybrid graft 10 comprises a synthetic material 2200 on a relative outside and a biological material 2202 on a relative inside, such that lumen 14 (defined by one or both of synthetic material 2200 and/or biological material 2202) can allow fluid flow therethrough, such as blood, when implanted into a mammalian body. In such a configuration, the fluid (such as blood) would contact the biological material 2202 of hybrid graft 10, while the synthetic material 2200 would be on a relative outside, such as contacting a wall of a blood vessel.

FIG. 26 shows an exemplary hybrid graft 10 of the present disclosure configured as a cylinder or tube. As shown therein (in cross-section), hybrid graft 10 comprises a biological material 2202 on a relative outside, a synthetic material 2200 on a relative inside of that biological material 2202 layer, and another biological material 2202 on a relative inside, such that lumen 14 (defined by one or both of synthetic material 2200 and/or biological material 2202) can allow fluid flow therethrough, such as blood, when implanted into a mammalian body. In such a configuration, the fluid (such as blood) would contact the inner layer of biological material 2202 of hybrid graft 10, while the outer layer of biological material 2202 would be on a relative outside, such as contacting a wall of a blood vessel, such that the synthetic material 2200 may not contact the wall of the blood vessel or fluid flowing through the graft 10.

In various embodiments, synthetic material 2200 comprises a layer of material, and biological material 2202 is applied thereto, either as its own separate layer physically applied thereto, or sprayed thereon, such as by way of a mixture of biological material 2202 and another material, whereby the mixture as a consistency that can be applied to the layer of synthetic material 2200. For example, and as shown in FIG. 27, a mixture 2700 of the present disclosure can comprise biological material 2202, as referenced, and at least one additional material 2702, such as a liquid (water, saline, blood, etc.), a biological glue 2204, or another material.

The novel biological/synthetic hybrid graft 10 of the present disclosure offers a new vascular access paradigm where long access life, low maintenance, and extended interventional intervals are the design goals. This hybrid approach should demonstrate promising performance characteristics such as, antithrombogenesis, a highly mobile structure supporting mechanical arterial behavior and possibly the ability to seal readily following large needle puncture, high resistance to neointimal hyperplasia, and arterial function propagation within the graft 10 by the host. The hybrid graft 10 is especially suited for low flow environments, small diameter applications, and other hostile implant environments which makes it unique within the current graft offerings. These tissue characteristics match up very well to many of the major concerns in the current hemodialysis environment and may offer compelling short and long-term outcomes.

The impact and benefits of the tissue-engineered graft 10 are numerous and significant. Primarily, the hybrid graft 10 can be characterized by the preferred properties of both the fistula and graft, and at the same time, minimize the negatives of both solutions. This novel hybrid graft 10 implant can mature in the near-term like a fully biological graft 10 of the present disclosure, but in the long-term shows traits similar to fistulas. This hybrid graft 10 can demonstrate several important advancements that ultimately support longer access site life for ESRD patients on hemodialysis and the physician's maintenance efforts. First, the hybrid graft 10 solution can offer a readily implantable and predictable platform for surgeons to create vascular access, fast implant-to-first dialysis times, and low failure-to-mature rates that are synonymous with grafts. This hybrid graft 10 offers natural antithrombogenesis performance that lowers the potential for thrombus formation, seen commonly in fistulas and grafts. The hybrid graft 10 can show a unique property in which the host integrates the graft 10 into an artery-like state possibly translating to the long-term benefits of a native fistula (low infection rates and long life). Due to its glycocalyx content, it demonstrates a high resistance to neointimal hyperplasia, which is common in fistulas due to the repeat needle injury, leading to lower stenotic occurrences within the graft 10. One distinct benefit with the availability of this graft 10 would be fewer longer-term tunneled catheter (TC) dialysis patients. In the situation where TC use cannot be avoided and our graft 10 is implanted, the length of time where the TC would likely be short because it's a graft 10. From a cost expenditure perspective, an exemplary hybrid graft 10 of the present disclosure takes less time and processing to manufacture as seen in other engineered grafts, namely it does not require smooth muscle cell or fibroblast seeding and ingrowth, yielding a lower cost of production. For hemodialysis dependent patients, the unique characteristics of this novel graft 10 stands to make a significant contribution in extending the life of a vascular access site and lowering the number of interventions required to maintain access site patency.

While embodiments of grafts and methods of making and using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A luminal graft comprising a generally tubular element configured for nerve cells to grow therethrough, the luminal graft comprising:
   at least one sheet of biological tissue having elastin fibers and collagen fibers, with the elastin fibers being a dominant component thereof; and
   a plurality of microchannels formed on a surface of the at least one sheet of biological tissue, each of the microchannels extending longitudinally between a first end and a second end of the at least one sheet of biological tissue and configured to provide intraluminal structural guidance to nerve cells proliferating therethrough;
   wherein the biological tissue comprises pulmonary ligament tissue or visceral pleura tissue.

2. The luminal graft of claim 1, further comprising a plurality of biodegradable microspheres affixed to the surface of the at least one sheet of biological tissue and positioned in rows extending longitudinally between the first end and the second end of the at least one sheet of biological tissue, wherein the rows of microspheres define side portions of the plurality of microchannels.

3. The luminal graft of claim 2, wherein each of the biodegradable microspheres encapsulates a substance and when the biodegradable microsphere degrades, the substance is released therefrom.

4. The luminal graft of claim 3, wherein the substance comprises a neurotrophic factor.

5. The luminal graft of claim 2, wherein the plurality of biodegradable microspheres further comprises a first set of biodegradable microspheres encapsulating a first neurotrophic factor and a second set of biodegradable microspheres encapsulating a second neurotrophic factor.

6. The luminal graft of claim 5, wherein the first neurotrophic factor comprises NGF and the second neurotrophic factor comprises NT-3.

7. The luminal graft of claim 2, wherein the plurality of biodegradable microspheres further comprises a first set of biodegradable microspheres that have a first rate of degradation and a second set of biodegradable microspheres that have a second rate of degradation; wherein the first rate of degradation is faster than the second rate of degradation.

8. The luminal graft of claim 1, wherein the at least one sheet of biological tissue is arranged to form cylinder comprising a plurality of internal layers, each layer comprising a plurality of biodegradable microspheres positioned in rows extending longitudinally between the first end and the second end of the sheet, wherein the rows of microspheres define side portions of the plurality of microchannels.

9. A luminal graft comprising a generally tubular element configured for nerve cells to grow therethrough, the luminal graft comprising:
- at least one sheet of biological tissue having elastin fibers and collagen fibers, with the elastin fibers being a dominant component thereof; and
- a plurality of microchannels formed on a surface of the at least one sheet of biological tissue, each of the microchannels extending longitudinally between a first end and a second end of the at least one sheet of biological tissue and configured to provide intraluminal structural guidance to nerve cells proliferating therethrough; and
- a plurality of biodegradable microspheres affixed to the surface of the at least one sheet of biological tissue and positioned in rows extending longitudinally between the first end and the second end of the at least one sheet of biological tissue, wherein the rows of microspheres define side portions of the plurality of microchannels;
- wherein the plurality of biodegradable microspheres further comprises a first set of biodegradable microspheres that have a first rate of degradation and a second set of biodegradable microspheres that have a second rate of degradation; wherein the first rate of degradation is faster than the second rate of degradation; and
- wherein the first set of biodegradable micro spheres is positioned at or near the first and second ends of the at least one sheet of biological tissue and the second set of biodegradable micro spheres is positioned in a middle portion of the at least one sheet of biological tissue.

10. A method for performing a luminal grafting procedure, the method comprising the step of:
- implanting the luminal graft of claim 1 within a mammalian body at a location of a proximal nerve stump and a distal nerve stump.

11. The method of claim 10, further comprising the steps of:
- releasing a first set of neurotrophic factors from a first set of the microspheres to facilitate nerve proliferation at or near the first end and the second end of the at least one sheet of biological tissue; and
- releasing a second set of neurotrophic factors from a second set of the microspheres to facilitate nerve proliferation in a middle portion of the at least one sheet of biological tissue.

12. The method of claim 11, wherein the step of releasing a first set of neurotrophic factors occurs at a first time and the step of releasing a second set of neurotrophic factors occurs at a second time, the second time occurring after the first time.

* * * * *